United States Patent
Mekada et al.

(10) Patent No.: US 7,851,601 B2
(45) Date of Patent: Dec. 14, 2010

(54) MONOCLONAL ANTIBODY CAPABLE OF BINDING TO HEPARIN-BINDING EPIDERMAL GROWTH FACTOR-LIKE GROWTH FACTOR

(75) Inventors: Eisuke Mekada, Suita (JP); Ryo Iwamoto, Suita (JP); Shingo Miyamoto, Fukuoka (JP); Kenya Shitara, Tokyo (JP); Akiko Furuya, Machida (JP); Kazuyasu Nakamura, Machida (JP); Kumiko Takahashi, Cambridge, MA (US); Hiroshi Ando, Machida (JP); Kazuhiro Masuda, Machida (JP); Yuka Sasaki, Machida (JP)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 169 days.

(21) Appl. No.: 12/329,946

(22) Filed: Dec. 8, 2008

(65) Prior Publication Data

US 2010/0184958 A1    Jul. 22, 2010

Related U.S. Application Data

(63) Continuation of application No. PCT/JP2007/061487, filed on Jun. 6, 2007.

(30) Foreign Application Priority Data

Jun. 6, 2006    (JP) ............................. 2006-157279

(51) Int. Cl.
*C12P 21/04* (2006.01)
*C07K 16/00* (2006.01)
*A61K 39/395* (2006.01)
*C07H 21/04* (2006.01)

(52) U.S. Cl. .............................. 530/388.24; 424/133.1; 424/141.1; 424/145.1; 435/69.6; 435/70.21; 530/387.3; 530/388.1; 530/388.22

(58) Field of Classification Search ...................... None
See application file for complete search history.

(56) References Cited

PUBLICATIONS

William E. Paul. Fundamental Immunology, 3rd ed., p. 242, 1993.*
Holliger et al. Proc. Natl. Acad. Sci. USA, 90(14):6444-6443, 1993.*
Supplementary European Search Report dated Mar. 23, 2010 in European Application No. 07744826.4.
Khong et al., "Inhibition of heparin-binding epidermal growth factor-like growth factor increases albuminuria in puromycin aminonucleoside nephrosis," Kidney International, vol. 58, No. 3, pp. 1098-1107 (2000).
Kipriyanov et al., "Generation and Production of Engineered Antibodies," Molecular Biotechnology, vol. 26, No. 1, pp. 39-60 (2004).
Miyamoto et al., "Heparin-binding epidermal growth factor-like growth factor as a novel targeting molecule for cancer therapy," Cancer Science, vol. 97, No. 5, pp. 341-347 (2006).
Miyamoto et al., "Heparin-Binding EGF-Like Growth Factor Is a Promising Target for Ovarian Cancer Therapy," Cancer Research, vol. 64, No. 16, pp. 5720-5727 (2004).
Adams et al., "Monoclonal antibody therapy of cancer," Nature Biotechnology, vol. 23, No. 9, pp. 1147-1157 (2005).

* cited by examiner

*Primary Examiner*—David J. Blanchard
(74) *Attorney, Agent, or Firm*—Sughrue Mion, PLLC

(57) ABSTRACT

Medicaments for treating diseases related to HB-EGF escalation are in demand. The present invention provides a monoclonal antibody or an antibody fragment thereof which binds to a cell membrane-bound HB-EGF, a membrane type HB-EGF and a secretory HB-EGF.

13 Claims, 17 Drawing Sheets

(a)

(b)

(c)

(d)

CELL NUMBER

FLUORESENCE INTENSITY

MCAS-TRANSPLANTED MODEL  ES-2-TRANSPLANTED MODEL

MDA-MB-231-TRANSPLANTED MODEL

DAYS AFTER TRANSPLANTATION (DAY)

though CRM197 has therapeutic effects on cancer and cardiac hypertrophy, it also has strong toxicity so that its use as a pharmaceutical has a limit.

```
                         SEQUENCE LISTING

<160> NUMBER OF SEQ ID NOS: 31

<210> SEQ ID NO 1
<211> LENGTH: 2360
<212> TYPE: DNA
<213> ORGANISM: Homo sapiens

<400> SEQUENCE: 1
gctacgcggg ccacgctgct ggctggcctg acctaggcgc gcggggtcgg gcggccgcgc        60
gggcgggctg agtgagcaag acaagacact caagaagagc gagctgcgcc tgggtcccgg       120
ccaggcttgc acgcagaggc gggcggcaga cggtgcccgg cggaatctcc tgagctccgc       180
cgcccagctc tggtgccagc gcccagtggc cgccgcttcg aaagtgactg gtgcctcgcc       240
gcctcctctc ggtgcgggac catgaagctg ctgccgtcgc tggtgctgaa gctctttctg       300
gctgcagttc tctcggcact ggtgactggc gagagcctgg agcggcttcg gagagggcta       360
gctgctggaa ccagcaaccc ggaccctccc actgtatcca cggaccagct gctaccccta       420
ggaggcggcc gggaccggaa agtccgtgac ttgcaagagg cagatctgga cctttgaga       480
```

```
gtcactttat cctccaagcc acaagcactg gccacaccaa acaaggagga gcacgggaaa    540
agaaagaaga aaggcaaggg gctagggaag aagagggacc catgtcttcg gaaatacaag    600
gacttctgca tccatggaga atgcaaatat gtgaaggagc tccgggctcc ctcctgcatc    660
tgccacccgg gttaccatgg agagaggtgt catgggctga gcctcccagt ggaaaatcgc    720
ttatatacct atgaccacac aaccatcctg ccgtggtgg ctgtggtgct gtcatctgtc     780
tgtctgctgg tcatcgtggg gcttctcatg tttaggtacc ataggagagg aggttatgat    840
gtggaaaatg aagagaaagt gaagttgggc atgactaatt cccactgaga gagacttgtg    900
ctcaaggaat cggctgggga ctgctacctc tgagaagaca caaggtgatt tcagactgca    960
gaggggaaag acttccatct agtcacaaag actccttcgt ccccagttgc cgtctaggat   1020
tgggcctccc ataattgctt tgccaaaata ccagagcctt caagtgccaa acagagtatg   1080
tccgatggta tctgggtaag aagaaagcaa aagcaaggga ccttcatgcc cttctgattc   1140
ccctccacca aaccccactt cccctcataa gtttgtttaa acacttatct tctggattag   1200
aatgccggtt aaattccata tgctccagga tctttgactg aaaaaaaaaa agaagaagaa   1260
gaaggagagc aagaaggaaa gatttgtgaa ctggaagaaa gcaacaaaga ttgagaagcc   1320
atgtactcaa gtaccaccaa gggatctgcc attgggaccc tccagtgctg gatttgatga   1380
gttaactgtg aaataccaca agcctgagaa ctgaattttg ggacttctac ccagatggaa   1440
aaataacaac tatttttgtt gttgttgttt gtaaatgcct cttaaattat atatttattt   1500
tattctatgt atgttaattt atttagtttt taacaatcta acaataatat ttcaagtgcc   1560
tagactgtta ctttggcaat ttcctggccc tccactcctc atccccacaa tctggcttag   1620
tgccacccac ctttgccaca aagctaggat ggttctgtga cccatctgta gtaatttatt   1680
gtctgtctac atttctgcag atcttccgtg gtcagagtgc cactgcggga gctctgtatg   1740
gtcaggatgt agggggttaac ttggtcagag ccactctatg agttggactt cagtcttgcc   1800
taggcgattt tgtctaccat ttgtgttttg aaagcccaag gtgctgatgt caaagtgtaa   1860
cagatatcag tgtctccccg tgtcctctcc ctgccaagtc tcagaagagg ttgggcttcc   1920
atgcctgtag ctttcctggt ccctcacccc catggcccca ggccacagcg tgggaactca   1980
ctttcccttg tgtcaagaca tttctctaac tcctgccatt cttctggtgc tactccatgc   2040
aggggtcagt gcagcagagg acagtctgga gaaggtatta gcaaagcaaa aggctgagaa   2100
ggaacaggga acattggagc tgactgttct tggtaactga ttacctgcca attgctaccg   2160
agaaggttgg aggtggggaa ggctttgtat aatcccaccc acctcaccaa aacgatgaag   2220
gtatgctgtc atggtccttt ctggaagttt ctggtgccat ttctgaactg ttacaacttg   2280
tatttccaaa cctggttcat atttatactt tgcaatccaa ataagataa  cccttattcc   2340 ataaaaaaaa aaaaaaaaa                                                2360

<210> SEQ ID NO 2
<211> LENGTH: 208
<212> TYPE: PRT
<213> ORGANISM: Homo Sapiens

<400> SEQUENCE: 2

Met Lys Leu Leu Pro Ser Val Val Leu Lys Leu Phe Leu Ala Ala Val
 1               5                  10                  15

Leu Ser Ala Leu Val Thr Gly Glu Ser Leu Glu Arg Leu Arg Arg Gly
            20                  25                  30

Leu Ala Ala Gly Thr Ser Asn Pro Asp Pro Pro Thr Val Ser Thr Asp
```

```
                35                  40                  45
Gln Leu Leu Pro Leu Gly Gly Gly Arg Asp Arg Lys Val Arg Asp Leu
 50                  55                  60

Gln Glu Ala Asp Leu Asp Leu Leu Arg Val Thr Leu Ser Ser Lys Pro
 65                  70                  75                  80

Gln Ala Leu Ala Thr Pro Asn Lys Glu Glu His Gly Lys Arg Lys Lys
                 85                  90                  95

Lys Gly Lys Gly Leu Gly Lys Lys Arg Asp Pro Cys Leu Arg Lys Tyr
                100                 105                 110

Lys Asp Phe Cys Ile His Gly Glu Cys Lys Tyr Val Lys Glu Leu Arg
                115                 120                 125

Ala Pro Ser Cys Ile Cys His Pro Gly Tyr His Gly Glu Arg Cys His
                130                 135                 140

Gly Leu Ser Leu Pro Val Glu Asn Arg Leu Tyr Thr Tyr Asp His Thr
145                 150                 155                 160

Thr Ile Leu Ala Val Val Ala Val Val Leu Ser Ser Val Cys Leu Leu
                165                 170                 175

Val Ile Val Gly Leu Leu Met Phe Arg Tyr His Arg Arg Gly Gly Tyr
                180                 185                 190

Asp Val Glu Asn Glu Glu Lys Val Lys Leu Gly Met Thr Asn Ser His
                195                 200                 205

<210> SEQ ID NO 3
<211> LENGTH: 86
<212> TYPE: PRT
<213> ORGANISM: Artificial Sequence
<220> FEATURE:
<223> OTHER INFORMATION: Synthetic construct

<400> SEQUENCE: 3

Asp Leu Gln Glu Ala Asp Leu Asp Leu Leu Arg Val Thr Leu Ser Ser
 1               5                  10                  15

Lys Pro Gln Ala Leu Ala Thr Pro Asn Lys Glu Glu His Gly Lys Arg
                20                  25                  30

Lys Lys Lys Gly Lys Gly Leu Gly Lys Lys Arg Asp Pro Cys Leu Arg
                35                  40                  45

Lys Tyr Lys Asp Phe Cys Ile His Gly Glu Cys Lys Tyr Val Lys Glu
 50                  55                  60

Leu Arg Ala Pro Ser Cys Ile Cys His Pro Gly Tyr His Gly Glu Arg
 65                  70                  75                  80

Cys His Gly Leu Ser Leu
                85

<210> SEQ ID NO 4
<211> LENGTH: 76
<212> TYPE: PRT
<213> ORGANISM: Artificial Sequence
<220> FEATURE:
<223> OTHER INFORMATION: Synthetic construct

<400> SEQUENCE: 4

Arg Val Thr Leu Ser Ser Lys Pro Gln Ala Leu Ala Thr Pro Asn Lys
 1               5                  10                  15

Glu Glu His Gly Lys Arg Lys Lys Lys Gly Lys Gly Leu Gly Lys Lys
                20                  25                  30

Arg Asp Pro Cys Leu Arg Lys Tyr Lys Asp Phe Cys Ile His Gly Glu
                35                  40                  45
```

```
Cys Lys Tyr Val Lys Glu Leu Arg Ala Pro Ser Cys Ile Cys His Pro
 50                  55                  60
Gly Tyr His Gly Glu Arg Cys His Gly Leu Ser Leu
 65                  70                  75

<210> SEQ ID NO 5
<211> LENGTH: 75
<212> TYPE: PRT
<213> ORGANISM: Artificial Sequence
<220> FEATURE:
<223> OTHER INFORMATION: Synthetic construct

<400> SEQUENCE: 5

Val Thr Leu Ser Ser Lys Pro Gln Ala Leu Ala Thr Pro Asn Lys Glu
 1               5                  10                  15
Glu His Gly Lys Arg Lys Lys Lys Gly Lys Gly Leu Gly Lys Lys Arg
                 20                  25                  30
Asp Pro Cys Leu Arg Lys Tyr Lys Asp Phe Cys Ile His Gly Glu Cys
             35                  40                  45
Lys Tyr Val Lys Glu Leu Arg Ala Pro Ser Cys Ile Cys His Pro Gly
 50                  55                  60
Tyr His Gly Glu Arg Cys His Gly Leu Ser Leu
 65                  70                  75

<210> SEQ ID NO 6
<211> LENGTH: 30
<212> TYPE: DNA
<213> ORGANISM: Artificial Sequence
<220> FEATURE:
<223> OTHER INFORMATION: Synthetic DNA

<400> SEQUENCE: 6
tcaccatgga gttagtttgg gcagcagatc                                    30

<210> SEQ ID NO 7
<211> LENGTH: 30
<212> TYPE: DNA
<213> ORGANISM: Artificial Sequence
<220> FEATURE:
<223> OTHER INFORMATION: Synthetic DNA

<400> SEQUENCE: 7
gaagcacacg actgaggcac ctccagatgt                                    30

<210> SEQ ID NO 8
<211> LENGTH: 423
<212> TYPE: DNA
<213> ORGANISM: Mus musculus
<220> FEATURE:
<221> NAME/KEY: CDS
<222> LOCATION: (1)..(423)

<400> SEQUENCE: 8 atg gaa tgg atc tgg atc ttt ctc ttc atc ctg tca gga act gca ggt    48
Met Glu Trp Ile Trp Ile Phe Leu Phe Ile Leu Ser Gly Thr Ala Gly
 1               5                  10                  15 gtc cac tcc cag gtt cag ctg cag cag tct gga act gaa ctg gcg agg    96
Val His Ser Gln Val Gln Leu Gln Gln Ser Gly Thr Glu Leu Ala Arg
                 20                  25                  30 cct ggg gct tca gtg aag ctg tcc tgc aag gct tct gga tac acc ttc   144
Pro Gly Ala Ser Val Lys Leu Ser Cys Lys Ala Ser Gly Tyr Thr Phe
             35                  40                  45 aga acc tat ggt ata acc tgg gtg aag cag aga act gga cag ggc ctt   192
```

```
Arg Thr Tyr Gly Ile Thr Trp Val Lys Gln Arg Thr Gly Gln Gly Leu
    50                  55                  60 gag tgg att gga gag att ttt cct gga agt ggt aat act tac tac aat      240
Glu Trp Ile Gly Glu Ile Phe Pro Gly Ser Gly Asn Thr Tyr Tyr Asn
 65                  70                  75                  80 gag aag ttc aag ggc aag gcc tca ctg act gca gac aaa tcc tcc agc      288
Glu Lys Phe Lys Gly Lys Ala Ser Leu Thr Ala Asp Lys Ser Ser Ser
                 85                  90                  95 aca gcc tac atg cag ctc agc agc ctg aca tct gag gac tct gca gtc      336
Thr Ala Tyr Met Gln Leu Ser Ser Leu Thr Ser Glu Asp Ser Ala Val
            100                 105                 110 tat ttc tgt gca agg gag agc ttc tct gat ggt tac tac ggc tac ttt      384
Tyr Phe Cys Ala Arg Glu Ser Phe Ser Asp Gly Tyr Tyr Gly Tyr Phe
        115                 120                 125 gac tac tgg ggc caa ggc acc act ctc aca gtc tcc tca                  423
Asp Tyr Trp Gly Gln Gly Thr Thr Leu Thr Val Ser Ser
130                 135                 140

<210> SEQ ID NO 9
<211> LENGTH: 141
<212> TYPE: PRT
<213> ORGANISM: Mus musculus

<400> SEQUENCE: 9

Met Glu Trp Ile Trp Ile Phe Leu Phe Ile Leu Ser Gly Thr Ala Gly
 1               5                  10                  15

Val His Ser Gln Val Gln Leu Gln Gln Ser Gly Thr Glu Leu Ala Arg
                20                  25                  30

Pro Gly Ala Ser Val Lys Leu Ser Cys Lys Ala Ser Gly Tyr Thr Phe
            35                  40                  45

Arg Thr Tyr Gly Ile Thr Trp Val Lys Gln Arg Thr Gly Gln Gly Leu
    50                  55                  60

Glu Trp Ile Gly Glu Ile Phe Pro Gly Ser Gly Asn Thr Tyr Tyr Asn
 65                  70                  75                  80

Glu Lys Phe Lys Gly Lys Ala Ser Leu Thr Ala Asp Lys Ser Ser Ser
                 85                  90                  95

Thr Ala Tyr Met Gln Leu Ser Ser Leu Thr Ser Glu Asp Ser Ala Val
            100                 105                 110

Tyr Phe Cys Ala Arg Glu Ser Phe Ser Asp Gly Tyr Tyr Gly Tyr Phe
        115                 120                 125

Asp Tyr Trp Gly Gln Gly Thr Thr Leu Thr Val Ser Ser
130                 135                 140

<210> SEQ ID NO 10
<211> LENGTH: 399
<212> TYPE: DNA
<213> ORGANISM: Mus musculus
<220> FEATURE:
<221> NAME/KEY: CDS
<222> LOCATION: (1)..(399)

<400> SEQUENCE: 10 atg gat tca cag gcc cag gtt ctt atg tta ctg ctg cta tgg gta tct       48
Met Asp Ser Gln Ala Gln Val Leu Met Leu Leu Leu Leu Trp Val Ser
 1               5                  10                  15 ggt acc tgt ggg gac att gtg atg tca cag tct cca tcc tcc cta gct       96
Gly Thr Cys Gly Asp Ile Val Met Ser Gln Ser Pro Ser Ser Leu Ala
                20                  25                  30 gtg tca gtt gga gag aag gtt act atg agc tgc aag tcc agt cag agc      144
Val Ser Val Gly Glu Lys Val Thr Met Ser Cys Lys Ser Ser Gln Ser
```

```
                35                  40                  45
ctt tta tat agt acc aat caa aag aac tcc ttg gcc tgg tac cag cag    192
Leu Leu Tyr Ser Thr Asn Gln Lys Asn Ser Leu Ala Trp Tyr Gln Gln
    50                  55                  60 aaa cca ggg cag tct cct aaa ctg ctg att tac tgg gca tcc act agg    240
Lys Pro Gly Gln Ser Pro Lys Leu Leu Ile Tyr Trp Ala Ser Thr Arg
65                  70                  75                  80 gaa tct ggg gtc cct gat cgc ttc aca ggc agt gga tct ggg aca gat    288
Glu Ser Gly Val Pro Asp Arg Phe Thr Gly Ser Gly Ser Gly Thr Asp
                85                  90                  95 ttc act ctc acc atc agc agt gtg aag gct gaa gac ctg gca gtt tat    336
Phe Thr Leu Thr Ile Ser Ser Val Lys Ala Glu Asp Leu Ala Val Tyr
            100                 105                 110 tac tgt cag caa tat tat agg tat ccg ctc acg ttc ggt gct ggg acc    384
Tyr Cys Gln Gln Tyr Tyr Arg Tyr Pro Leu Thr Phe Gly Ala Gly Thr
        115                 120                 125 aag ctg gag ctg aaa                                                399
Lys Leu Glu Leu Lys
    130

<210> SEQ ID NO 11
<211> LENGTH: 133
<212> TYPE: PRT
<213> ORGANISM: Mus musculus

<400> SEQUENCE: 11

Met Asp Ser Gln Ala Gln Val Leu Met Leu Leu Leu Leu Trp Val Ser
1               5                   10                  15

Gly Thr Cys Gly Asp Ile Val Met Ser Gln Ser Pro Ser Ser Leu Ala
            20                  25                  30

Val Ser Val Gly Glu Lys Val Thr Met Ser Cys Lys Ser Ser Gln Ser
        35                  40                  45

Leu Leu Tyr Ser Thr Asn Gln Lys Asn Ser Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Lys Ala Glu Asp Leu Ala Val Tyr
            100                 105                 110

Tyr Cys Gln Gln Tyr Tyr Arg Tyr Pro Leu Thr Phe Gly Ala Gly Thr
        115                 120                 125

Lys Leu Glu Leu Lys
    130

<210> SEQ ID NO 12
<211> LENGTH: 5
<212> TYPE: PRT
<213> ORGANISM: Mus musculus

<400> SEQUENCE: 12

Thr Tyr Gly Ile Thr
1               5

<210> SEQ ID NO 13
<211> LENGTH: 17
<212> TYPE: PRT
<213> ORGANISM: Mus musculus

<400> SEQUENCE: 13
```

Glu Ile Phe Pro Gly Ser Gly Asn Thr Tyr Tyr Asn Glu Lys Phe Lys
1               5                   10                  15

Gly

<210> SEQ ID NO 14
<211> LENGTH: 13
<212> TYPE: PRT
<213> ORGANISM: Mus musculus

<400> SEQUENCE: 14

Glu Ser Phe Ser Asp Gly Tyr Tyr Gly Tyr Phe Asp Tyr
1               5                   10

<210> SEQ ID NO 15
<211> LENGTH: 17
<212> TYPE: PRT
<213> ORGANISM: Mus musculus

<400> SEQUENCE: 15

Lys Ser Ser Gln Ser Leu Leu Tyr Ser Thr Asn Gln Lys Asn Ser Leu
1               5                   10                  15

Ala

<210> SEQ ID NO 16
<211> LENGTH: 7
<212> TYPE: PRT
<213> ORGANISM: Mus musculus

<400> SEQUENCE: 16

Trp Ala Ser Thr Arg Glu Ser
1               5

<210> SEQ ID NO 17
<211> LENGTH: 9
<212> TYPE: PRT
<213> ORGANISM: Mus musculus

<400> SEQUENCE: 17

Gln Gln Tyr Tyr Arg Tyr Pro Leu Thr
1               5

<210> SEQ ID NO 18
<211> LENGTH: 48
<212> TYPE: DNA
<213> ORGANISM: Artificial Sequence
<220> FEATURE:
<223> OTHER INFORMATION: Synthetic DNA

<400> SEQUENCE: 18
aaggaaaaaa gcggccgctg aacacactga ctctaaccat ggaatgga                    48

<210> SEQ ID NO 19
<211> LENGTH: 44
<212> TYPE: DNA
<213> ORGANISM: Artificial Sequence
<220> FEATURE:
<223> OTHER INFORMATION: Synthetic DNA

<400> SEQUENCE: 19
cgatgggccc ttggtggagg ctgaggagac tgtgagagtg gtgc                        44

<210> SEQ ID NO 20
<211> LENGTH: 34

<212> TYPE: DNA
<213> ORGANISM: Artificial Sequence
<220> FEATURE:
<223> OTHER INFORMATION: Synthetic DNA

<400> SEQUENCE: 20
ccggaattca gacaggcagg ggaagcaaga tgga                            34

<210> SEQ ID NO 21
<211> LENGTH: 40
<212> TYPE: DNA
<213> ORGANISM: Artificial Sequence
<220> FEATURE:
<223> OTHER INFORMATION: Synthetic DNA

<400> SEQUENCE: 21
agccaccgta cgtttcagct ccagcttggt cccagcaccg                      40

<210> SEQ ID NO 22
<211> LENGTH: 122
<212> TYPE: PRT
<213> ORGANISM: Artificial Sequence
<220> FEATURE:
<223> OTHER INFORMATION: Synthetic construct

<400> SEQUENCE: 22

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Thr Tyr
            20                  25                  30

Gly Ile Thr Trp Val Arg Gln Ala Pro Gly Gln Gly Leu Glu Trp Met
        35                  40                  45

Gly Glu Ile Phe Pro Gly Ser Gly Asn Thr Tyr Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ser Phe Ser Asp Gly Tyr Tyr Gly Tyr Phe Asp Tyr Trp
            100                 105                 110

Gly Gln Gly Thr Leu Val Thr Val Ser Ser
        115                 120

<210> SEQ ID NO 23
<211> LENGTH: 113
<212> TYPE: PRT
<213> ORGANISM: Artificial Sequence
<220> FEATURE:
<223> OTHER INFORMATION: Synthetic construct

<400> SEQUENCE: 23

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Leu Leu Tyr Ser
            20                  25                  30

Thr Asn Gln Lys Asn Ser Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

```
Ile Ser Ser Leu Gln Ala Glu Asp Val Ala Val Tyr Tyr Cys Gln Gln
            85                  90                  95

Tyr Tyr Arg Tyr Pro Leu Thr Phe Gly Gln Gly Thr Lys Leu Glu Ile
        100                 105                 110

Lys

<210> SEQ ID NO 24
<211> LENGTH: 160
<212> TYPE: DNA
<213> ORGANISM: Artificial Sequence
<220> FEATURE:
<223> OTHER INFORMATION: Synthetic DNA

<400> SEQUENCE: 24
aattaaccct cactaaaggg atccgcggcc gcgacccctc accatgaacc tcgggctcag    60
tttgattttc cttgccctca ttttaaaagg tgtccagtgt caggtgcagc tggtgcagtc   120
tggggctgag gtgaagaagc ctggggcctc agtgaaggtc                        160

<210> SEQ ID NO 25
<211> LENGTH: 153
<212> TYPE: DNA
<213> ORGANISM: Artificial Sequence
<220> FEATURE:
<223> OTHER INFORMATION: Synthetic DNA

<400> SEQUENCE: 25
ggtgttgccg agccaggaa aaatctcccc catccactca gcccttgtc caggggcctg      60 tcgcacccag gtaatgccgt aggtggtaaa ggtgtaacca aagccttgc aggagacctt   120 cactgaggcc ccaggcttct tcacctcagc ccc                              153

<210> SEQ ID NO 26
<211> LENGTH: 156
<212> TYPE: DNA
<213> ORGANISM: Artificial Sequence
<220> FEATURE:
<223> OTHER INFORMATION: Synthetic DNA

<400> SEQUENCE: 26
gagtggatgg gggagatttt tcctggctcc ggcaacacct attataacga aaagttcaag    60
gggcgggtca ccattaccgc cgacaagtcc acgagcacag cctacatgga gctgagcagc   120
ctgcggtctg aggacacggc cgtgtattac tgtgcg                           156

<210> SEQ ID NO 27
<211> LENGTH: 158
<212> TYPE: DNA
<213> ORGANISM: Artificial Sequence
<220> FEATURE:
<223> OTHER INFORMATION: Synthetic DNA

<400> SEQUENCE: 27
gtaatacgac tcactatagg gcaagcttgg gcccttggtg gaggctgagg agacggtgac    60
cagggtcccc tggccccagt agtcgaagta cccgtagtac ccgtcgctga agctctcgcg   120
cgcacagtaa tacacggccg tgtcctcaga ccgcaggc                         158

<210> SEQ ID NO 28
<211> LENGTH: 163
<212> TYPE: DNA
<213> ORGANISM: Artificial Sequence
<220> FEATURE:
```

```
-continued

<223> OTHER INFORMATION: Synthetic DNA

<400> SEQUENCE: 28
aattaaccct cactaaaggg ggatccgaat tcgcctcttc aaaatgaagt tgcctgttag      60
gctgttggtg ctgatgttct ggattcctgc ttccagcagt gacatcgtga tgacccagtc    120
tccagactcc ctggctgtgt ctctgggcga gagggccacc atc                      163

<210> SEQ ID NO 29
<211> LENGTH: 157
<212> TYPE: DNA
<213> ORGANISM: Artificial Sequence
<220> FEATURE:
<223> OTHER INFORMATION: Synthetic DNA

<400> SEQUENCE: 29
cccgcgtgct ggcccagtaa atgagcagct taggaggctg ccctggtttc tgctggtacc     60
aggccaggct gttcttctgg ttggtgctgt acagcaggct ctggctgctc ttgcagttga    120
tggtggccct ctcgcccaga gacacagcca gggagtc                             157

<210> SEQ ID NO 30
<211> LENGTH: 147
<212> TYPE: DNA
<213> ORGANISM: Artificial Sequence
<220> FEATURE:
<223> OTHER INFORMATION: Synthetic DNA

<400> SEQUENCE: 30
cagcctccta agctgctcat ttactgggcc agcacgcggg agagcggggt ccccgaccga     60
ttcagtggca gcgggtctgg gacagatttc actctcacca tcagcagcct gcaggctgaa    120
gatgtggcag tttattactg tcagcag                                        147

<210> SEQ ID NO 31
<211> LENGTH: 126
<212> TYPE: DNA
<213> ORGANISM: Artificial Sequence
<220> FEATURE:
<223> OTHER INFORMATION: Synthetic DNA

<400> SEQUENCE: 31
gtaatacgac tcactatagg gcaagcttcg tacgtttgat ttccagcttg gtccttggc      60 cgaaggtcag cgggtaccgg tagtactgct gacagtaata aactgccaca tcttcagcct    120
gcaggc                                                               126
```

MONOCLONAL ANTIBODY CAPABLE OF BINDING TO HEPARIN-BINDING EPIDERMAL GROWTH FACTOR-LIKE GROWTH FACTOR

CROSS-REFERENCE TO RELATED APPLICATION

This application is a Continuation of PCT/JP2007/061487, filed Jun. 6, 2007, which claims priority to Japan Patent 2006-157279, filed Jun. 6, 2006.

TECHNICAL FIELD

The present invention relates to a monoclonal antibody or an antibody fragment thereof which binds to a cell membrane-bound heparin binding epidermal growth factor-like growth factor (hereinafter referred to as "HB-EGF"), a membrane type HB-EGF and a secretory HB-EGF.

BACKGROUND ART

HB-EGF was isolated and purified by Higashiyama et al, in 1992 from a culture supernatant of a macrophage-differentiated human macrophage-like cell line U-937 (Non-patent document 1). HB-EGF holds 6 cysteine residues in common preserved in the epidermal growth factor (EGF) family and belongs to the EGF family, and is synthesized as a type I membrane protein similar to the case of other proteins belonging to the EGF family (Non-patent documents 1 and 2). The membrane type HB-EGF is converted into a secretory HB-EGF of 14 to 22 kilo daltons (hereinafter referred to as "kDa") by a metalloprotease activated by various physiological stimuli such as stress due to heat or osmotic pressure, a growth factor, a cytokine and lysophosphatidic acid (LPA) which is a G protein coupled receptor (GPCR) (Non-patent documents 1 to 3). The secretory HG-EGF binds to an EGF receptor (EGFP/ErbB1) (Non-patent document 1), ErbB4 (Non-patent document 4) and N-arginine dibasic convertase (Non-patent document 5), and has the growth acceleration activity for fibroblasts and smooth muscle cells (Non-patent document 1), keratinocyte (Non-patent document 6), hepatocyte (Non-patent document 7) and mesangial cell (Non-patent document 8). In addition, it is also known that HB-EGF is related to organogenesis of, for example, cardiac valve (Non-patent documents 28, 29 and 31), healing of wound (Non-patent documents 9 and 10), hyperplasia of smooth muscle cell caused in atherosclerosis (Non-patent document 11), re-stricture (Non-patent documents 12 and 13), pulmonary hypertension (Non-patent document 14), hepatic regeneration (Non-patent document 15), cerebral disorder (Non-patent document 16) and cancer (Non-patent documents 28 to 35).

On the other hand, it has been reported that a considerable amount of membrane type HB-EGF is expressed on the cell surface without being digested into its secretory (Non-patent document 17). It is known that the membrane type HB-EGF forms a complex on the cell surface with CD9 or the like tetra tetraspanin or integrin α3β1, and it has been reported also that it interacts as a juxtacrine growth factor with adjacent cells (Non-patent documents 17 to 22). In addition, Naglich et al. have reported that the membrane type HB-EGF functions as receptor of diphtheria toxin and is related to the internalization of diphtheria toxin into cells (Non-patent document 23).

When Mekada et al. have analyzed physiological functions of HB-EGF by preparing HB-EGF knockout (KO) mice, the HB-EGF KO mice showed dilation of ventricle, lowering of cardiac function and a symptom of cardiac valve hypertrophy and more than half of the animals died in several days after birth. This fact shows that HB-EGF is a protein essential for the development and functional maintenance of the heart (Non-patent document 24).

Next, Mekada et al. have prepared two genes for an HB-EGF which became unable to be converted into secretory due to introduction of a mutation into a protease digestion site (hereinafter referred to as "HB$^{uc}$") and an HB-EGF which lacks a transmembrane region, is secreted and is secreted independently of protease digestion (hereinafter referred to as "HB$^{\Delta tm}$"). By preparing transgenic mice which express respective HB-EGF mutants, physiological functions of membrane type and secretory HB-EGFs were analyzed (Non-patent document 25). As a result, since the HB$^{uc}$ expressing mice showed symptoms similar to those of the HB-EGF KO mice, it was considered that the secretory HB-EGF is functioning as the active type protein. Most of the HB$^{\Delta tm}$ expressing mice died before the neonatal stage or at the neonatal stage. In addition, hyperplasia of keratinocyte and ventricular hypertrophy from the neonatal stage were found in HB$^{\Delta tm/+}$ expressing mice in which a mutation was introduced into only one of the alleles. These symptoms were phenotypes directly opposite to those of the HB-EGF KO mice and HB$^{uc}$ mice. CRM197 known as a mutant of diphtheria toxin (Non-patent document 26) specifically inhibits cell growth acceleration activity of HB-EGF and does not permeate cell membrane. Since this CRM197 inhibited hyperplasia and ventricular hypertrophy as phenotypes of the HB$^{\Delta tm}$ expressing mice, it is considered that the HB$^{\Delta tm}$ formed in the HB$^{\Delta tm}$ expression mice does not act by binding to its intracellular receptor before its secretion, but acts by binding to the receptor on the cell surface after secreted extracellularly. Accordingly, the quantitative balance between membrane type HB-EGF and secretory HB-EGF in the living body is essential for the maintenance of normal physiological functions, and it is considered that the process for converting from membrane type into secretory of HB-EGF is controlled in the living body.

Higashiyama at al. have found that secretory HB-EGF protein in the heart is increased in the heart of a mouse in which cardiac hypertrophy was induced by constricting the thoracic aorta. It has been reported that when a low molecular weight compound capable of inhibiting a protease which converts membrane type HB-EGF into secretory is administered to this mouse, cardiac hypertrophy is suppressed as a result of suppressing conversion of the membrane type HB-EGF into secretory in the heart (Non-patent document 27).

It has been reported so far that HB-EGF is expressed at a high level in various cancers such as beast cancer, liver cancer, pancreas cancer and bladder cancer, in comparison with normal tissues (Non-patent documents 28 to 31). Also, it has been recently found that HB-EGF is an important factor for the proliferation of cancer (Non-patent documents 32 and 33). Mekada et al. have found that a significant tumor growth inhibitory effect is recognized when small interference RNA (siRNA) of HB-EGF is introduced into a cancer cell line, or CRM197 is administered to a mouse into which the cancer cell line was transplanted, in a model system in which a human ovarian cancer cell line is transplanted into a nude mouse. Also, Higashiyama et al. have found that cell growth, colony forming ability, vascular endothelial growth factor (VEGF) expression and expression of cyclin D1 and the like are increased in vitro in a bladder cancer cell line into which the HB-EGF gene was transferred. In addition, it was reported that increase of tumorigenicity and increase of tumor angiogenesis are found also in vivo. Such a growth stimulation activity was found only when the membrane type HB-EGF gene or secretory HB-EGF gene was expressed, but was nor found when a protease-resistant membrane type HB-EGF gene was forcedly expressed. Accordingly, a possibility was suggested that the secretory HB-EGF is an important factor which is related to the tumor growth of ovarian cancer and bladder cancer. Regarding the expression of HB-EGF in clinical patients, Mekada et al. have analyzed expression quantity of HB-EGF mRNA and concentration of secretory HB-EGF in the tumor tissues and ascites of ovarian cancer patients, and reported that only HB-EGF among the EGF family is expressed (Non-patent document 32). In addition, Miyamoto et al. have reported that prognosis is poorer in ovarian cancer patients in which HB-EGF mRNA of the tumor is highly expressed, than low expression patients (Non-patent document 34). The above results show that at least in the ovarian cancer, the secretory HB-EGF produced by the cancer is related to the cancer growth by the autocrine or paracrine mechanism (Non-patent document 35). As antibodies which bind to secretory HB-EGF and inhibit its activity, some polyclonal antibodies and one monoclonal antibody (all manufactured by R & D) are known. It has been reported that an anti-HB-EGF goat polyclonal antibody (manufactured by R & D) binds to the cell surface membrane type HB-EGF expressed in COS-7 cell (Non-patent document 3). It is broadly known that when a membrane protein is present on the surface of a cell such as cancer, a monoclonal antibody which binds to such a protein could become a therapeutic agent which inhibits growth of the cell (Non-patent document 36). However, there are no reports to date for monoclonal antibodies which bind to a secretory HB-EGF, a cell membrane-bound HB-EGF and a membrane type HB-EGF.

Non-patent document 1: *Science*, Vol. 251, 936, 1991

Non-patent document 2: *J. Biol. Chem.* 267 (1992) 6205-6212

Non-patent document 3: *Nature*, Vol. 402, 884, 1999

Non-patent document 4: *EMBO J.* 16 (1997) 1268-1278

Non-patent document 5: *EMBO J.* 20 (2001) 3342-3350

Non-patent document 6: *J. Biol. Chem.* 269 (1994) 20060-20066

Non-patent document 7: *Biochem Biophys. Res. Commun.* 198 (1994) 25-31

Non-patent document 8: *J. Pathol.* 189 (1999) 431-438

Non-patent document 9: *Proc. Natl. Acad. Sci. U.S.A.* 90 (1993) 3889-3893

Non-patent document 10: *J. Cell Biol.* 151 (2000) 209-219

Non-patent document 11: *J. Clin. Invest.*, 95, 404, 1995

Non-patent document 12: *Arterioscler. Thromb. Vasc. Biol.* 16 (1996) 1524-1531

Non-patent document 13: *J. Biol. Chem.* 277 (2002) 37487-37491

Non-patent document 14: *Am. J. Pathol.* 143 (1993) 784-793

Non-patent document 15: *Hepatology* 22 (1995) 1584-1590

Non-patent document 16: *Brain Res*, 827 (1999) 130-138

Non-patent document 17: *Biochem. Biophys. Acta.*, Vol. 1333, F179, 1997

Non-patent document 18: *J. Cell Biol.* 128 (1995) 929-938

Non-patent document 19: *J. Cell Biol.* 129 (1995) 1691-1705

Non-patent document 20: *Cytokine Growth Factor Rev.*, Vol. 11, 335, 2000

Non-patent document 21: *Int. J. Cancer*, Vol. 98, 505, 2002

Non-patent document 22: *J. Histochem. Cytochem.*, Vol. 49, 439, 2001

Non-patent document 23: *Cell*, Vol. 69, 1051, 1992

Non-patent document 24: *PNAS*, Vol. 100, 3221, 2003

Non-patent document 25: *J. of Cell Biology*, Vol. 163, 469, 2003

Non-patent document 26: *J. Biol. Chem.*, Vol. 270, 1015, 1995

Non-patent document 27: *Nat. Med.*, Vol. 8, 35, 2002

Non-patent document 28: *Breast Cancer Res. Treat.*, Vol. 67, 81, 2001

Non-patent document 29: *Oncol. Rep.*, Vol. 8, 903, 2001

Non-patent document 30: *Biochem. Biophys. Res. Commun.*, Vol. 202, 1705, 1994

Non-patent document 31: *Cancer Res.*, Vol. 61, 6227, 2001

Non-patent document 32: *Cancer Res.*, Vol. 64, 5720, 2004

Non-patent document 33: *Cancer Res.*, Vol. 64, 5283, 2004

Non-patent document 34: *Clin. Cancer Res.*, Vol. 11, 4783, 2005

Non-patent document 35: *Clin. Cancer Res.*, Vol. 11, 4639, 2005

Non-patent document 36: *Nat. Rev. Drug. Discov.*, Vol. 2, 52-62, 2003

DISCLOSURE OF THE INVENTION

Problems to be Solved by the Invention

Medicaments for treating diseases relating to HB-EGF are in demand.

Means to Solve the Problems

The present invention relates to the following (1) to (24):

(1) A monoclonal antibody or an antibody fragment thereof which binds to a cell membrane-bound heparin binding epidermal growth factor-like growth factor (hereinafter referred to as "HB-EGF"), a membrane type HB-EGF and a secretory HB-EGF.

(2) The monoclonal antibody or the antibody fragment thereof according to (1), which binds to epidermal growth factor-like domain (EGF-like domain) of the cell membrane-bound HB-EGF, the membrane type HB-EGF and the secretory HB-EGF.

(3) The monoclonal antibody or the antibody fragment thereof according to (1) or (2), which inhibits binding of the secretory HB-EGF and an HB-EGF receptor.

(4) The monoclonal antibody or the antibody fragment thereof according to any one of (1) to (3), which has neutralizing activity for the secretory HB-EGF.

(5) The monoclonal antibody or the antibody thereof according to any one of (1) to (4), which binds to a binding region of the secretory HB-EGF and an HB-EGF receptor or diphtheria toxin.

(6) The monoclonal antibody or the antibody thereof according to any one of (1) to (5), which binds to an epitope comprising at least one of amino acids at positions 133, 135 and 147 in the amino acid sequence represented by SEQ ID NO:2.

(7) The monoclonal antibody or the antibody fragment thereof according to (6), which binds to an epitope comprising amino acids at positions 133, 135 and 147 in the amino acid sequence represented by SEQ ID NO:2.

(8) The monoclonal antibody or the antibody fragment thereof according to any one of (1) to (5), which binds to an epitope comprising the amino acid at position 141 in the amino acid sequence represented by SEQ ID NO:2.

(9) The monoclonal antibody or the antibody fragment thereof according to any one of (1) to (3), (5) and (8), which binds to an epitope to which a monoclonal antibody produced by hybridoma KM3579 (FERM BP-10491) binds.

(10) The monoclonal antibody or the antibody fragment according to any one of (1) to (7), which binds to an epitope to which a monoclonal antibody produced by hybridoma KM3567 (PERM BP-10573) binds.

(11) The monoclonal antibody or the antibody fragment according to any one of (1) to (7), which binds to an epitope to which a monoclonal antibody produced by hybridoma KM3566 (FERM BP-10490) binds.

(12) The monoclonal antibody or the antibody fragment according to any one of (1) to (7) and (11), wherein CDR (complementarity determining region, hereinafter referred to "CDR") 1, CDR2 and CDR3 of a heavy chain variable region (hereinafter referred to "VH") of an antibody comprise amino acid sequences represented by SEQ ID NOs:12, 13 and 14, respectively, and CDR1, CDR2 and CDR3 of a light chain variable region (hereinafter referred to as "VL") of an antibody comprise amino acid sequence represented by SEQ ID NOs:15, 16 and 17, respectively.

(13) The antibody or the antibody fragment thereof according to any one of (1) to (12), wherein the monoclonal antibody is a recombinant antibody.

(14) The antibody or the antibody fragment thereof according to (13), wherein the recombinant antibody is selected from a human chimeric antibody, a humanized antibody and a human antibody.

(15) The human chimeric antibody or the antibody fragment thereof according to (14), wherein VH of the human chimeric antibody comprises the amino acid sequence represented by SEQ ID NO:9, and VL of the human chimeric antibody comprises the amino acid sequence represented by SEQ ID NO:11.

(16) The human chimeric antibody or the antibody fragment thereof according to (14), wherein VH of the humanized antibody comprises the amino acid sequence represented by SEQ ID NO:22 or an amino acid sequence in which at least one modification selected from substitutions of Ala at position 9 with Thr, Val at position 20 with Leu, Thr at position 30 with Arg, Arg at position 38 with Lys, Pro at position 41 with Thr, Met at position 48 with Ile, Arg at position 67 with Lys, Val at position 68 with Ala, Ile at position 70 with Leu, Tyr at position 95 with Phe, and Val at position 118 with Leu in the amino acid sequence represented by SEQ ID NO:22; and wherein VL of the humanized antibody comprises the amino acid sequence represented by SEQ ID NO:23 or an amino acid sequence in which at least one modification selected from substitutions of Leu at position 15 with Val, Ala at position 19 with Val, Ile at position 21 with Met, Pro at position 49 with Ser, and Leu at position 84 with Val.

(17) The antibody fragment according to any one of (1) to (16), which is selected from Fab, Fab', F(ab')$_2$, a single chain antibody (scFv), a dimerized V region (diabody), a disulfide stabilized V region (dsFv), and a peptide comprising CDRs.

(18) A DNA encoding the antibody or the antibody fragment thereof according to any one of (1) to (17).

(19) A recombinant vector comprising the DNA according to (18).

(20) A transformant obtainable by introducing the recombinant vector according to (19) into a host cell.

(21) A process for producing the antibody or the antibody fragment thereof according to any one of (1) to (17), which comprises culturing the transformant according to (20) in a medium to form and accumulate the antibody or the antibody fragment according to any one of (1) to (17) in the culture, and recovering the antibody or the antibody fragment from the culture.

(22) A pharmaceutical composition comprising the antibody or the antibody fragment thereof according to any one of (1) to (17) as active ingredient.

(23) An agent for treating a disease relating to HB-EGF, comprising the antibody or the antibody fragment thereof according to any one of (1) to (17) as an active ingredient.

(24) The agent according to (23), wherein the disease relating to HB-EGF is cancer.

EFFECT OF THE INVENTION

The present invention provides a monoclonal antibody or an antibody fragment thereof which binds to a cell membrane-bound heparin binding epidermal growth factor-like growth factor (hereinafter referred to as "HB-EGF"), a membrane type H-EGF and a secretory HB-EGF.

BEST MODE FOR CARRYING OUT THE INVENTION

Figure 1A:
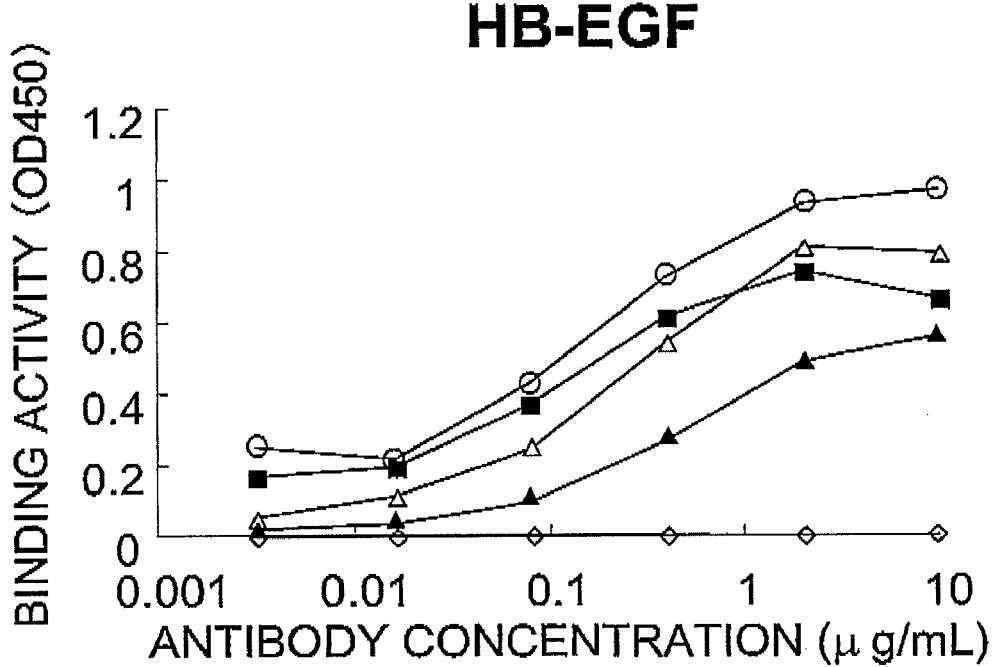
FIG. 1A shows the reactivity of various anti-HB-EGF monoclonal antibodies by binding ELISA. The abscissa shows the concentration of each antibody, and the ordinate shows the binding activity of each antibody. ◊ shows monoclonal antibody KM511, ■ shows monoclonal antibody KM3566, Δ shows monoclonal antibody KM3567, ▲ shows monoclonal antibody KM3579, and ○ shows monoclonal antibody MAB259.
Figure 1A:
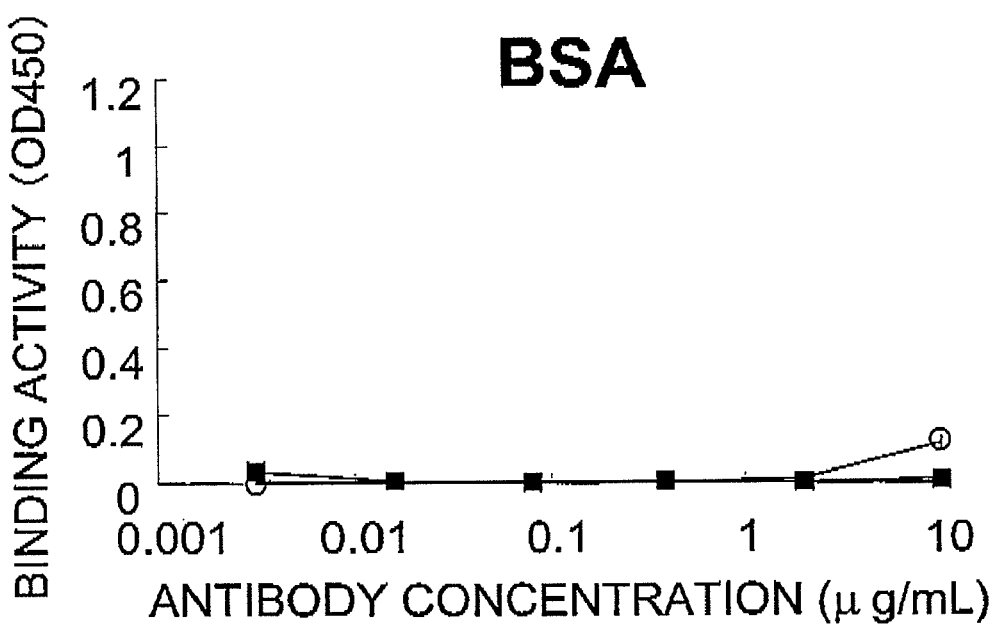

In the present invention, the membrane type HB-EGF is HB-EGF which binds to a cell membrane through a cell membrane-spanning domain and consists of a signal sequence, a pro-region, a heparin-binding region, an EGF-like domain, a juxtamembrane domain and a cytoplasmic domain. Specifically, it includes a polypeptide comprising the amino acid sequence represented by SEQ ID NO:2. Also, in the present invention, the secretory HB-EGF is an extracellular domain comprising an EGF-like domain in which the membrane-binding region of the membrane type HB-EGF is cleaved by a protease or the like. Specifically, it includes a polypeptide comprising the amino acid sequence represented by SEQ ID NO:3. The cell membrane-bound HB-EGF is HB-EGF in which the secretory HB-EGF is bound to the surface of a cell membrane by its haparin-binding activity, electrostatically binding activity or the Like.

The substance bound to the secretory HB-EGF on the cell membrane may be any substance, so long as it is capable of binding to the secretory HB-EGF on the cell membrane. Specifically, it includes polysaccharides, preferably glycosaminoglycan, and more preferably heparan sulfate.

HB-EGF has activity of binding to diphtheria toxin or EGF receptor ErbB1 or ErbB4.

The membrane type HB-EGF includes proteins of the following (a), (b) and (c), and the like:

(a) a protein comprising the amino acid sequence represented by SEQ ID NO:2;

(b) a protein consisting of an amino acid sequence in which one or more amino acids are deleted, substituted, inserted and/or added in the amino acid sequence represented by SEQ ID NO:2, and having activity of binding to diphteria toxin;

(c) a protein consisting of an amino acid sequence having 80% or more homology with the amino acid sequence represented by SEQ ID NO:2, and having activity of binding to diphteria toxin.

Also, the secretory HB-EGF includes proteins of the following (a), (b) and (c), and the like:

(a) a protein comprising the amino acid sequence represented by SEQ ID NO:3, 4 or 5;

(b) a protein consisting of an amino acid sequence in which one or more amino acids are deleted, substituted, inserted and/or added in the amino acid sequence in the amino acid sequence represented by SEQ ID NO:3, 4 or 5, and having activity of binding to EGF receptor ErbB1 or ErbB4;

(c) a protein consisting of an amino acid sequence having 80% or more homology with the amino acid sequence represented by SEQ ID NO:3, 4 or 5, and having activity of binding to EGF receptor ErbB1 or ErbB4.

In the present invention, the protein consisting of an amino acid sequence wherein one or more amino acids are deleted, substituted, inserted and/or added in the amino acid sequence represented by any one of SEQ ID NOs:2, 3, 4 or 5 and having activity of binding to diphteria toxin or EGF receptor ErbB1 or ErbB4, for example, by introducing a site-directed mutation into DNA encoding the protein having the amino acid sequence represented by any one of SEQ ID NO:2, 3, 4 or 5 by site-directed mutagenesis described in *Molecular Cloning*, Second Edition, *Current Protocols in Molecular Biology* (1987-1997), *Nucleic Acids Research*, 10, 6487 (1982), *Proc. Natl. Acad. Sci., USA*, 79, 6409 (1982), *Gene*, 34, 315 (1985), *Nucleic Acids Research*, 13, 4431 (1985), *Proc. Natl. Acad Sci USA*, 82, 488 (1985), or the like. The number of amino acid residues which are deleted, substituted, inserted and/or added is one or more, and is not specifically limited, but it is within the range where deletion, substitution, insertion or addition is possible by known methods such as the above site-directed mutagenesis. The suitable number is 1 to dozens, preferably 1 to 20, more preferably 1 to 10, and most preferably 1 to 5.

Also, the protein having 80% or more homology to the amino acid sequence represented by SEQ ID NO:2, 3, 4 or 5 and having activity of binding to diphteria toxin or EGR receptor ErbB1 or ErbB4 is a protein having at least 80% or more homology, preferably 85% or more homology, more preferably 90% or more homology, further preferably 95% or more homology, particularly preferably 97% or more homology, and most preferably 99% or more homology to the amino acid sequence represented by any one of SEQ ID NO:2, 3, 4 or 5, and having activity of binding to diphteria toxin or EGR receptor ErbB1 or ErbB4.

The number of the homology described in the present invention may be a known number calculated by using a known homology search program, unless otherwise indicated. Regarding the nucleotide sequence, the number may be calculated by using a default parameter in BLAST [*J. Mol. Biol.*, 215, 403 (1990)] or the like, and regarding the amino acid sequence, the number may be calculated by using a default parameter in BLAST2 [*Nucleic Acids Res.*, 25, 3389 (1997)], *Genome Res.*, 7, 649 (1997) or internet accessible publicly available BLAST software.ncbi.nlm.nih.go v/Education/BLASTinfo/information3.html. As the default parameter, G (cost to open gap) is 5 for the nucleotide sequence and 11 for the amino acid sequence; –E (cost to extend gap) is 2 for the nucleotide sequence and 1 for the amino acid sequence; –q (penalty for nucleotide mismatch) is –3; –r (reward for nucleotide match) is 1; –e (expect value) is 10; –W (wordsize) is 11 residues for the nucleotide sequence and 3 residues for the amino acid sequence; –y (dropoff (X) for blast extensions in bits) is 20 for blastn and 25 for a program other than blastn ncbi.nlm.nih.gov/blast/html/blastcgihelp.html). Also, the analysis software for amino acid sequence includes FASTA [*Methods in Enzymology*, 183, 63 (1990)] and the like.

The antibody of the present invention includes a monoclonal antibody which binds to a cell membrane-bound HB-EGF, a membrane type HB-EGF and a secretory HB-EGF and is capable of binding to epidermal growth factor-like domain (EGF-like domain) of the cell membrane-bound HB-EGF, the membrane type HB-EGF and the secretory HB-EGF.

The EGF-like domain includes, for example, a polypeptide comprising the amino acid sequence represented by SEQ ID NO:4 or 5, and the like.

The monoclonal antibody which binds to the EGF-like domain includes a monoclonal antibody which inhibits binding of a secretory HB-EGF and an HB-EGF receptor.

The monoclonal antibody which inhibits binding of a secretory HB-EGF and an HB-EGF receptor includes a monoclonal antibody which binds to the binding region of a secretory HB-EGF and an HB-EGF receptor or diphtheria toxin, and the like.

The antibody of the present invention includes an antibody having neutralizing activity for a secretory HB-EGF. In the present invention, the neutralizing activity is activity which inhibits biological activity of a secretory HB-EGF, and includes, for example, activity which inhibits cell growth of a cell expressing an HB-EGF receptor, and the like.

Examples of the antibody of the present invention include a monoclonal antibody which binds to an epitope including at least one amino acid among amino acids at positions 115 to 147, preferably a monoclonal antibody which binds to an epitope containing at least one amino acid among amino acids at positions 133 to 147, more preferably a monoclonal antibody which binds to an epitope containing at least one amino acid among amino acids at positions 115, 122, 124, 125, 127, 129, 133, 135, 141 and 147, still more preferably a monoclonal antibody which binds to an epitope containing at least amino acids at positions 133 and 135 among amino acids at positions 133, 135 and 147, and most preferably a monoclonal antibody which binds to an epitope containing amino acids at positions 133, 135 and 147, in the polypeptide having the amino acid sequence represented by SEQ ID NO:2, and the like.

Furthermore, examples of the antibody of the present invention include a monoclonal antibody which binds to an epitope to which a monoclonal antibody produced by hybridoma KM3566 (FERM BP-10490), a monoclonal antibody produced by hybridoma KM3567 (FERM BP-10573) or a monoclonal antibody produced by hybridoma KM3579 (FERM BP-10491) binds.

Examples of the antibody having neutralizing activity include a monoclonal antibody which binds to an epitope containing amino acids at positions 133, 135 and 147 in the polypeptide having the amino acid sequence represented by SEQ ID NO:2.

The monoclonal antibody of the present invention includes an antibody produced by a hybridoma, a recombinant antibody and the like.

A hybridoma is a cell producing a monoclonal antibody having desired immunospecificity which is obtained by cell fusion of a B cell obtained by immunizing a non-human mammal with an antigen, with a myeloma cell.

The recombinant antibody includes an antibody produced by gene recombination, such as a human chimeric antibody, a humanized antibody, a human antibody and an antibody fragment thereof. Among the recombinant antibodies, one having characteristics as a monoclonal antibody, low immunogenecity and prolonged half-life in blood is preferable as a therapeutic agent.

Examples of the recombinant antibody of the present invention include a recombinant antibody in which CDR1, CDR2 and CDR3 of VH of the antibody comprise the amino acid sequences represented by SEQ ID NOs:12, 13 and 14, respectively, and CDR1, CDR2 and CDR3 of VL of the antibody comprise the amino acid sequences represented by SEQ ID NOs:15, 16 and 17, respectively.

The recombinant antibody of the present invention an antibody produced by gene recombination, such as a human chimeric antibody, a humanized antibody, a human antibody and an antibody fragment thereof.

The human chimeric antibody is an antibody comprising VH and VL of an antibody of a nonhuman animal and a heavy chain constant region (hereinafter referred to as "CH") and a light chain constant region (hereinafter referred to as "CL") of a human antibody.

The human chimeric antibody of the present invention can be produced as follows. First, cDNAs encoding VII and VL are obtained from a hybridoma producing a monoclonal antibody which binds to a cell membrane-bound H-EGF, a secretory HB-EGF and a membrane type HB-EGF. The resulting cDNAs are inserted into an expression vector for animal cell comprising genes encoding CH and CL of a human antibody to thereby construct a human chimeric antibody expression vector, the human chimeric antibody expression vector is introduced into an animal cell to thereby express the human chimeric antibody, and then the human chimeric antibody can be produced.

As the CH of the human chimeric antibody, any CH can be used, so long as it belongs to a human immunoglobulin (hereinafter referred to as "hIg"), and those belonging to the hIgG class are preferred, and any one of the subclasses belonging to the hIgG class, such as hIgG1, hIgG2, hIgG3 and hIgG4, can be used. As the CL of the human chimeric antibody, any CL can be used, so long as it belongs to the hIg class, and those belonging to the κ class or λ class can be used.

The human chimeric antibody of the present invention includes, for example, a human chimeric antibody in which VH of the antibody comprises the amino acid sequence represented by SEQ ID NO:9 and VL of the antibody comprises the amino acid sequence represented by SEQ ID NO:11, and the like. Also, the human chimeric antibody in which VH of the antibody comprises the amino acid sequence represented by SEQ ID NO:9 and VL of the antibody comprises the amino acid sequence represented by SEQ ID NO:10 includes, for example, human chimeric antibody KM3966 and the like.

A humanized antibody is an antibody in which amino acid sequences of CDRs of VH and VL of an antibody derived from a non-human animal are grafted into appropriate positions of VH and VL of a human antibody, and is also called a CDR-grafted antibody, a reshaped-antibody or the like.

The humanized antibody of the present invention can be produced as follows. First, cDNAs encoding V regions in which the amino acid sequences of CDRs of VH and VL of a monoclonal antibody derived from a non-human animal which binds to a cell membrane-bound HB-EGF, a secretory HB-EGF and a membrane type HB-EGF are grafted into frameworks (hereinafter referred to as "FR") of VH and VL of any human antibody are constructed. The constructed cDNAs are respectively inserted into an expression vector for animal cell comprising genes encoding CH and CL of a human antibody to thereby construct a humanized antibody expression vector. Next, the constructed humanized antibody expression vector is introduced into an animal cell to thereby express the humanized antibody, and the humanized antibody can be produced.

As the amino acid sequences of FRs of VH and VL of a human antibody, any amino acid sequences can be used, so long as they are amino acid sequences of VH and VL, respectively, derived from a human antibody. Examples include amino acid sequences of VH and VL of human antibodies registered in database such as Protein Data Bank, common amino acid sequences of each sub group of FRs of VH and VL of human antibodies described in, for example, *Sequences of Proteins of Immunological Interest*, US Dept. Health and Human Services (1991), and the like.

As the CH of the humanized antibody, any CH can be used, so long as it belongs to the hIg, and those of the hIgG class are preferred and any one of the subclasses belonging to the hIgG class, such as hIgG1, hIgG2, hIgG3 and hIgG4 can be used. As the CL of the human CDR-grafted antibody, any CL can be used, so long as it belongs to the Mg class, and those belonging to the κ class or λ class can be used.

The humanized antibody of the present invention includes, for example, a humanized antibody in which VH of the antibody comprises the amino acid sequence represented by SEQ ID NO:22 or an amino acid sequence in which at least one amino acid residue selected from Ala at position 9, Val at position 20, Thr at position 30, Arg at position 38, Pro at position 41, Met at position 48, Arg at position 67, Val at position 68, Ile at position 70, Tyr at position 95 and Val at position 118 in the amino acid sequence represented by SEQ ID NO:22 is substituted with other amino acid residue, and/or VL of the antibody comprises the amino acid sequence represented by SEQ ID NO:23 or an amino acid sequence in which at least one amino acid residue selected from Leu at position 15, Ala at position 19, Ile at position 21, Pro at position 49 and Leu at position 84 in the amino acid sequence represented by SEQ ID NO:23 is substituted with other amino acid residue, and the like. The number of these modifications to be introduced is not particularly limited.

For example, regarding the amino acid sequence of VII of the antibody, examples include:

a humanized antibody in which VH of the antibody comprises an amino acid sequence in which Val at position 20, Thr at position 30, Arg at position 38, Met at position 48, Arg at position 67, Val at position 68, Ile at position 70, Tyr at position 95 and Val at position 118 in the amino acid sequence represented by SEQ ID NO:22 are substituted with other amino acid residues, preferably VH of the antibody comprises an amino acid sequence in which Val at position 20, Thr at position 30, Met at position 48, Val at position 68, Ile at position 70, Tyr at position 95 and Val at position 118 are substituted with other amino acid residues;

preferably a humanized antibody in which VH of the antibody comprises an amino acid sequence in which Thr at position 30, Met at position 48, Val at position 68, Ile at position 70 and Tyr at position 95, more preferably Thr at position 30, Met at position 48, Val at position 68 and Ile at position 70 are substituted with other amino acid residues preferably a humanized antibody in which VH of the antibody comprises an amino acid sequence in which Thr at position 30, Val at position 68, Ile at position 70 and Tyr at position 95 are substituted with other amino acid residues;

preferably a humanized antibody in which VH of the antibody comprises an amino acid sequence in which Thr at position 30, Val at position 68 and Ile at position 70 are substituted with other amino acid residues;

preferably a humanized antibody in which VH of the antibody comprises an amino acid sequence in which Thr at position 30 and Ile at position 70 are substituted with other amino acid residues; and the like.

The amino acid sequence of VH of the antibody obtained by the above amino acid modifications include an amino acid sequence into which at least one modification selected from substitutions of Ala at position 9 to Thr, Val at position 20 to Leu, Thr at position 30 to Arg, Arg at position 38 to Lys, Pro at position 41 to Thr, Met at position 48 to Ile, Arg at position 67 to Lys, Val at position 68 to Ala, Ile at position 70 to Leu, Tyr at position 95 to Phe, and Val at position 118 to Leu in the amino acid sequence represented by SEQ ID NO:22 is introduced.

The amino acid sequence of VH into which 11 modifications are introduced includes, for example, an amino acid sequence in which modifications are carried out to substitute Ala at position 9 with Thr, Val at position with Leu, Thr at position 30 with Arg, Arg at position 38 to Lys, Pro at position 41 with Thr, Met at position 48 with Ile, Arg at position 67 with Lys, Val at position 68 with Ala, Ile at position 70 with Leu, Tyr at position 95 with Phe, and Val at position 118 with Leu in the amino acid sequence represented by SEQ ID NO:22.

The amino acid sequence of VH into which 10 modifications are introduced includes, for example, an amino acid sequence in which modifications are carried out to substitute Ala at position 9 with Thr, Val at position 20 with Leu, Thr at position 30 with Arg, Arg at position 38 with Lys, Pro at position 41 with Thr, Met at position 48 with Ile, Arg at position 67 with Lys, Val at position 68 with Ala, Ile at position 70 with Leu, and Tyr at position 95 with Phe in the amino acid sequence represented by SEQ ID NO:22, and the like.

The amino acid sequence of VH into which 9 modifications are introduced includes, for example, an amino acid sequence in which modifications are carried out to substitute Ala at position 9 with Thr, Val at position 20 with Leu, Thr at position 30 with Arg, Pro at position 41 with Thr, Met at position 48 with Ile, Arg at position 67 with Lys, Val at position 68 with Ala, Ile at position 70 with Leu, and Tyr at position 95 with Phe, an amino acid sequence in which modifications are carried out to substitute Val at position 20 with Leu, Thr at position 30 with Arg, Arg at position 38 with Lys, Met at position 48 with Ile, Arg at position 67 with Lys, Val at position 68 with Ala, Ile at position 70 with Leu, Tyr at position 95 with Phe, and Val at position 118 with Leu, and the like, in the amino acid sequence of SEQ ID NO:22.

The amino acid sequence of VH into which 8 modifications are introduced includes, for example, an amino acid sequence in which modifications are carried out to substitute Ala at position 9 with Thr, Val at position 20 with Leu, Thr at position 30 with Arg, Pro at position 41 with Thr, Met at position 48 with Ile, Val at position 68 with Ala, Ile at position 70 with Leu, and Tyr at position 95 with Phe, an amino acid sequence in which modifications are carried out to substitute Val at position 20 with Leu, Thr at position 30 with Arg, Met at position 48 with Ile, Arg at position 67 with Lys, Val at position 68 with Ala, Ile at position 70 with Leu, Tyr at position 95 with Phe, and Val at position 118 with Leu, an amino acid sequence in which modifications are carried out to substitute Val at position 20 with Leu, Thr at position 30 with Arg, Arg at position 38 with Lys, Met at position 48 with Ile, Val at position 68 with Ala, Ile at position 70 with Leu, Tyr at position 95 with Phe, and Val at position 118 with Leu, and the like, in the amino acid sequence represented by SEQ ID NO:22.

The amino acid sequence into which 7 modifications are introduced includes, for example, an amino acid sequence in which modifications are carried out to substitute Ala at position 9 with Thr, Thr at position 39 with Arg, Pro at position 41 with Thr, Met at position 48 with Ile, Val at position 68 with Ala, Ile at position 70 with Leu, and Tyr at position 95 with Phe, an amino acid sequence in which modifications are carried out to substitute Val at position 20 with Leu, Thr at position 30 with Arg, Met at position 48 with Ile, Val at position 68 with Ala, Ile at position 70 with Leu, Tyr at position 95 with Phe, and Val at position 118 with Leu, and the like, in the amino acid sequence represented by SEQ ID NO:22.

The amino acid sequence into which 6 modifications are introduced includes, for example, an amino acid sequence in which modifications are carried out to substitute Ala at position 9 with Thr, Thr at position 30 with Arg, Met at position 48 with Ile, Val at position 68 with Ala, Ile at position 70 with Leu, and Tyr at position 95 with Phe, an amino acid sequence in which modifications are carried out to substitute Val at position 20 with Leu, Thr at position 30 with Arg, Met at position 48 with Ile, Val at position 68 with Ala, Ile at position 70 with Leu, and Tyr at position 95 with Phe, and the like, in the amino acid sequence represented by SEQ ID NO:22.

The amino acid sequence of VH into which 5 modifications are introduced includes, for example, an amino acid sequence in which modifications are carried out to substitute Ala at position 9 with Thr, Thr at position 30 with Arg, Met at position 48 with Ile, Val at position 68 with Ala, and Ile at position 70 with Leu, an amino acid sequence in which modifications are carried out to substitute Thr at position 30 with Arg, Met at position 48 with Ile, Val at position 68 with Ala, Ile at position 70 with Leu, and Tyr at position 95 with Phe, and the like, in the amino acid sequence of SEQ ID NO:22.

The amino acid sequence into which 4 modifications are introduced includes, for example, an amino acid sequence in which modifications are carried out to substitute Ala at position 9 with Thr, Thr at position 30 with Arg, Val at position 68 with Ala, and Ile at position 70 with Leu, an amino acid sequence in which modifications are carried out to substitute Thr at position 30 with Arg, Met at position 48 with Ile, Val at position 68 with Ala, and Ile at position 70 with Leu, an amino acid sequence in which modifications are carried out to substitute Val at position 20 with Leu, Thr at position 30 with Arg, Val at position 68 with Ala, and Ile at position 70 with Leu, an amino acid sequence in which modifications are carried out to substitute Thr at position 30 with Arg, Arg at position 38 with Lys, Val at position 68 with Ala, and Ile at position 70 with Leu, an amino acid sequence in which modifications are carried out to substitute Thr at position 30 with Arg, Pro at position 41 with Thr, Val at position 68 with Ala, and Ile at position 70 with Leu, an amino acid sequence in which modifications are carried out to substitute Thr at position 30 with Arg, Arg at position 67 with Lys, Val at position 68 with Ala, and Ile at position 70 with Leu, an amino acid sequence in which modifications are carried out to substitute Thr at position 30 with Arg, Val at position 68 with Ala, Ile at position 70 with Leu, and Tyr at position 95 with Phe, an amino acid sequence in which modifications are carried out to substitute Thr at position 30 with Arg, Val at position 68 with Ala, Ile at position 70 with Leu, and Val at position 118 with Leu, and the Like, in the amino acid sequence represented by SEQ NO:22.

The amino acid sequence of VH into which three modifications are introduced includes, for example, an amino acid sequence in which modifications are carried out to substitute Thr at position 30 with Arg, Val at position 68 with Ala, and Ile at position 70 with Leu, an amino acid sequence in which modifications are carried out to substitute Ala at position 9 with Thr, Thr at position 30 with Arg, and Ile at position 70 with Leu, an amino acid sequence in which modifications are carried out to substitute Val at position 20 with Leu, Thr at position 30 with Arg, and Ile at position 70 with Leu, an amino acid sequence in which modifications are carried out to substitute Thr at position 30 with Arg, Arg at position 38 with Lys, and Ile at position 70 with Leu, an amino acid sequence in which modifications are carried out to substitute Thr at position 30 with Arg, Pro at position 41 with Thr, and Ile at position 70 with Leu, an amino acid sequence in which modifications are carried out to substitute Thr at position 30 with Arg, Met at position 48 with Ile, and Ile at position 70 with Leu, an amino acid sequence in which modifications are carried out to substitute Thr at position 30 with Arg, Arg at position 67 with Lys, and Ile at position 70 with Leu, an amino acid sequence in which modifications are carried out to substitute Thr at position 30 with Arg, Ile at position 70 with Leu, and Tyr at position 95 with Phe, an amino acid sequence in which modifications are carried out to substitute Thr at position 30 with Arg, Ile at position 70 with Leu, and Val at position 118 with Leu, and the like, in the amino acid sequence represented by SEQ ID NO:22.

The amino acid sequence of VH into which two modifications are introduced includes, for example, an amino acid sequence in which modifications are carried out to substitute Thr at position 30 with Arg and Ile at position 70 with Leu, an amino acid sequence in which modifications are carried out to substitute Ala at position 9 with Thr and Ile at position 70 with Leu, an amino acid sequence in which modifications are carried out to substitute Val at position 20 with Leu and Ile at position 70 with Leu, an amino acid sequence in which modifications are carried out to substitute Arg at position 38 with Lys and Ile at position 70 with Leu, an amino acid sequence in which modifications are carried out to substitute Pro at position 41 with Thr and Ile at position 70 with Leu, an amino acid sequence in which modifications are carried out to substitute Met at position 48 with Ile and Ile at position 70 with Leu, an amino acid sequence in which modifications are carried out to substitute Arg at position 67 with Lys and Ile at position 70 with Leu, an amino acid sequence in which modifications are carried out to substitute Val at position 68 with Ala and Ile at position 70 with Leu, an amino acid sequence in which modifications are carried out to substitute Ile at position 70 with Leu and Tyr at position 95 with Phe, an amino acid sequence in which modifications are carried out to substitute Ile at position 70 with Leu and Val at position 118 with Leu, an amino acid sequence in which modifications are carried out to substitute Ala at position 9 with Thr and Thr at position 30 with Arg, an amino acid sequence in which modifications are carried out to substitute Val at position 20 with Leu and Thr at position 30 with Arg, an amino acid sequence in which modifications are carried out to substitute Thr at position 30 with Arg and Arg at position 38 with Lys, an amino acid sequence in which modifications are carried out to substitute Thr at position 30 with Arg and Pro at position 41 with Thr, an amino acid sequence in which modifications are carried out to substitute Thr at position 30 with Arg and Met at position 48 with Ile, an amino acid sequence in which modifications are carried out to substitute Thr at position 30 with Arg and Arg at position 67 with Lys, an amino acid sequence in which modifications are carried out to substitute Thr at position 30 with Arg and Val at position 68 with Ala, an amino acid sequence in which modifications are carried out to substitute Thr at position 30 with Arg and Tyr at position 95 with Phe, an amino acid sequence in which modifications are carried out to substitute Thr at position 30 with Arg and Val at position 118 with Leu, and the like, in the amino acid sequence represented by SEQ ID NO:22.

The amino acid sequence of VH into which one modification is introduced includes, for example, an amino acid sequence in which Ala at position 9 is substituted with Thr, an amino acid sequence in which Val at position 20 is substituted with Leu, an amino acid sequence in which Thr at position 30 is substituted with Arg, an amino acid sequence in which Arg at position 38 is substituted with Lys, an amino acid sequence in which Pro at position 41 is substituted with Thr, an amino acid sequence in which Met at position 48 is substituted with Ile, an amino acid sequence in which Arg at position 67 is substituted with Lys, an amino acid sequence in which Val at position 68 is substituted with Ala, an amino acid sequence in which Ile at position 70 is substituted with Ile, an amino acid sequence in which Tyr at position 95 is substituted with Phe, and an amino acid sequence in which Val at position 118 is substituted with Leu in the amino acid sequence of SEQ ID NO:22.

VL of the antibody includes, for example, an amino acid sequence in which Leu at position 15, Ala at position 19, Ile at position 21 and Leu at position 84 are substituted in the amino acid sequence represented by SEQ ID NO:23.

It is preferably an amino acid in which Ala at position 19, Ile at position 21 and Leu at position 84 are substituted.

The amino acid sequence obtained by the above amino acid modifications include an amino acid sequence into which at least one modification selected from substitutions of Leu at position 15 with Val, Ala at position 19 with Val, Ile at position 21 with Met, Pro at position 49 with Ser, and Leu at position 84 with Val in the amino acid sequence represent by SEQ ID NO:23 is introduced.

The amino acid sequence of VL into which 5 modifications are introduced includes, for example, an amino acid sequence in which modifications are carried out to substitute Leu at position 15 with Val, Ala at position 19 with Val, Ile at position 21 with Met, Pro at position 49 with Ser, and Leu at position 84 with Val, and the like, in the amino acid sequence represented by SEQ ID NO:23.

The amino acid sequence of VL into which 4 modifications are introduced includes, for example, an amino acid sequence in which modifications are carried out to substitute Leu at position 15 with Val, Ala at position 19 with Val, He at position 21 with Met, and Pro at position 49 with Ser, an amino acid sequence in which modifications are carried out to substitute Leu at position 15 with Val, Ala at position 19 with Val, Ile at position 21 with Met, and Leu at position 84 with Val, an amino acid sequence in which modifications are carried out to substitute Leu at position 15 with Val, Ala at position 19 with Val, Pro at position 49 with Ser, and Leu at position 84 with Val, an amino acid sequence in which modifications are carried out to substitute Leu at position 15 with Val, Ile at position 21 with Met, Pro at position 49 with Ser, and Leu at position 84 with Val, an amino acid sequence in which modifications are carried out to substitute Ala at position 19 with Val, Ile at position 21 with Met, Pro at position 49 with Ser, and Len at position 84 with Val, and the like, in the amino acid sequence represented by SEQ ID NO:23.

The amino acid sequence of VL into which three modifications are introduced includes, for example, an amino acid sequence in which modifications are carried out to substitute Leu at position 15 with Val, Ala at position 19 with Val, and Ile at position 21 with Met, an amino acid sequence in which modifications are carried out to substitute Leu at position 15 with Val, Ala at position 19 with Val, and Pro at position 49 with Ser, an amino acid sequence in which modifications are carried out to substitute Leu at position 15 with Val, Ala at position 19 with Val, and Leu at position 84 with Val, an amino acid sequence in which modifications are carried out to substitute Leu at position 15 with Val, Ile at position 21 with Met, and Pro at position 49 with Ser, an amino acid sequence in which modifications are carried out to substitute Leu at position 15 with Val, Ile at position 21 with Met, and Leu at position 84 with Val, an amino acid sequence in which modifications are carried out to substitute Leu at position 15 with Val, Pro at position 49 with Ser, and Leu at position 84 with Val, an amino acid sequence in which modifications are carried out to substitute Ala at position 19 with Val, Ile at position 21 with Met, and Pro at position 49 with Ser, an amino acid sequence in which modifications are carried out to substitute Ala at position 19 with Val, Ile at position 21 with Met, and Leu at position 84 with Val, an amino acid sequence in which modifications are carried out to substitute Ala at position 19 with Val, Pro at position 49 with Ser, and Leu at position 84 with Val, an amino acid sequence in which modifications are carried out to substitute Ile at position 21 with Met, Pro at position 49 with Ser, and Len at position 84 with Val, and the like, in the amino acid sequence represented by SEQ ID NO:23.

The amino acid sequence of VL into which two modifications are introduced includes, for example, an amino acid sequence in which modifications are carried out to substitute Leu at position 15 with Val and Ala at position 19 with Val, an amino acid sequence in which modifications are carried out to substitute Leu at position 15 with Val and Ile at position 21 with Met, an amino acid sequence in which modifications are carried out to substitute Leu at position 15 with Val and Pro at position 49 with Ser, an amino acid sequence in which modifications are carried out to substitute Leu at position 15 with Val and Leu at position 84 with Val, an amino acid sequence in which modifications are carried out to substitute Ala at position 19 with Val and Ile at position 21 with Met, an amino acid sequence in which modifications are carried out to substitute Ala at position 19 with Val and Pro at position 49 with Ser, an amino acid sequence in which modifications are carried out to substitute Ala at position 19 with Val and Leu at position 84 with Val, an amino acid sequence in which modifications are carried out to substitute Ile at position 21 with Met and Pro at position 49 with Ser, an amino acid sequence in which modifications are carried out to substitute Ile at position 21 with Met and Leu at position 84 with Val, an amino acid sequence in which modifications are carried out to substitute Pro at position 49 with Ser and Leu at position 84 with Val, and the like, in the amino acid sequence represented by SEQ ID NO:23.

The amino acid sequence of VL into which one modification is introduced includes, for example, an amino acid sequence in which Leu at position 15 is substituted with Val, an amino acid sequence in which Ala at position 19 is substituted with Val, an amino acid sequence in which Ile at position 21 is substituted with Met, an amino acid sequence in which Pro at position 49 is substituted with Ser, an amino acid sequence in which Leu at position 84 is substituted with Val, and the like, in the amino acid sequence represented by SEQ ID NO:23.

Examples of the humanized antibody of the present invention include a humanized antibody in which variable regions comprise the amino acid sequences represented by SEQ ID NOs:22 and 23.

A human antibody is originally an antibody naturally existing in the human body, but it also includes antibodies obtained from a human antibody phage library or a human antibody-producing transgenic animal, which is prepared based on the recent advance in genetic engineering, cell engineering and developmental engineering techniques. The antibody existing in the human body can be prepared, for example by isolating a human peripheral blood lymphocyte, immortalizing it by infecting with EB virus or the like and then cloning it to thereby obtain lymphocytes capable of producing the antibody, culturing the lymphocytes thus obtained, and purifying the antibody from the supernatant of the culture. The human antibody phage library is a library in which antibody fragments such as Fab and scFv are expressed on the phage surface by inserting a gene encoding an antibody prepared from a human B cell into a phage gene. A phage expressing an antibody fragment having the desired antigen binding activity can be recovered from the library, using its activity to bind to an antigen-immobilized substrate as the index. The antibody fragment can be converted further into a human antibody molecule comprising two full H chains and two full L chains by genetic engineering techniques. A human antibody-producing transgenic animal is an animal in which a human antibody gene is integrated into cells. Specifically, a human antibody-producing transgenic animal can be prepared by introducing a gene encoding a human antibody into a mouse ES cell, grafting the ES cell into an early stage embryo of other mouse and then developing it. A human antibody is prepared from the human antibody-producing transgenic non-human animal by obtaining a human antibody-producing hybridoma by a hybridoma preparation method usually carried out in non-human mammals, culturing the obtained hybridoma and forming and accumulating the human antibody in the supernatant of the culture.

In the amino acid sequence constituting the above antibody or antibody fragment, an antibody or antibody fragment thereof in which one or more amino acids are deleted, substituted, inserted or added, having activity similar to the above antibody or the antibody fragment thereof is also included in the antibody or the antibody fragment thereof of the present invention.

The number of amino acids which are deleted, substituted, inserted and/or added is one or more, and is not specifically limited, but it is within the range where deletion, substitution or addition is possible by known methods such as the site-directed mutagenesis described in *Molecular Cloning*, Second Edition, *Current Protocols in Molecular Biology, Nucleic Acids Research,* 10, 6487 (1982), *Proc. Natl. Acad. Sci. USA,* 79, 6409 (1982), *Gene,* 34, 315 (1985), *Nucleic Acids Research,* 13, 4431 (1985), *Proc. Natl. Acad. Sci. USA,* 82, 488 (1985), or the like. For example, the number is 1 to dozens, preferably 1 to 20, more preferably 1 to 10, and most preferably 1 to 5.

The expression "one or more amino acids are deleted, substituted, inserted or added" in the amino acid sequence of the above antibody means the followings. That is, it means there is deletion, substitution, insertion or addition of one or plural amino acids at optional positions in the same sequence and one or plural amino acid sequences. Also, the deletion, substitution, insertion or addition may occur at the same time and the amino acid which is substituted, inserted or added may be either a natural type or a non-natural type. The natural type amino acid includes L-alanine, L-asparagine, L-aspartic acid, L-glutamine, L-glutamic acid, glycine, L-histidine, L-isoleucine, L-leucine, L-lysine, L-methionine, L-phenylalanine, L-proline, L-serine, L-threonine, L-tryptophan, L-tyrosine, L-valine, L-cysteine and the like.

Preferable examples of mutually substitutable amino acids are shown below. The amino acids in the same group are mutually substitutable.

Group A: leucine, isoleucine, norleucine, valine, norvaline, alanine, 2-aminobutanoic acid, methionine, O-methylserine, t-butylglycine, t-butylalanine, cyclohexylalanine
Group B: aspartic acid, glutamic acid, isoaspartic acid, isoglutamic acid, 2-aminoadipic acid, 2-aminosuberic acid
Group C: asparagine, glutamine
Group D: lysine, arginine, ornithine, 2,4-diaminobutanoic acid, 2,3-diaminopropionic acid
Group E: proline, 3-hydroxyproline, 4-hydroxyproline
Group F: serine, threonine, homoserine
Group G: phenylalanine, tyrosine The antibody fragment of the present invention includes Fab, Fab', F(ab')$_2$, scFv, diabody, dsFv, and the like.

An Fab is obtained by treating an IgG antibody molecule with a protease, papain. This is an antibody fragment having a molecular weight of about 50,000 and having antigen binding activity, in which about a half of the N-terminal side of H chain and the entire L chain, among fragments obtained, papain (cleaved at an amino acid residue at position 224 of the H chain), are bound together through a disulfide bond.

The Fab of the present invention can be produced by treating an antibody with a protease, papain. Also, the Fab of the present invention can be produced by inserting DNA encoding Fab of the antibody into an expression vector for prokaryote or an expression vector for eukaryote, and introducing the vector into a prokaryote or eukaryote to express the Fab.

A F(ab')$_2$ is an antibody fragment having antigen binding activity and having a molecular weight of about 100,000 which is somewhat larger than one in which Fab is bound via a disulfide bond in the hinge region, among fragments obtained by treating an IgG antibody molecule with a protease, pepsin (by cleaving the H chain at the 234th amino acid residue).

The F(ab')$_2$ of the present invention can be produced by treating an antibody with a protease, pepsin. Also, the F(ab')$_2$ of the present invention can be produced by binding Fab' described below via a thioether bond or a disulfide bond.

A Fab' is an antibody fragment having antibody binding activity and having a molecular weight of about 50,000 in which the disulfide bond in the hinge region of the above F(ab')$_2$ is cleaved.

The Fab' of the present invention can be produced by F(ab')$_2$ with a reducing agent, dithiothreitol. Also, the Fab' of the present invention can be produced by inserting DNA encoding Fab' fragment of the antibody into an expression vector for prokaryote or an expression vector for eukaryote, and introducing the vector into a prokaryote or eukaryote to express the Fab'.

An scFv is an antibody fragment having antigen binding activity which is a VH-P-VL or VL-P-VH polypeptide in which one chain VH and one chain VL are linked using an appropriate peptide linker (hereinafter referred to as "P"). The scFv of the present invention can be produced by obtaining cDNAs encoding VH and VL of the antibody, constructing DNA encoding scFv, inserting DNA encoding scFv of the antibody into an expression vector for prokaryote or an expression vector for eukaryote, and then introducing the expression vector into a prokaryote or eukaryote to express the scFv.

A diabody is an antibody fragment having divalent antigen binding activity in which scFvs are dimerized. The divalent antigen binding activity may be the same or different with each other. The diabody of the present invention can be produced by obtaining cDNAs encoding VH and VL of the antibody, constructing DNA encoding scFv so that the length of the amino acid sequence of P is 8 or less residues, inserting the DNA into an expression vector for prokaryote or an expression vector for eukaryote, and then introducing the expression vector into a prokaryote or eukaryote to express the diabody.

A dsFv is obtained by binding polypeptides in which one amino acid residue of each of VH and VL is substituted with a cysteine residue via a disulfide bond between the cysteine residues. The amino acid residue to be substituted with a cysteine residue can be selected based on a three-dimensional structure estimation of the antibody in accordance with the method shown by Reiter et al. (*Protein Engineering,* 7, 697-704 (1994)). The dsFv of the present invention can be produced by obtaining cDNAs encoding VH and VL of the antibody, constructing DNA encoding dsFv, inserting the DNA into an expression vector for prokaryote or an expression vector for eukaryote, and then introducing the expression vector into a prokaryote or eukaryote to express the dsFv.

Antibody derivatives in which a radioisotope, a protein or an agent is conjugated to the above-described antibody or the antibody fragment thereof can be used in the present invention.

The antibody derivatives of the present invention can be produced by chemically conjugating an agent to the N-terminal side or C-terminal side of an H chain or an L chain of the antibody or the antibody fragment thereof which binds to a cell membrane-bound HB-EGF, a membrane type HB-EGF and a secretory HB-EGF, an appropriate substituent or side chain of the antibody or a sugar chain in the antibody [*Antibody Engineering Handbook*, edited by Osamu Kanemitsu, published by Chijin Shokan (1994)].

Also, the antibody derivatives can be genetically produced by linking a DNA encoding the antibody or the antibody fragment thereof which binds to a cell membrane-bound HB-EGF, a membrane type HB-EGF and a secretory HB-EGF to other DNAs encoding an agent, such as a protein, to be bound, inserting the DNA into a vector for expression, and introducing the expression vector into a host cell.

The agent includes a chemotherapeutic agent, a therapeutic antibody, an immunostimulator such as cytokine, a radioisotope, an immunoadjuvant and the like.

Furthermore, the agent to be bound to the antibody or the antibody fragment thereof may be in a form of a prodrug. The prodrug in the present invention is an agent which is subjected to chemical modification by an enzyme existing in the tumor environment and is converted to a substance having an activity of damaging the tumor cells.

The chemotherapeutic agent includes any chemotherapeutic agents such as an alkylating agent, a nitrosourea agent, a metabolism antagonist, an anticancer antibiotic substance, an alkaloid derived from a plant, a topoisomerase inhibitor, an agent for hormonotherapy, a hormone antagonist, an aromatase inhibitor, a P glycoprotein inhibitor, a platinum complex derivative, an M-phase inhibitor and a kinase inhibitor. Examples of the chemotherapeutic agent include amifostine (Ethyol), cisplatin, dacarbazine (DTIC), dactinomycin, mecloretamin (nitrogen mustard), streptozocin, cyclophosphamide, iphosphamide, carmustine (BCNU), lomustine (CCNU), doxorubicin (adriamycin), doxorubicin lipo (Doxyl), epirubicin, gemcitabine (Gemsal), daunorubicin, daunorubicin lipo (Daunozome), procarbazine, mitomycin, cytarabine, etoposide, methotrexate, 5-fluorouracil, fluorouracil, vinblastine, vincristine, bleomycin, daunomycin, peplomycin, estramustine, paclitaxel (Taxol), docetaxel (Taxotea), aldesleukin, asparaginase, busulfan, carboplatin, oxaliplatin, nedaplatin, cladribine, camptothecin, CPT-11, 10-hydroxy-7-ethylcamptothecin (SN38), floxuridine, fludarabine, hydroxyurea, iphosphamide, idarubicin, mesna, irinotecan, nogitecan, mitoxantrone, topotecan, leuprolide, megestrol, melfalan, mercaptopurine, hydroxycarbamide, plicamycin, mitotane, pegasparagase, pentostatin, pipobroman, streptozocin, tamoxifen, goserelin, leuprorelin, flutamide, teniposide, testolactone, thioguanine, thiotepa, uracil mustard, vinorelbine, chlorambucil, hydrocortisone, prednisolone, methylprednisolone, vindesine, nimustine, semustine, capecitabine, Tomudex, azacytidine, UFT, oxaliplatin, gefitinib (Iressa), imatinib (STI 571), elrotinib, Flt3 inhibitor, VEGFR inhibitor, FGFR inhibitor, radicicol, 17-allylamino-17-demethoxygeldanamycin, rapamycin, amsacrine, all-trans-retinoic acid, thalidomide, anastrozole, fadrozole, letrozole, exemestane, gold thiomalate, D-penicillamine, bucillamine, azathioprine, mizoribine, cyclosporine, rapamycin, hydrocortisone, bexarotene (Targretin), tamoxifen, dexamethasone, progestin substances, estrogen substances, anastrozole (Arimidex), Leuplin, aspirin, indomethacin, celecoxib, azathioprine, penicillamine, gold thiomalate, chlorpheniramine maleate, chlorpheniramine, clemastine, tretinoin, bexarotene, arsenic, voltezomib, allopurinol, gemtuzumab, ibritumomab tiuxetan, 131 tositumomab, Targretin, ONTAK, ozogamine, clarithromycin, leucovorin, ifosfamide, ketoconazole, aminoglutethimide, suramin and methotrexate.

The method for conjugating the chemotherapeutic agent with the antibody include a method in which the chemotherapeutic agent and an amino group of the antibody are conjugated via glutaraldehyde, a method in which an amino group of the chemotherapeutic agent and a carboxyl group of the antibody are bound via a water-soluble carbodiimide, and the like.

The therapeutic antibody includes an antibody against an antigen in which apoptosis is induced by binding of the antibody, an antibody against an antigen participating in formation of morbid state of tumor such as growth or metastasis of tumor cells, an antibody which regulates immunological function and an antibody which inhibits angiogenesis in the morbid part.

The antigen in which apoptosis is induced by binding of the antibody includes cluster of differentiation (hereinafter "CD") 19, CD20, CD21, CD22, CD23, CD24, CD37, CD53, CD72, CD73, CD74, CDw75, CDw76, CD77, CDw78, CD79a, CD79b, CD80 (B7.1), CD81, CD82, CD83, CDw84, CD85, CD86 (B7.2), human leukocyte antigen (HLA)-Class II, EGFR and the like.

The antigen for the antibody which regulates immunological function includes CD4, CD40, CD40 ligand, B7 family molecule (CD80, CD86, CD274, B7-DC, B7-H2, B7-H3, B7414), ligand of B7 family molecule (CD28, CTLA-4, ICOS, PD-1, BTLA), OX-40, OX-40 ligand, CD137, tumor necrosis factor (TNF) receptor family molecule (DR4, DR5, TNFR1, TNFR2), TNF-related apoptosis-inducing ligand receptor (TRAIL) family molecule, receptor family of TRAIL family molecule (TRAIL-R1, TRAIL-R2, TRAIL-R3, TRAIL-R4), receptor activator of nuclear factor kappa B ligand (RANK), RANK ligand, CD25, folic acid receptor 4, cytokine [interleukin-1α (hereinafter interleukin is referred to as "IL"), IL-4, IL-5, IL-6, IL-10, IL-13, transforming growth factor (TOP) β, TNFα, etc.], receptors of these cytokines, chemokine (SLC, ELC, 1-309, TARC, MDC, CTACK, etc.) and receptors of these chemokines.

The antigen for the antibody which inhibits angiogenesis in the morbid part includes endothelial growth factor (VEGF), fibroblast growth factor (FGF), EGF, platelet-derived growth factor (PDGF), insulin-like growth factor (IGF), erythropoietin (EPO), TGFβ, IL-8, ephilin, SDP-1 and the like.

The immunostimulator may be any cytokine, so long as it enhances cells such as NK cells, macrophages and neutrophils. Examples include interferon (hereinafter referred to as "INF")-α, INF-β, INF-γ, IL-2, IL-12, IL-15, IL-18, IL-21, IL-23, granulocyte-colony stimulating factor (G-CSF), granulocyte macrophage-colony stimulating factor (GM-CSF), macrophage-colony stimulating factor (M-CSF) and the like. Also, natural products known as immunostimulators are included, and examples of an agent enhancing immunogen include β(1→3)glucan (lentinan, schizophyllan), α-galactosylceramide (KRN7000), fungus powder (picibanil, BCG) and fungus extract (krestin). The radioisotope includes $^{131}$I, $^{125}$I, $^{90}$Y, $^{64}$Cu, $^{99}$Tc, $^{77}$Lu, $^{211}$At and the like. The radioisotope can directly be conjugated with the antibody by a Chloramine-T method. Also, a substance chelating the radioisotope can be conjugated with the antibody. The chelating agent includes methylbenzyldiethylene-triaminepentaacetic acid (MX-DTPA) and the like.

In the present invention, the antibody used in the present invention can be administered in combination with one or more of other agents, and radiation irradiation can be also used in combination. The other agent includes the above-described chemotherapeutic agent, therapeutic antibody, immuno stimulator such as cytokine, and the like.

The therapeutic antibody includes antibodies against the antigens which may become targets, and examples include EGFR antibodies (Cetuximab, Panitumumab, Matuzumab, etc.) and the like.

The radiation irradiation include photon (electromagnetic) irradiation such as X-ray or γ-ray, particle irradiation such as electron beam, proton beam or heavy particle bema, and the like.

In the method for combined administration, the agent may be simultaneously administered with the antibody used in the present invention, or the agent may be administered before or after the administration of the antibody used in the present invention.

The present invention is described below in detail.

1. Process for Producing Recombinant Antibody Composition (1) Preparation of Antigen An expression vector comprising cDNA encoding the secretory HB-EGF or a partial length of the secretory HB-EGF (hereinafter simply referred to as the secretory HB-EGF) is introduced into *Escherichia coli*, yeast, an insect cell, an animal cell or the like for expression to obtain the secretory HB-EGF or a partial fragment of the secretory HB-EGF. Also, HB-EGF in the extracellular region can be purified from cells expressing HB-EGF by protease treatment. The secretory HB-EGF can be purified from various human tumor culturing cells, human tissue and the like which express a large amount of the secretory HB-EGF. Furthermore, a synthetic peptide having a partial sequence of the secretory HB-EGF can be prepared and used as an antigen.

Specifically, the secretory HB-EGF used in the present invention can be produced, for example, by expressing a DNA encoding it in a host cell using a method described in *Molecular Cloning, A Laboratory Manual*, Second Edition, Cold Spring Harbor Laboratory Press (1989), *Current Protocols in Molecular Biology*, John Wiley & Sons (1987-1997) or the like as follows.

Firstly, a recombinant vector is produced by inserting a full length cDNA into downstream of a promoter of an appropriate expression vector. At this time, if necessary, a DNA fragment having an appropriate length containing a region encoding the polypeptide based on the full length cDNA may be prepared, and the DNA fragment may be used instead of the above full length cDNA. Next, a transformant producing HB-EGF can be obtained by introducing the recombinant vector into a host cell suitable for the expression vector.

The host cell can be any cell so long as it can express the gene of interest, and includes *Escherichia coli*, an animal cell and the like.

The expression vector includes vectors which can replicate autonomously in the host cell to be used or vectors which can be integrated into a chromosome comprising an appropriate promoter at such a position that the DNA encoding the secretory HB-EGF can be transcribed.

When a prokaryote such as *Escherichia coli* is used as the host cell, it is preferred that the recombinant vector comprising the DNA encoding HB-EGF used in the present invention is autonomously replicable in the prokaryote and contains a promoter, a ribosome binding sequence, the DNA used in the present invention and a transcription termination sequence. The recombinant vector may further comprise a gene regulating the promoter.

The expression vector includes, for example, pBTrp2, pBTac1, pBTac2 (all manufactured by Roche Diagnostics), pKK233-2 (manufactured by Pharmacia), pSE280 (manufactured by Invitrogen), pGEMEX-1 (manufactured by Promega), pQE-8 (manufactured by QIAGEN), pKYP10 (Japanese Published Unexamined Patent Application No. 110600/83), pKYP200 [*Agricultural Biological Chemistry*, 48, 669 (1984)], pLSA1 [*Agric. Biol. Chem.*, 53, 277 (1989)], pGEL1 [*Proc. Natl. Acad. Sci. USA*, 82, 4306 (1985)], pBluescript II SK(–) (manufactured by Stratagene), pTrs30 [prepared from *Escherichia coli* JM109/pTrS30 (FERM BP-5407)], pTrs32 [prepared from *Escherichia coli* JM109/pTrS32 (FERM BP-5408)], pGHA2 [prepared from *Escherichia coli* IGHA2 (FERM BP-400), Japanese Published Unexamined Patent Application No. 221091/85], pGKA2 [prepared from *Escherichia coli* IGKA2 (FERM BP-6798), Japanese Published Unexamined Patent Application No. 221091/85], pTerm2 (U.S. Pat. No. 4,686,191, U.S. Pat. No. 4,939,094, U.S. Pat. No. 5,160,735), pSupex, pUB110, pTP5, pC194, pEG400 [*J. Bacteriol.*, 172, 2392 (1990)], pGEX (manufactured by Pharmacia), pET system (manufactured by Novagen), pME18SFL3 and the like.

Any promoter can be used, so long as it can function in the host cell to be used. Examples include promoters derived from *Escherichia coli*, phage and the like, such as trp promoter (Ptrp), lac promoter, PL promoter, PR promoter and T7 promoter. Also, artificially designed and modified promoters, such as a tandem promoter in which two Ptrp are linked in tandem, tac promoter, lacT7 promoter and letI promoter, can be used.

Also, the above recombinant vector is preferably a plasmid in which the space between Shine-Dalgarno sequence, which is the ribosome binding sequence, and the initiation codon is adjusted to an appropriate distance (for example, 6 to 18 nucleotides). In the nucleotide sequence of DNA encoding the secretory HB-EGF used in the present invention, nucleotides can be arranged so as to obtain a suitable codon for expression in the host so that the producing ratio of the secretory HB-EGF of interest can be improved. Furthermore, the transcription termination sequence is not essential to express a gene in the above recombinant vector. However, it is preferred to arrange a transcription terminating sequence immediately downstream of the structural gene.

The prokaryotes used for the host cells include prokaryotes belonging to the genera *Escherichia*, and examples include *Escherichia coli* XL1-Blue, *Escherichia coli* XL2-Blue, *Escherichia coli* DH1, *Escherichia coli* DH5α, *Escherichia coli* BL21 (DE3), *Escherichia coli* MC1000, *Escherichia coli* KY3276, *Escherichia coli* W1485, *Escherichia coli* JM109, *Escherichia coli* HB101, *Escherichia coli* No. 49, *Escherichia coli* W3110, *Escherichia coli* NY49 and the like.

Any introduction method of the recombinant vector can be used, so long as it is a method for introducing DNA into the above-described host cell, and examples include a method using a calcium ion described in *Proc. Natl. Acad. Sci. USA*, 69, 2110 (1972), *Gene*, 17, 107 (1982), *Molecular & General Genetics*, 168, 111 (1979) and the like.

When an animal cell is used as the host cell, an expression vector includes, for example, pcDNAI, pcDMS (available from Funakoshi), pAGE107 [Japanese Published Unexamined Patent Application No. 22979/91; *Cytotechnology*, 3, 133 (1990)], pAS3-3 (Japanese Published Unexamined Patent Application No. 227075/90), pCDM8 [*Nature*, 329, 840, (1987)], pcDNAI/Amp (manufactured by Invitrogen), pREP4 (manufactured by Invitrogen), pAGE103 [*J. Biochemistry*, 101, 1307 (1987)], pAGE210, pME18SFL3 and the like.

Any promoter can be used, so long as it can function in an animal cell. Examples include a promoter of IE (immediate early) gene of cytomegalovirus (CMV), SV40 early promoter, a promoter of retrovirus, a metallothionein promoter, a heat shock promoter, SRα promoter and the like. Also, the enhancer of the IE gene of human CMV can be used together with the promoter.

The host cell includes human Namalwa cell, monkey COS cell, Chinese hamster ovary (CHO) cell, HST5637 (Japanese Published Unexamined Patent Application No. 299/88) and the like.

Any introduction method of the recombinant vector can be used, so long as it is a method for introducing DNA into an animal cell, and examples include electroporation [*Cytotechnology*, 3, 133 (1990)], the calcium phosphate method (Japanese Published Unexamined Patent Application No. 227075/90), the lipofection method [*Proc. Natl. Acad. Sci. USA*, 84, 7413 (1987)], and the like.

As the expression method of the gene, in addition to direct expression, secretory production, fusion protein expression and the like in accordance with the method described in *Molecular Cloning, A Laboratory Manual*, Second Edition, Cold Spring Harbor Laboratory Press (1989) can be carried out. When expression is carried out in a cell derived from eukaryote, the secretory HB-EGF to which a sugar or a sugar chain is added can be obtained.

The secretory HB-EGF used in the present invention can be produced by culturing the thus obtained transformant in a medium to form and accumulate the secretory HB-EGF in the culture, and recovering it from the culture. The method for culturing the transformant in the medium is carried out according to the usual method used in culturing of hosts.

When a microorganism transformed with a recombinant vector containing an inducible promoter as a promoter is cultured, an inducer can be added to the medium, if necessary. For example, isopropyl-β-D-thiogalactopyranoside or the like can be added to the medium when a microorganism transformed with a recombinant vector using lac promoter is cultured, or indoleacrylic acid or the like can be added thereto when a microorganism transformed with a recombinant vector using trp promoter is cultured.

When a transformant obtained using an animal cell as the host cell is cultured, the medium includes generally used RPMI 1640 medium [*The Journal of the American Medical Association*, 199, 519 (1967)], Eagle's MEM medium [*Science*, 122, 501 (1952)], Dulbecco's modified MEM medium [*Virology*, 8, 396 (1959)] and 199 medium [*Proceeding of the Society for Experimental Biology and Medicine*, 73, 1 (1950)], the media to which fetal calf serum, etc. is added, and the like. The culturing is carried out generally at a pH of 6 to 8 and 30 to 40° C. for 1 to 7 days in the presence of 5% $CO_2$. If necessary, an antibiotic such as kanamycin or penicillin can be added to the medium during the culturing.

Thus, the secretory HB-EGF used in the present invention can be produced by culturing a transformant derived from a microorganism, an animal cell or the like which comprises a recombinant vector into which a DNA encoding the secretory HB-EGF used in the present invention is inserted, in accordance with a general culturing method, to thereby form and accumulate the polypeptide, and then recovering the secretory HB-EGF from the culture.

Regarding the expression method of gene, in addition to direct expression, secretory production, fusion protein expression and the like can be carried out according to the method described in *Molecular Cloning, A Laboratory Manual*, Second Edition, Cold Spring Harbor Laboratory Press (1989).

The process for producing the secretory HB-EGF includes a method of intracellular expression in a host cell, a method of extracellular secretion from a host cell, a method of producing on a host cell membrane outer envelope, and the like. The appropriate method can be selected by changing the host cell used and the structure of the secretory HB-EGF produced.

When the secretory HB-EGF is produced in a host cell or on a host cell membrane outer envelope, the gene product can be positively secreted extracellularly in accordance with the method of Paulson et al. [*J. Biol. Chem.*, 264, 17619 (1989)], the method of Lowe et al. [*Proc. Natl. Acad. Sci. USA*, 86, 8227 (1989), *Genes Develop.*, 4, 1288 (1990)], the methods described in Japanese Published Unexamined Patent Application No. 336963/93 and WO94/23021, and the like.

Also, the production amount can be increased in accordance with the method described in Japanese Published Unexamined Patent Application No. 227075/90 utilizing a gene amplification system using a dihydrofolate reductase gene. The secretory HB-EGF can be isolated and purified from the above culture, for example, as follows. When the secretory HB-EGF is intracellularly expressed in a dissolved state, the cells after culturing are recovered by centrifugation, suspended in an aqueous buffer and then disrupted using ultrasonicator, French press, Manton Gaulin homogenizer, dynomill or the like to obtain a cell-free extract. The cell-free extract is centrifuged to obtain a supernatant, and a purified preparation can be obtained by subjecting the supernatant to a general enzyme isolation and purification techniques such as solvent extraction; salting out with ammonium sulfate etc.; desalting; precipitation with an organic solvent; anion exchange chromatography using a resin such as diethylaminoethyl (DEAE)-sepharose, DIAION HPA-75 (manufactured by Mitsubishi Chemical); cation exchange chromatography using a resin such as S-Sepharose FF (manufactured by Pharmacia); hydrophobic chromatography using a resin such as butyl-Sepharose or phenyl-Sepharose; gel filtration using a molecular sieve; affinity chromatography; chromatofocusing; electrophoresis such as isoelectric focusing; and the like which may be used alone or in combination.

When the secretory HB-EGF is expressed intracellularly by forming an inclusion body, the cells are recovered, disrupted and centrifuged in the same manner, and the inclusion body of the secretory HB-EGF are recovered as a precipitation fraction. The recovered inclusion body of the protein is solubilized with a protein denaturing agent. The protein is made into a normal three-dimensional structure by diluting or dialyzing the solubilized solution, and then a purified product of the secretory FIB-EGF is obtained by the same isolation purification method as above.

When the secretory HB-EGF or the derivative such as a glycosylated product is secreted extracellularly, the secretory HB-EGF or the derivative such as a glycosylated product can be recovered from the culture supernatant. That is, the culture is treated by a method such as centrifugation in the same manner as above to obtain a culture supernatant from which solids are removed, a purified product of the polypeptide can be obtained from the culture supernatant by the same isolation purification method as above. Also, the secretory HB-EGF used in the present invention can be produced by a chemical synthesis method, such as Fmoc (fluorenylmethyloxycarbonyl) method or tBoc (t-butyloxycarbonyl) method. Also, it can be chemically synthesized using a peptide synthesizer manufactured by Advanced ChemTech, Perkin- Elmer, Pharmacia, Protein Technology Instrument, Synthecell-Vega, PerSeptive, Shimadzu Corporation, or the like.

(2) Immunization of Animal and Preparation of Antibody-Producing Cell

A mouse, rat or hamster 3 to 20 weeks old is immunized with the antigen prepared above, and antibody-producing cells are collected from the spleen, lymph node or peripheral blood of the animal. Also, when the increase of a sufficient titer in the above animal is recognized due to low immunogenecity, an HB-EGF knockout mouse may by used as an animal to be immunized.

The immunization is carried out by administering the antigen to the animal through subcutaneous, intravenous or intraperitoneal injection together with an appropriate adjuvant (for example, complete Freund's adjuvant, combination of aluminum hydroxide gel with pertussis vaccine, or the like). When the antigen is a partial peptide, a conjugate is produced with a carrier protein such as BSA (bovine serum albumin), KLH (keyhole limpet hemocyanin) or the like, which is used as the antigen.

The administration of the antigen is carried out 5 to 10 times every one week or every two weeks after the first administration. On the 3rd to 7th day after each administration, a blood sample is collected from the fundus of the eye, the reactivity of the serum with the antigen is tested, for example, by enzyme immunoassay [*Antibodies-A Laboratory Manual* (Cold Spring Harbor Laboratory (1988)] or the like. A mouse, rat or hamster showing a sufficient antibody titer in their sera against the antigen used for the immunization is used as the supply source of antibody-producing cells.

In fusion of the antibody-producing cells and myeloma cells, on the 3rd to 7th days after final administration of the antigen, tissue containing the antibody-producing cells such as the spleen from the immunized mouse, rat or hamster is excised to collect the antibody-producing cell. When the spleen cells are used, the spleen is cut out in an MEM medium (Nissui Pharmaceutical) and loosened by tweezers and centrifuged (at 1200 rpm, for 5 minutes). Then, the supernatant is discarded and a Tris-ammonium chloride buffer (pH. 7.65) is applied for 1 to 2 minutes to remove erythrocytes. After washing 3 times with the MEM medium, antibody-producing cells for fusion is provided.

(3) Preparation of Myeloma Cell

An established cell line obtained from mouse is used as myeloma cells. Examples include 8-azaguanine-resistant mouse (derived from BALB/c mouse) myeloma cell line P3-X63Ag8-U1 (P3-U1) [*Current Topics in Microbiology and Immunology*, 18, 1-7 (1978)], P3-NS1/1-Ag41 (NS-1) [*European J. Immunology*, 6, 511-519 (1976)], SP2/0-Ag14 (SP-2) [*Nature*, 276, 269-270 (1978)], P3-X63-Ag8653 (653) [*J. Immunology*, 123, 1548-1550 (1979)], P3-X63-Ag8 (X63) [*Nature*, 256, 495-497 (1975)] and the like. These cell lines are subcultured in an 8-azaguanine medium [a medium in which glutamine (1.5 mM), 2-mercaptoethanol ($5\times10^{-5}$ M), gentamicin (10 μg/ml) and fetal calf serum (FCS) are added to RPMI-1640 medium (hereinafter referred to as "normal medium") and 8-azaguanine (15 μg/ml) is further added] and they are subcultured in the normal medium 3 or 4 days before cell fusion to ensure the cell number of $2\times10^7$ or more on the day for fusion, (4) Cell Fusion The above-described antibody-producing cells and myeloma cells were sufficiently washed with an MEM medium or PBS (1.83 g of disodium hydrogen phosphate, 0.21 g of potassium dihydrogen phosphate, 7.65 g of sodium chloride, 1 liter of distilled water, pH 7.2) and mixed to give a ratio of the antibody-producing cells:the myeloma cells=5 to 10:1, followed by centrifugation (1200 rpm, 5 minutes). Then, the supernatant is discarded, and precipitated cell group is sufficiently loosen. To $10^8$ of the antibody-producing cells, 0.2 to 1 mL of a mixture solution of 2 g of polyethylene glycol-1000 (PEG-1000), 2 mL of MEM and 0.7 mL of dimethylsulfoxide is added under stirring at 37° C., and 1 to 2 mL of MEM medium is added several times every one or two minutes, and MEM medium is added to give a total amount of 50 mL. After centrifugation (900 rpm, 5 minutes), the supernatant is discarded, the cells are gently loosen, and the cells are gently suspended in 100 mL of HAT medium [a medium in which hypoxanthine ($10^{-4}$ M), thymidine ($1.5\times10^{-5}$ M) and aminopterin ($4\times10^{-7}$ M) is added to the normal medium] by suction and sucking out using a measuring pipette. The suspension is dispensed at 100 μL/well onto a 96-well culturing plate and cultured in a 5% $CO_2$ incubator at 37° C. for 7 to 14 days.

After the culturing, a portion of the culture supernatant is sampled and a hybridoma producing a monoclonal antibody which is reactive to all of the cell membrane-bound HB-EGF, the secretory HB-EGF and the membrane type HB-EGF or the purified antibody is selected by binding assay as described below.

Then, cloning is carried out twice by a limiting dilution method [Firstly, HT medium (HAT medium from which aminopterin is removed) is used, and secondly, the normal medium is used], and a hybridoma which shows a stably high antibody titer is selected as the monoclonal antibody-producing hybridoma.

(5) Preparation of Monoclonal Antibody

The hybridoma cells producing an anti-HB-EGF monoclonal antibody obtained in (4) are administered by intraperitoneal injection into 8- to 10-week-old mice or nude mice treated with pristane (0.5 ml of 2,6,10,14-tetramethylpentadecane (pristane) is intraperitoneally administered, followed by feeding for 2 weeks) at a dose of $2\times10^6$ to $5\times10^7$ cells/animal. The hybridoma develops ascites tumor in 10 to 21 days. The ascitic fluid is collected from the mice, centrifuged (at 3,000 rpm, for 5 minutes) to remove solids, subjected to salting out with 40 to 50% saturated ammonium sulfate and then precipitated by caprylic acid, passed through a DEAE-Sepharose column, a protein A column or a gel filtration column to collect an IgG or IgM fraction as a purified monoclonal antibody.

The subclass of the antibody can be determined using a subclass typing kit by enzyme immunoassay. The amount of the protein can be determined by the Lowry method or from the absorbance at 280 nm.

(6) Binding Assay

As the antigen, a gene-introduced cell or a recombinant protein obtained by introducing an expression vector comprising cDNA encoding HB-EGF used in the present invention into *Escherichia coli*, yeast, an insect cell, an animal cell or the like according to the method in (1) or purified HB-EGF or a partial peptide obtained from human tissue is used. When the antigen is a partial peptide, a conjugate is prepared with a carrier protein such as BSA (bovine serum albumin) or KLH (keyhole limpet hemocyanin) and is used.

Among these antigens, a cell line in which the secretory HB-EGF and HB-EGF are bound to the cells are dispensed into a 96-well plate and solid-phased, then immunized animal serum, a culture supernatant of a hybridoma producing a monoclonal antibody or a purified antibody is dispensed as a first antibody and reaction is carried out. After washing with PBS or PBS-0.05% Tween well, an anti-immunoglobulin antibody labeled with an enzyme, a chemiluminescent substance, a radioactive substance or the like is dispensed as a second antibody and reaction is carried out. After washing with PBS-Tween well, reaction according to the labeled substance in the second antibody is carried out.

According to the method as described above, the hybridoma producing the monoclonal antibody which is reactive all of the cell membrane-bound HB-EGF, the secretory HB-EGF and the membrane type HB-EGF or the purified antibody can be selected.

Among the monoclonal antibodies obtained, the antibody having binding inhibition activity of the secretory HB-EGF to the HB-EGF receptor includes monoclonal antibody KM3566 produced by hybridoma cell line KM3566, monoclonal antibody KM3567 produced by hybridoma cell line KM3567, and a monoclonal antibody produced by hybridoma KM3579. The hybridoma KM3579 has been deposited to International Patent Organism Depositary, National Institute of Advanced Industrial Science and Technology (Central 6, 1-1, Higashi 1-chome, Tsukuba-shi, Ibaraki, Japan) as FERM BP-10491 on Jan. 24, 2006.

Furthermore, whether the obtained monoclonal antibody has neutralizing activity to the secretory HB-EGF can be confirmed by carrying out cell growth inhibition assay using the HB-EGF-dependent cell.

The cell used for the cell growth inhibition assay may be any cell, so long as it is a cell capable of binding to the secretory HB-EGF. Examples include a cell line obtained by introducing an EGF receptor gene into a mouse bone marrow-derived cell line 32D clone 3 (ATCC No. CRL-11346) and the like.

After the obtained monoclonal antibody is allowed to react with the secretory HB-EGF on a plate, the above-described cell line is added thereto, followed by culturing. As a control, the above-described cell line is similarly added to a plate to which the secretory HB-EGF is added but no monoclonal antibody is added and a plate to neither the secretory HB-EGF nor monoclonal antibody is added, followed by culturing. The cell growth inhibition ratio can be carried out by measuring the cell number on each plate. The monoclonal antibody having high cell growth inhibition ratio can be selected as a monoclonal antibody having neutralizing activity.

Examples of the monoclonal antibody having neutralizing activity according to the present invention include monoclonal antibody KM3566 produced by hybridoma cell line KM3566 and monoclonal antibody KM3567 produced by hybridoma cell line KM3567. The hybridoma cell lines KM3566 and 3567 have been deposited according to the Budapest Treaty of the International Recognition of the Deposit of Microorganisms for the Purposes of Patent Procedure with International Patent Organism Depositary, National Institute of Advanced Industrial Science and Technology (Tsukuba Central 6, 1-1, Higashi 1-chome, Tsukuba-shi, Ibaraki-ken, Japan) as FERM BP-10490 and FERM BP 10573, on Jan. 24, 2006, and Mar. 23, 2006, respectively.

2. Preparation of Human Chimeric Antibody and Humanized Antibody (1) Construction of Vector for Expression of Humanized Antibody A vector for expression of humanized antibody may be any expression vector for animal cell, so long as a gene encoding CH and/or CL of a human antibody is inserted, The vector for expression of humanized antibody can be constructed by cloning each of genes encoding CH and CL of a human antibody into an expression vector for animal cell, The C region of a human antibody may be CH and CL of any human antibody. Examples include the C region of IgG1 subclass of H chain in a human antibody (hereinafter referred to as "hCγ1"), the C region of is class of L chain in a human antibody (hereinafter referred to as "hCκ"), and the like, As the genes encoding CH and CL of a human antibody, a chromosomal DNA comprising an exon and an intron or cDNA can be used, and cDNA is also used.

As the expression vector for animal cell, any expression vector can be used, so long as a gene encoding the C region of a human antibody can be inserted thereinto and expressed therein. Examples include pAGE107 [*Cytotechnol.*, 3, 133-140 (1990)], pAGE103 [*J. Biochem.*, 101, 1307-1310 (1987)], pHSG274 [*Gene*, 27, 223-232 (1984)], pKCR [*Proceedings of the National Academy of Sciences of the United States of America*, 78, 1527-1531 (1981)], pSG1βd2-4 [*Cytotechnol.*, 4, 173-180 (1990)] and the like. Examples of a promoter and an enhancer used for the expression vector for animal cell include an SV40 early promoter and enhancer [*J. Biochem.*, 101, 1307-1310 (1987)], a Moloney mouse leukemia virus LTR promoter and enhancer [*Biochem. Biophys. Res. Commun.*, 149, 960-968 (1987)], an immunoglobulin H chain promoter [*Cell*, 41, 479-487 (1985)] and enhancer [*Cell*, 33, 717-728 (1983)], and the like.

The vector for expression of human chimeric antibody and humanized antibody may be either of a type in which the antibody H chain and L chain exist on separate vectors or of a type in which they exist on the same vector (hereinafter referred to as "tandem type"). In respect of easiness of construction of a vector for expression of human chimeric antibody and humanized antibody, easiness of introduction into animal cells, and balance between the expression amounts of antibody H chain and L chain in animal cells, the tandem type of the vector for expression of humanized antibody is preferable [*Journal of Immunological Methods*, 167, 271-278 (1994)]. Examples of the tandem type of the vector for expression of humanized antibody include pKANTEX93 (WO 97/10354), pEE18 [*Hybridoma*, 17, 559-567 (1998)], and the like.

(2) Obtaining of cDNA Encoding V Region of Non-Human Animal Antibody and Analysis of Amino Acid Sequence cDNAs encoding VH and VL of a non-human animal antibody such as a mouse antibody can be obtained in the following manner.

mRNA is extracted from a hybridoma to synthesize a cDNA. The synthesized cDNA is cloned into a vector such as a phage or a plasmid to obtain a cDNA library. Each of a recombinant phage or recombinant plasmid comprising a cDNA encoding VH and a recombinant phage or recombinant plasmid comprising a cDNA encoding VL is isolated from the library by using cDNA encoding the C region or V region of a mouse antibody as the probe. Full length nucleotide sequences of VH and VL of the mouse antibody of interest on the recombinant phage or recombinant plasmid are determined, and full length amino acid sequences of VH and VL are deduced from the nucleotide sequences.

As the non-human animal, any animal can be used so long as hybridoma cells can be prepared from the animal, such as mouse, rat, hamster and rabbit. The methods for preparing total RNA from the hybridoma include the guanidine thiocyanate-cesium trifluoroacetate method [*Methods in Enzymology*, 154, 3-28 (1987)], and the methods for preparing mRNA from the total RNA include the oligo (dT) immobilized cellulose column method [*Molecular Cloning, A Laboratory Manual*, Cold Spring Harbor Lab. Press New York (1989)] and the like. Examples of the kits for preparing mRNA from the hybridoma include Fast Track mRNA Isolation Kit (manufactured by Invitrogen) and Quick Prep mRNA Purification Kit (manufactured by Pharmacia) and the like.

The methods for synthesizing the cDNA and for preparing the cDNA library include conventional methods [*Molecular Cloning, A Laboratory Manual*, Cold Spring Harbor Lab. Press New York (1989), *Current Protocols in Molecular Biology*, Supplement 1-34], methods using commercially available kits such as SuperScript™ Plasmid System for cDNA Synthesis and Plasmid Cloning (manufactured by GIBCO BRL) and ZAP-cDNA Synthesis Kit (manufactured by Stratagene), and the like.

In preparing the cDNA library, the vector for integrating the cDNA synthesized using the mRNA extracted from the hybridoma as a template may be any vector, so long as the cDNA can be integrated. Examples of suitable vectors include ZAP Express [*Strategies*, 5, 58-61 (1992)], pBluescript II SK(+) [*Nucleic Acids Research*, 9494 (1989)], λZAP II (manufactured by Stratagene), λgt10, λgt11 [*DNA Cloning: A Practical Approach*, I, 49 (1985)], Lambda BlueMid (manufactured by Clontech), λExCell, pT7T3 18U (manufactured by Pharmacia), pcD2 [*Molecular &Cellular Biology*, 3, 280-289 (1983)], pUC18 [*Gene*, 33, 103-119 (1985)] and the like.

As *Escherichia coli* for introducing the cDNA library constructed with a phage or plasmid vector, any *Escherichia coli* can be used, so long as the cDNA library can be introduced, expressed and maintained. Examples include XL1-Blue MRF' [*Journal of Biotechnology*, 23, 271-289 (1992)], C600 [*Genetics*, 59, 177-190 (1968)], Y1088, Y1090 [*Science*, 222, 778-782 (1983)], NM522 [*Journal of Molecular Biology*, 166, 1-19 (1983)], K802 [*Journal of Molecular Biology*, 16, 118-133 (1966)], JM105 [*Gene* 38, 275-276 (1985)] and the like.

The methods for selecting the cDNA clones encoding VH and VL of a non-human animal-derived antibody from the cDNA library include colony hybridization or plaque hybridization [*Molecular Cloning, A Laboratory Manual*, Cold Spring Harbor Laboratory Press New York (1989)] using an isotope- or fluorescence-labeled probe. It is also possible to prepare the cDNAs encoding VH and VL by preparing primers and carrying out polymerase chain reaction (hereinafter referred to as "PCR") [*Molecular Cloning, A Laboratory Manual*, Cold Spring Harbor Laboratory Press New York (1989), *Current Protocols in Molecular Biology*, Supplement 1-34] using the cDNA or cDNA library as a template.

The nucleotide sequences of the cDNAs selected by the above methods can be determined by cleaving the cDNAs with appropriate restriction enzymes, cloning the fragments into a plasmid such as pBluescript SK(−) (manufactured by Stratagene), and then analyzing the sequences by generally employed nucleotide sequence analyzing methods such as the dideoxy method [*Proceedings of the National Academy of Sciences of the United States of America*, 74, 5463-5467 (1977)] or by use of nucleotide sequence analyzers such as ABI PRISM 377 DNA Sequencer (manufactured by ABI).

The full length of amino acid sequences of Vii and VL are deduced from the determined nucleotide sequences and compared with the full length of amino acid sequences of VH and VL of a known antibody [*Sequences of Proteins of Immunological Interest*, US Dept. Health and Human Services (1991)], whereby it can be confirmed that the obtained cDNAs encode amino acid sequences which completely comprise VH and VL of the antibody including secretory signal sequences. The full length amino acid sequences of VH and VL of the antibody containing signal sequences are compared with the full length amino acid sequences of VH and VL of a known antibody [*Sequences of Proteins of Immunological Interest*, US Dept. Health and Human Services (1991)] to thereby deduce the length and N-terminal amino acid sequence of the signal sequences, and a subgroup to which they belong can be known. Also, the amino acid sequence of each CDR of VH and VL can be found by comparing it with the amino acid sequence of each CDR of VH and VL of a known antibody [*Sequences of Proteins of Immunological Interest*, US Dept Health and Human Services (1991)]

By carrying out homology search of sequences, such as BLAST method [*Journal of Molecular Biology*, 215, 403-410 (1990)], using full length amino acid sequence of VH and VL with any databases such as SWISS-PROT or PIR-Protein, the novelty of the sequence can be studied.

(3) Construction of Human Chimeric Antibody Expression Vector cDNAs encoding VII and VL of antibody of non-human animal are cloned into the upstream of genes encoding CH and CL of human antibody of vector for expression of humanized antibody into which DNAs encoding CH and CL of a human antibody are inserted mentioned in (2)-1 of this item to thereby construct a human chimeric antibody expression vector. For example, each cDNA encoding VH and VL of antibody of non-human animal is ligated to synthetic DNA comprising a nucleotide sequence of 3'-terminal of VH or VL of antibody of non-human animal and a nucleotide sequence of 5'-terminal of CH or CL of human antibody and having recognition sequence of an appropriate restriction enzyme at both ends, and cloned so that each of them is expressed in an appropriate form in the upstream of gene encoding CH or CL of human antibody of the vector for expression of antibody into which DNAs encoding CH and CL of a human antibody have been inserted mentioned in (2)-1 of this item to construct a human chimeric antibody expression vector. Also, using a plasmid comprising cDNAs encoding VH and VL of antibody of a non-human animal as the probe, cDNA encoding VII and VL is amplified by PCR using a primer having a recognition sequence of an appropriate restriction enzyme at the 5'-terminal, and each of them is cloned into the upstream of the genes encoding CH and CL in the vector for expression of humanized antibody described in (2)-1 of this item so that it can be expressed in an appropriate form to construct a human chimeric antibody expression vector.

(4) Construction of cDNA Encoding V Region of Humanized Antibody (CDR-Grafted Antibody)

cDNAs encoding VH or VL of a humanized antibody can be obtained as follows. First, amino acid sequences of FR in VH or VL of a human antibody to which amino acid sequences of CDRs in VH or VL of a target antibody of a non-human animal are grafted are selected. Any amino acid sequences of FR in VH or VL of a human antibody can be used, so long as they are derived from human antibody. Examples include amino acid sequences of FRs in VH or VL of human antibodies registered in database such as Protein Data Bank, amino acid sequences common to subgroups of FRs in VH or VL of human antibodies [*Sequences of Proteins of Immunological Interest*, US Dept. Health and Human. Services (1991)], and the like. Among these, in order to produce a humanized antibody having potent activity, amino acid sequences having high homology (at least 60% or more) with an amino acid sequence of FR in VH or VL of a target antibody of a non-human animal is preferably selected, Then, amino acid sequences of CDRs of VH or VL of the target antibody of a non-human animal are grafted to the selected amino acid sequence of FR in VH or VL of a human antibody, respectively, to design each amino acid sequence of VH or VL of a humanized antibody. The designed amino acid sequences are converted to DNA sequences by considering the frequency of codon usage found in nucleotide sequences of genes of antibodies [*Sequence of Proteins of Immunological Interest*, US Dept. Health and Human Services (1991)], and the DNA sequence encoding the amino acid sequence of VH or VL of a humanized antibody is designed. Based on the designed DNA sequences, several synthetic DNAs having a length of about 150 nucleotides are synthesized, and PCR is carried out using them. In this case, in view of the reaction efficiency and the length of DNA which can be synthesized, it is preferred that 4 synthetic DNAs are designed for each of VU and VL.

Furthermore, it can be easily cloned into the vector for expression of humanized antibody constructed in (2)-1 of this item by introducing the recognition sequence of an appropriate restriction enzyme to the 5'-terminal of the synthetic DNAs existing on the both ends. After PCR, each of amplified products is cloned into a plasmid such as pBluescript SK (−) (manufactured by Stratagene), and the nucleotide sequence is determined according to the method described in 2(2) of this item to obtain a plasmid having an amino acid sequence of VH or VL of a desired humanized antibody.

(5) Modification of Amino Acid Sequence of V Region of Humanized Antibody

It is known that when a humanized antibody is produced by simply grafting only CDRs in VH and VL of a target antibody of a non-human animal into FRs of VH and VL of a human antibody, its antigen-binding activity is lower than that of the original antibody from a non-human animal [*BIO/TECHNOLOGY*, 2, 266-271 (1991)]. As the reason, it is considered that several amino acid residues in not only CDRs but also FRs directly or indirectly relate to antigen-binding activity in VH and VL of the original antibody of a non-human animal, and as a result of grafting of CDRs, such amino acid residues are changed to different amino acid residues of FRs in VII and VL of a human antibody. In order to solve the problem, in humanized antibodies, among the amino acid sequences of FRs in VH and VL of a human antibody, an amino acid residue which directly relates to binding to an antigen, or an amino acid residue which indirectly relates to binding to an antigen by interacting with an amino acid residue in CDR or by maintaining the three-dimensional structure of an antibody is identified and modified to an amino acid residue which is found in the original antibody of a non-human animal to thereby increase the antigen binding activity which has been decreased [*BIO/TECHNOLOGY*, 9, 266-271 (1991)]. In the production of a humanized antibody, how to efficiently identify the amino acid residues relating to the antigen binding activity in FR is most important, so that the three-dimensional structure of an antibody is constructed and analyzed by X-ray crystallography [*Journal of Molecular Biology* 112, 535-542 (1977)], computer-modeling [*Protein Engineering*, 7, 1501-1507 (1994)] or the like. Although the information of the three-dimensional structure of antibodies has been useful in the production of a humanized antibody, no method for producing a human CDR-grafted antibody which can be applied to any antibodies has been established yet. Therefore, various attempts must be currently necessary, for example, several modified antibodies of each antibody are produced and the correlation between each of the modified antibodies and its antibody binding activity is examined.

The modification of the amino acid sequence of FR in VH and VL of a human antibody can be accomplished using various synthetic DNA for modification according to PCR as described in 2(4) of this item. With regard to the amplified product obtained by the PCR, the nucleotide sequence is determined according to the method as described in 2(2) of this item so that whether the objective modification has been carried out is confirmed.

(6) Construction of Humanized Antibody Expression Vector

A humanized antibody expression vector can be constructed by cloning each cDNA encoding VII or VL of the constructed humanized antibody as described in 2(4) and 2(5) of this item into upstream of each gene encoding CH or CL of the human antibody in the vector for expression of antibody as described in 2(1) of this item. For example, when recognizing sequences of an appropriate restriction enzymes are introduced to the 5'-terminal of synthetic DNAs positioned at both ends among synthetic DNAs used in the construction of VH or VL of the humanized antibody in 2(4) and 2(5) of this item, cloning can be carried out so that they are expressed in an appropriate form in the upstream of each gene encoding CH or CL of the human antibody in the vector for expression of antibody as described in 2(1) of this item.

(7) Transient Expression of Humanized Antibody

In order to efficiently evaluate the antigen binding activity of various humanized antibodies produced, the humanized antibodies can be expressed transiently using the humanized antibody expression vector as described in 2(3) and 2(6) of this item or an expression vector obtained by modifying it, Any cell can be used as a host cell to which an expression vector is introduced, so long as the host cell can express a humanized antibody. Generally, COS-7 cell (ATCC CRL1651) is used in view of its high expression amount [*Methods in Nucleic Acids Research*, CRC Press, 283 (1991)]. Examples of the method for introducing the expression vector into COS-7 cell include a DEAE-dextran method [*Methods in Nucleic Acids Research*, CRC Press, 283 (1991)], a lipofection method [*Proceedings of the National Academy of Sciences of the United States of America*, 84, 7413-7417 (1987)], and the like.

After introduction of the expression vector, the expression amount and antigen binding activity of the humanized antibody in the culture supernatant can be determined by ELISA [*Antibodies: A Laboratory Manual*, Cold Spring Harbor Laboratory, Chapter 14 (1988); *Monoclonal Antibodies: Principles and Practice*, Academic Press Limited (1996)] and the like.

(8) Stable Expression of Humanized Antibody

A transformant cell which stably expresses a humanized antibody can be obtained by introducing the humanized antibody expression vector described in 2(3) and 2(6) of this item into an appropriate host cell. Examples of the method for introducing the expression vector into a host cell include electroporation [*Cytotechnology*, 3, 133-140 (1990)] and the like. As the host cell into which a humanized antibody expression vector is introduced, any cell can be used, so long as it is a host cell which can express the humanized antibody. Examples include mouse SP2/0-Ag14 cell (ATCC CRL 1581), mouse P3×63-Ag8.653 cell (ATCC CRL1580), CHO cell in which a dihydrofolate reductase gene (hereinafter referred to as "dhfr") is defective [*Proceedings of the National Academy of Sciences of the United States of America*, 77, 4216-4220 (1980)], rat YB2/3HL.P2.G11.16Ag.20 cell (ATCC CRL1662, hereinafter referred to as "YB2/0 cell"), and the like.

After introduction of the expression vector, transformants which express a humanized antibody stably are selected in accordance with the method disclosed in Japanese Published Unexamined Patent Application No. 257891/90, by culturing in a medium for animal cell culture containing an agent such as G418 sulfate (hereinafter referred to as "G418") or the like. Examples of the medium for animal cell culture include RPMI1640 medium (manufactured by Nissui Pharmaceutical), GIT medium (manufactured by Nihon Pharmaceutical), EX-CELL301 medium (manufactured by JRH), IMDM medium (manufactured by GIBCO BRL), Hybridoma-SFM medium (manufactured by GIBCO BRL), media obtained by adding various additives such as FBS to these media, and the like. The humanized antibody can be expressed and accumulated in a culture supernatant by culturing the selected transformant cell in a medium. The expression amount and antigen binding activity of the humanized antibody in the culture supernatant can be measured by ELISA. Also, in the transformant cell, the expression amount of the humanized antibody can be increased by using DHFR amplification system or the like according to the method disclosed in Japanese Published Unexamined Patent Application No. 257891/90.

The humanized antibody can be purified from the culture supernatant of the transformant cell by using a protein A column [*Antibodies: A Laboratory Manual*, Cold Spring Harbor Laboratory, Chapter 8 (1988); *Monoclonal Antibodies: Principles and Practice*, Academic Press Limited (1996)]. Also, in addition thereto, any other conventional methods used for protein purification can be used. For example, the humanized antibody can be purified by a combination of gel filtration, ion-exchange chromatography, ultrafiltration and the like. The molecular weight of the H chain or the L chain of the humanized antibody or the whole antibody molecule can be determined by polyacrylamide gel electrophoresis (hereinafter referred to as "PAGE") [*Nature*, 227, 680-685 (1970)], Western blotting [*Antibodies: A Laboratory Manual*, Cold Spring Harbor Laboratory, Chapter 12 (1988); *Monoclonal Antibodies: Principles and Practice*, Academic Press Limited (1996)], and the like.

(9) Evaluation of Binding Activity of Humanized Antibody and Antigen

The binding activity of the humanized antibody to the antigen can be evaluated by ELISA as described above.

3. Preparation of Antibody Fragment

The antibody fragment can be prepared based on the antibody as described in the above items 1 and 2 according to the genetically engineering method or the protein-chemical method.

The genetically engineering method includes a method in which a gene encoding an antibody fragment of interest is constructed and expression and purification are carried out using an appropriate host such as an animal cell, a plant cell, an insect cell, *Escherichia coli* or the like.

The protein-chemical method includes a method in which partially specific cleave, purification and the like are carried out using a protease such as pepsin or papain.

The production methods of antibody fragment including Fab, F(ab)$_2$, Fab', scFv, diabody and dsFv are specifically described.

(1) Preparation of Fab

Fab can be prepared protein-chemically by treating IgG with protease, papain. After the treatment with papain, if the original antibody is an IgG subclass having a binding property to protein A, it is possible to collect as a uniform Fab by passing through a protein A column to separate from IgG molecules and Fe fragments [*Monoclonal Antibodies: Principles and Practice*, third edition (1995)]. In the case of an antibody of an IgG subclass having no binding property to protein A, Fab can be collected by ion-exchange chromatography at a fraction eluted in low salt concentrations [*Monoclonal Antibodies: Principles and Practice*, third edition (1995)]. Also, Fab can also be often prepared genetic-engineeringly using *Escherichia coli*, and can be prepared using insect cells, animal cells or the like. For example, DNA encoding the V region of the antibody mentioned in 2(2), 2(4) and (5) of this item is cloned into a vector for expression of Fab to thereby prepare an Fab expression vector. Any vector for expression of Fab can be used, so long as DNA for Fab can be inserted and expressed. Examples include pIT 106 [*Science*, 240, 1041-1043 (1988)] and the like, The Fab expression vector is introduced into an appropriate *Escherichia coli* to thereby produce and accumulate Fab in an inclusion body or a periplasmic space. From the inclusion body, Fab having activity can be obtained by a refolding method generally used for proteins and, when expressed in periplasmic space, Fab having activity leaks out in a culture supernatant. After the refolding or from the culture supernatant, uniform Fab can be purified using a column to which an antigen is bound [*Antibody Engineering A Practical Guide*, W.H. Freeman and Company (1992)].

(2) Preparation of F(ab')$_2$

F(ab')$_2$ can be prepared protein-chemically by treating IgG with protease, pepsin. After the treatment with pepsin, it can be recovered as uniform F(ab')$_2$ by purifying operation in the same manner as Fab [*Monoclonal Antibodies: Principles and Practice*, third edition, Academic Press (1995)]. It can also be prepared by a method in which Fab' mentioned in the following 3(3) is treated with a maleimide such as o-PDM or bis-maleimide to form a thioether bond or by a method in which it is treated with DTNB [5,5'-dithiobis(2-nitrobenzoic acid)] to form an S—S bond [*Antibody Engineering, A Practical Approach*, IRL Press (1996)].

(3) Preparation of Fab'

Fab' can be prepared by treating F(ab')$_2$ described in the above 3(2) with a reducing agent such as dithiothreitol. Also, Fab' can be prepared by genetic-engineeringly *Escherichia coli*. Furthermore, it can be prepared using an insect cell, an animal cell and the like. For example, DNA encoding the V region of the antibody mentioned in 2(2), 2(4) and 2(5) of this item is cloned into a vector for expression of Fab' to thereby prepare an Fab' expression vector. With regard to the vector for expression of Fab', any vector may be used, so long as DNA for Fab' can be inserted and expressed. Examples include pAK19 [*Bio/Technology*, 10, 163-167 (1992)] and the like. The Fab' expression vector is introduced into an appropriate *Escherichia coli* to produce and accumulate Fab' in an inclusion body or periplasmic space. From the inclusion body, Fab' having activity can be obtained by a refolding method which is generally used in proteins and, when the Fab' is expressed in periplasmic space, it can be recovered extracellularly by disrupting the cell with treatment such as partial digestion by lysozyme, osmotic shock and sonication. After the refolding or from the disrupted cell solution, uniform Fab' can be purified using a protein G column or the like [*Antibody Engineering, A Practical Approach*, IRL Press (1996)].

(4) Preparation of scFv scFv can be prepared genetic-engineeringly using phages, *Escherichia coli*, insect cells, animal cells or the like. For example, DNA encoding the V region of the antibody mentioned in 2(2), 2(4) and 2(5) is cloned into a vector for expression of scFv to thereby prepare an scFv expression vector. Any vector for expression of scFv can be used, so long as DNA for scFv can be inserted and expressed. Examples include pCANTAB5E (manufactured by Pharmacia), pHFA

[*Human Antibodies & Hybridomas*, 5, 48-56 (1994)] and the like. When the scFv expression vector is introduced into an appropriate *Escherichia coli* and a helper phage is infected, a phage which expresses scFv on the phage surface in a fused form with the surface protein of the phage can be obtained. Also, scFv can be produced and accumulated in periplasmic space or an inclusion body of *Escherichia coli* into which the scFv expression vector is introduced. From the inclusion body, scFv having activity can be obtained by a refolding method generally used for proteins and, when scFv is expressed in periplasmic space, it can be recovered extracellularly by disrupting the cell with a treatment such as partial digestion by lysozyme, osmotic shock, sonication or the like. After the refolding or from the disrupted cell solution, uniform scFv can be purified using cation-exchange chromatography or the like [*Antibody Engineering, A Practical Approach*, IRL Press (1996)].

(5) Preparation of Diabody

Diabody can be often prepared genetic-engineeringly using *Escherichia coli*, or insect cells, animal cells or the like. For example, DNA in which VH and VL of the antibody described in 2(2), 2(4) and 2(5) of this item are linked so that amino acid residues encoded by its linker are 8 or less residues is prepared and cloned into a vector for expression of diabody to thereby prepare a diabody expression vector. Any vector for expression of diabody can be used, so long as DNA for diabody can be inserted and expressed. Examples include pCANTAB5E (manufactured by Pharmacia), pHFA [*Human Antibodies Hybridomas*, 5, 48 (1994)] and the like. Diabody can be produced and accumulated in periplasmic space or an inclusion body of *Escherichia coli* into which the diabody expression vector is introduced. From the inclusion body, diabody having activity can be obtained by a refolding method generally used for proteins and, when diabody is expressed in periplasmic space, it can be recovered extracellularly by disrupting the cell with a treatment such as partial digestion by lysozyme, osmotic shock, sonication or the like. After the refolding or from the disrupted cell solution, uniform diabody can be purified using cation-exchange chromatography or the like [*Antibody Engineering, A Practical Approach*, IRL Press (1996)].

(6) Preparation of dsFv dsFv can be often prepared genetic-engineeringly using *Escherichia coli*, or an insect cell, an animal cell or the like. Firstly, mutation is introduced into an appropriate position of DNAs encoding VH and VL of the antibody mentioned in 2(2), 2(4) and 2(5) of this item to prepare DNAs in which an encoded amino acid residue is replaced with cysteine. Each DNA prepared is cloned into a vector for expression of dsFv to thereby prepare an expression vector of VH and VL. Any vector can be used as a vector for expression of dsFv may be used, so long as DNA for dsFv can be inserted and expressed. Examples include pULI 9 [*Protein Engineering*, 7, 697-704 (1994)] and the like. The expression vector of VH and VL is introduced into an appropriate *E. coli* and dsFv is formed and accumulated in an inclusion body or periplasmic space. VH and VL are obtained from the inclusion body or periplasmic space, mixed and subjected to a refolding method generally used for proteins to thereby obtain dsFv having activity. After the refolding, it can be further purified by ion-exchange chromatography, a gel filtration or the like. [*Protein Engineering*, 7, 697-704 (1994)].

4. Pharmaceutical and Therapeutic Agent in the Present Invention

The pharmaceutical agent comprising the monoclonal antibody of the present invention as an active ingredient can be used for treating various diseases relating to HB-EGF.

The diseases related to HB-EGF include cancer, heart disease, arteriosclerosis and the like. The cancer includes solid cancer such as breast cancer, hepatic cancer, pancreatic cancer, bladder cancer, ovarian cancer and ovarian germ cell tumor. Also, it includes metastatic cancer caused by continuous, hematogenous or lympocytic metastasis accompanied with any of the solid cancers, peritoneal dissemination or the like. Furthermore, it includes other cancers such as cancers derived from hematopoietic cells (hematological cancer or blood cancer) including leukemia (acute myelocytic leukemia, T-cell leukemia, etc.), lymphoma, myeloma, and the like.

The pharmaceutical agent comprising the antibody or antibody fragment of the present invention as an active ingredient is preferably supplied as a pharmaceutical preparation produced by an appropriate method well known in the technical field of pharmaceutics, by mixing it with one or more pharmaceutically acceptable carriers.

It is preferred to select a route of administration which is most effective in treatment. Examples include oral administration and parenteral administration, such as buccal, tracheal, rectal, subcutaneous, intramuscular or intravenous administration. In the case of an antibody or peptide formulation, intravenous administration is preferred. The dosage form includes sprays, capsules, tablets, granules, syrups, emulsions, suppositories, injections, ointments, tapes and the like.

The pharmaceutical preparation suitable for oral administration includes emulsions, syrups, capsules, tablets, powders, granules and the like. Liquid preparations such as emulsions and syrups can be produced using, as additives, water; sugars such as sucrose, sorbitol and fructose; glycols such as polyethylene glycol and propylene glycol; oils such as sesame oil, olive oil and soybean oil; antiseptics such as p-hydroxybenzoic acid esters; flavors such as strawberry flavor and peppermint; and the like. Capsules, tablets, powders, granules and the like can be produced using, as additives, excipients such as lactose, glucose, sucrose and mannitol; disintegrating agents such as starch and sodium alginate; lubricants such as magnesium stearate and talc; binders such as polyvinyl alcohol, hydroxypropylcellulose and gelatin; surfactants such as fatty acid ester; plasticizers such as glycerin; and the like.

The pharmaceutical preparation suitable for parenteral administration includes injections, suppositories, sprays and the like. Injections can be prepared using a carrier such as a salt solution, a glucose solution or a mixture of both thereof. Suppositories can be prepared using a carrier such as cacao butter, hydrogenated fat or carboxylic acid. Sprays can be prepared using the antibody or antibody fragment as such or using it together with a carrier which does not stimulate the buccal or airway mucous membrane of the patient and can facilitate absorption of the compound by dispersing it as fine particles. The carrier includes lactose, glycerol and the like. Depending on the properties of the antibody and the carrier, it is possible to produce pharmaceutical preparations such as aerosols and dry powders. In addition, the components exemplified as additives for oral preparations can also be added to the parenteral preparations.

Although the dose or the frequency of administration varies depending on the objective therapeutic effect, administration method, treating period, age, body weight and the like, it is usually 10 μg/kg to 8 mg/kg per day and per adult.

The present invention is explained below in detail based on Examples; however, Examples are illustrations of the present invention and the present invention is not limited thereto.

Example 1

Preparation of Anti-HB-EGF Monoclonal Antibody (1) Preparation of Immunogen

A freeze-dried preparation of recombinant secretory human HB-EGF manufactured by R & D System (catalogue number 259-HE/CF) was dissolved in Dulbecco's phosphate buffer (phosphate-buffered saline: PBS) and used as the immunogen.

(2) Immunization of Animal and Preparation of Antibody-Producing Cell

To an HB-EGF deficient mouse [obtained from Department of Cell Biology, Research Institute for Microbial Diseases, Osaka University, *PNAS*, Vol. 100, No. 100, 3221-3226 (2003)], 25 μg of the recombinant secretory human HB-EGF prepared in Example 1(1) was administered, together with 2 mg of aluminum hydroxide adjuvant (*Antibodies-A Laboratory Manual*, Cold Spring Harbor Laboratory, p. 99, 1988) and $1 \times 10^9$ cells of pertussis vaccine (Chiba Serum Institute). Two weeks after the administration, 25 μg of the HB-EGF alone was administered once a week and 4 times as a total. Blood was partially collected from the venous plexus of the fundus of the eye, its serum antibody titer was examined by an enzyme immunoassay shown below, and 3 days after the final immunization, the spleen was extracted from a mouse which showed sufficient antibody titer. The spleen was cut to pieces in MEM (minimum essential medium) medium (manufactured by Nissui Pharmaceutical), and the cells were unbound using a pair of forceps and centrifuged (1,200 rpm, 5 minutes). The thus obtained precipitate fraction was treated with Tris-ammonium chloride buffer (pH 7.6) for 1 to 2 minutes to eliminate erythrocyte. The thus obtained precipitation fraction (cell fraction) was washed three times with MEM and used in the cell fusion, (3) Enzyme Immunoassay (Binding ELISA)

The recombinant human HB-EGF of Example 1(1) was dispensed into a 96 well plate for ELISA (manufactured by Greiner) at 0.5 μg/ml and 50 μl/well, was allowed to stand overnight at 4° C. for adsorption and was used in the assay. After washing the plate, 1% bovine serum albumin (BSA)-PBS was added thereto at 50 μl/well and allowed to stand at room temperature for 1 hour to block the remaining active groups. After the plate was allowed to stand, 1% BSA-PBS was discarded, and as the primary antibody, antiserum of a mouse to be immunized or a hybridoma culture supernatant was dispensed at 50 μL/well into the plate and was allowed to stand for 2 hours. After washing the plate with 0.05% polyoxyethylene (20) sorbitan monolaurate [(corresponds to Tween 20, a trademark of ICI, manufactured by Wako Pure Chemical Industries)]/PBS (hereinafter referred to "Tween-PBS"), a peroxidase-labeled rabbit anti-mouse IgG gamma chain (manufactured by Kirkegarrd & Perry Laboratories) was added as the secondary antibody at 50 μl/well and was allowed to stand at room temperature for 1 hour, After washing the plate with Tween-PBS, ARTS [2,2-azinobis(3-ethylbenzothiazole-6-sulfonic acid) ammonium] substrate solution [1 mmol/l ABTS/0.1 mol/l citrate buffer (pH 4.2), 0.1% $H_2O_2$] was added to develop color, and the absorbance at OD 415 nm was measured using a plate reader (Emax; manufactured by molecular Devices).

(4) Preparation of Mouse Myeloma Cell

An 8-azaguanine-resistant mouse myeloma cell line P3X63Ag8U.1 (P3-U1: purchased from ATCC) was cultured in 10% fetal bovine serum-supplemented RPMI 1640 (manufactured by Invitrogen), and $2 \times 10^7$ or more of cells were ensured on the day of cell fusion and were used for the cell fusion as the parent cell line.

(5) Preparation of Hybridoma

The mouse spleen cell obtained in Example 1(2) and the myeloma cell obtained in Example 1(4) were mixed at a ratio of 10:1, followed by centrifugation (1,200 rpm, 5 minutes). A group of cells of the thus obtained precipitation fraction were thoroughly loosened, and then, while stirring, a mixed solution of 1 g of polyethylene glycol-1000 (PEG-1000), 1 ml of MEM medium and 0.35 ml of dimethyl sulfoxide was added at 37° C. in an amount of 0.5 ml per $10^8$ mouse spleen cells, 1 ml of MEM medium was added to the suspension several times at an interval of 1 to 2 minutes, and then the total volume was adjusted to 50 ml by adding MEM medium. The suspension was centrifuged (900 rpm, 5 minutes), cells of the thus obtained precipitation fraction were gently loosened, and then the cells were suspended in 100 ml of HAT medium [a medium prepared by adding HAT Media Supplement (manufactured by Invitrogen) to the 10% fetal bovine serum-supplemented RPMI 1640 medium], gently through their sucking in and sucking out by a pipette. The suspension was dispensed into a 96 well culture plate at 200 μl/well, followed by culturing at 37° C. for 10 to 14 days in a 5% $CO_2$ incubator. After the culturing, wells which responded to the recombinant human HB-EGF were selected by examining the culture filtrates by the enzyme immunoassay described in Example 1(3), and cloning by limiting dilution method from the cells contained therein was repeated twice to thereby establish anti-HB-EGF monoclonal antibody-producing hybridoma cell lines KM3566, KM3567 and KM3579.

(6) Purification of Monoclonal Antibody

Each of the hybridoma cell lines obtained in Example 1(5) was intraperitoneally injected into pristine-treated 8-week-old female nude mice at a dose of 5 to $20 \times 10^6$ cells/animal. From 10 to 21 days thereafter, ascitic fluid (from 1 to 8 ml/animal) was collected from each mouse in which ascitic fluid was accumulated caused by ascites tumor of the hybridoma. The ascitic fluid was centrifuged (3,000 rpm, 5 minutes) to remove solids, Purified IgG monoclonal antibodies were obtained by purifying them according to the caprylic acid precipitation method (*Antibodies-A Laboratory Manual*, Cold Spring Harbor Laboratory, 1988). Subclass of each monoclonal antibody was determined by ELISA using a subclass typing kit. Subclass of the monoclonal antibody KM3566 was IgG 1, subclass of the monoclonal antibody KM3567 was IgG1 and that of the monoclonal antibody KM3579 was IgG2b.

Example 2

Reactivity of Anti-HB-EGF Monoclonal Antibody for HB-EGF (1) Reactivity with HB-EGF by Binding ELISA This experiment was carried out in accordance with the method shown in Example 1(3), Each of purified antibodies of anti-HB-EGF monoclonal antibodies KM3566, KM3567, KM3579, a commercially available anti-HB-EGF monoclonal antibody MAB259 (manufactured by R & D) and a negative control antibody KM511 (an anti-G-CSF derivative monoclonal antibody) was diluted stepwise from 10 μg/ml by 5-fold serial dilution and used as the primary antibody. The results are shown in FIG. 1A.

Each of the anti-HB-EGF monoclonal antibodies KM3566, KM3567, KM3579 and MAB259 reacted with the recombinant human HB-EGF and did not react with BSA.

(2) Reactivity with HB-EGF by Western Blotting

Twenty ng per lane of the recombinant human HB-EGF (manufactured by R & D) was fractionated by SDS-polyacrylamide electrophoresis, and the gel after electrophoresis was transferred on a PVDF membrane. After blocking the membrane with 10% BSA-PBS, each of the purified antibodies of anti-HB-EGF monoclonal antibodies KM3566, KM3567, KM3579, MAB259 and the negative control antibody KM511 was diluted to 1 μg/ml using 10% BSA-PBS and was allowed to react at room temperature for 2 hours. After thoroughly washing the membrane with Tween-PBS, a peroxidase-labeled anti-mouse immunoglobulin antibody (manufactured by Zymed Laboratory) was diluted and was allowed to react at room temperature for 1 hour. The membrane was thoroughly washed with Tween-PBS, bands were detected using ECL™ Western blotting detection reagents (manufactured by Amersham Pharmacia).

A band of approximately from 15 to 30 kilo daltons (hereinafter referred to as "kDa") corresponding to the molecular weight of the recombinant secretory human HB-EGF was detected from each of the anti-HB-EGF monoclonal antibodies KM3566, KM3567, KM3579 and MAB259.

(3) Evaluation of HB-EGF-EGFR Binding Inhibition Activity of Anti-HB-EGF Monoclonal Antibodies The HB-EGF-EGFR binding inhibition activity of anti-HB-EGF monoclonal antibodies KM3566, KM3567, KM3579 and MAB259 was examined using 32D/EGFR cell and biotin-labeled HB-EGF.

The recombinant secretory human HB-EGF was biotin-labeled in the usual way using EZ-Link Sulfo-NHS-Biotin (manufactured by Pierce).

Each of the KM3566, KM3567, KM3579 and MAB259 was diluted stepwise from 10 μg/ml by 5-fold serial dilution and dispensed into a 96 well plate at 50 μl/well. Thereafter, the 32D/EGFR cell was dispensed at $1 \times 10^4$ cells/50 μl/well. Furthermore, biotin-labeled HB-EGF and Alexa 647-labeled streptoavidin were diluted to optimum concentrations and dispensed at 10 μl/well and 50 μl/well, respectively, and after mixing, the mixture was allowed to react at room temperature for 3 hours under shade. A wavelength of 650 nm to 685 nm excited by a laser radiation 633 nm He/Ne was measured using 8200 cellular Detection System (manufactured by Applied Biosystems).

Figure 1B:
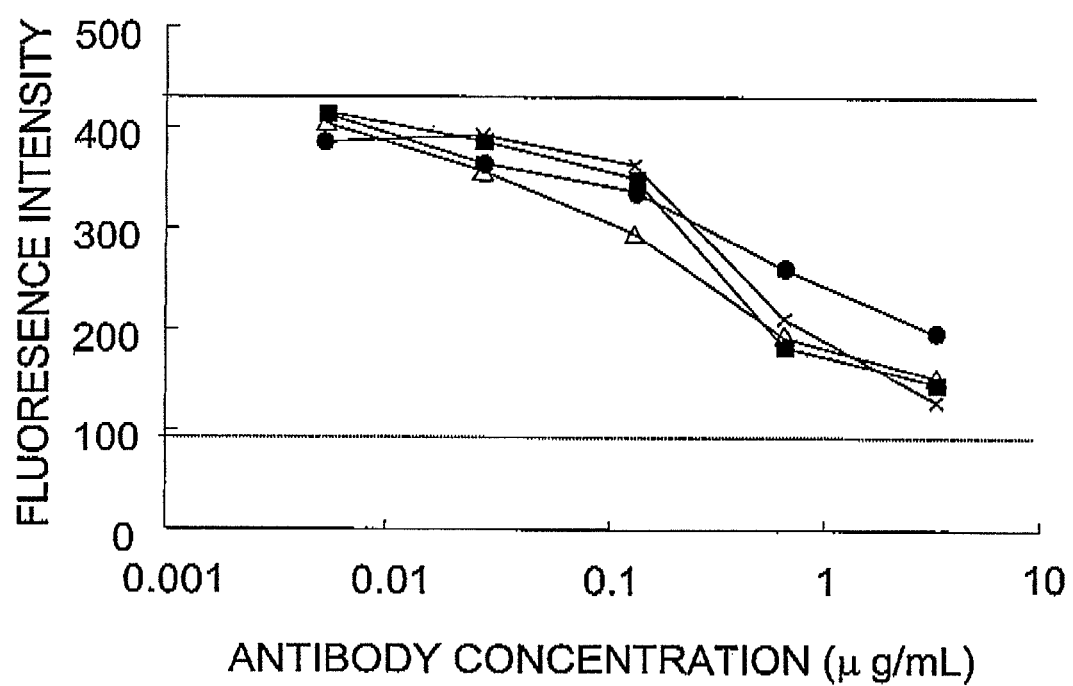
FIG. 1B shows the HB-EGF-EGFR binding inhibition activity of the anti-HB-EGF monoclonal antibodies KM3566, KM3567, KM3579 and MAB259, The abscissa shows the concentration of each antibody, and the ordinate shows the binding of biotin-labeled HB-EGF, shown by fluorescence intensity. The sidewise solid line shows fluorescence intensity at the time when biotin-labeled HB-EGF was added and when the antibody was not added, and the sidewise dotted line shows fluorescence intensity at the time when biotin-labeled HB-EGF was not added and when the antibody was not added. Δ shows monoclonal antibody KM3566, X shows monoclonal antibody KM3567, ● shows monoclonal antibody KM3579, and ■ shows monoclonal antibody MAB259.

As a result, as shown in FIG. 1B, all of the KM3566, KM3567, KM3579 and MAB259 antibody concentration-dependently inhibited binding of biotinylated HB-EGF to EGFR. Accordingly, it was found that all of the anti-HB-EGF monoclonal antibodies inhibit binding of HB-EGF with EGFR.

Example 3

Examination of Neutralization Activity of Anti-HB-EGF Monoclonal Antibodies for HB-EGF Neutralization activity of anti-HB-EGF monoclonal antibodies KM3566, KM3567, KM3579 and MAB259 was examined by a cell growth inhibition assay which used an HB-EGF-dependent cell. A cell line constructed by transferring the EGFR gene into a mouse bone marrow-derived cell line 32D clone 3 (ATCC CRL-11345) (hereinafter referred to as "32D/EGFR") was used as the HB-EGF-dependent cell. Each of purified antibodies of the anti-HB-EGF monoclonal antibodies KM3566, KM3567, KM3579 and MAB259 and a negative control antibody KM511 was serially diluted from 20 μg/ml by 3- to 4-fold dilution and dispensed into a 96 well plate at 50 μl/well. Next, 0.1 μg/ml of recombinant human HB-EGF (manufactured by R & D) was dispensed at 10 μl/well, and after mixing, the mixture was allowed to react on ice for 2 hours. Thereafter, the 32D/EGFR cell was seeded at cell number of $1 \times 10^4$ cells/40 μl/well, followed by culturing for 36 hours. A viable cell measuring reagent SF (manufactured by Nacalai Tesque) was added at 10 μl/well, and 2 hours thereafter, the absorbance at OD 450 nm was measured using a plate reader (Emax; manufactured by Molecular Devices).

Figure 2A:
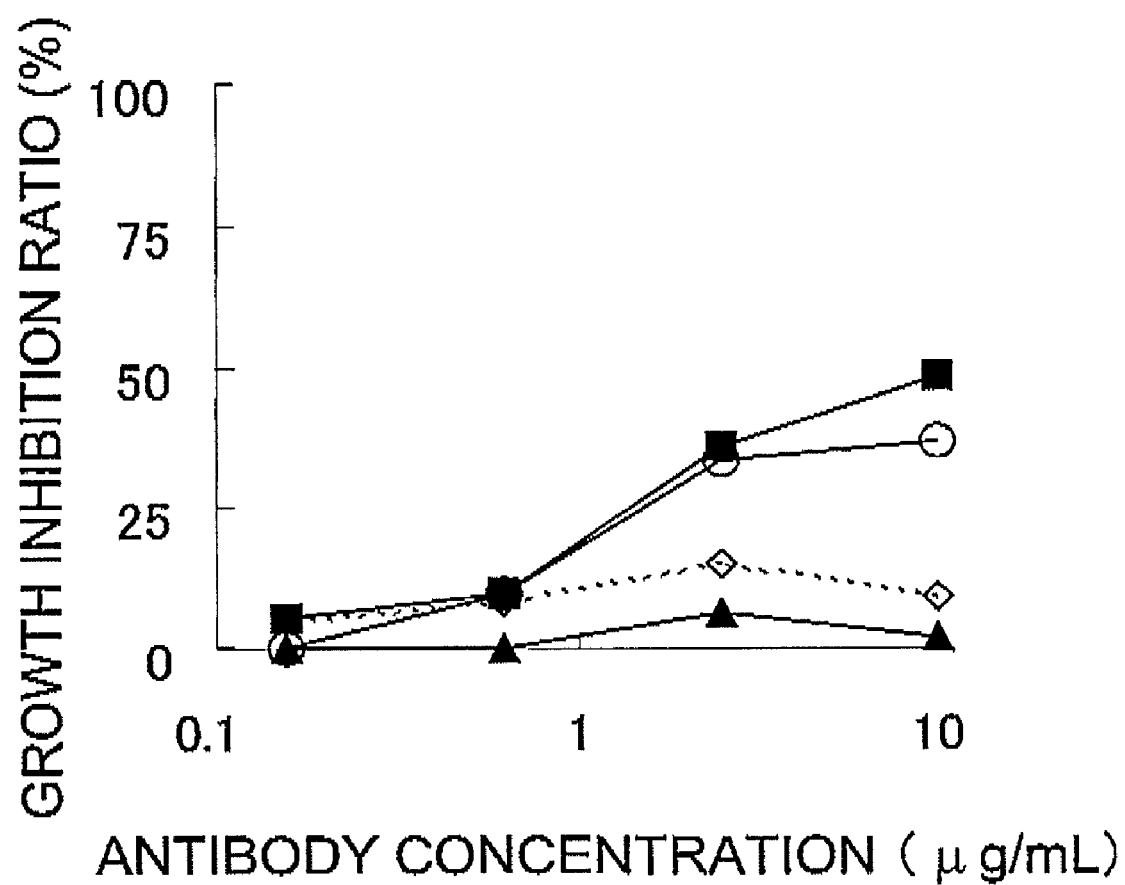
FIG. 2A shows the HB-EGF neutralization activity of various anti-HB-EGF monoclonal antibodies. The abscissa shows the concentration of each antibody, and the ordinate shows the growth inhibition ratio (%). ◊ shows monoclonal antibody KM511, ■ shows monoclonal antibody KM3566, ▲ shows monoclonal antibody KM3579, and ◇ shows monoclonal antibody MAB259, respectively.

By regarding the absorbance of an only HB-EGF-added well as 0% inhibition ratio, and the absorbance of a no-HB-EGF and no-antibody added well as 100% inhibition ratio, and cell growth inhibition ratio of each well was calculated, with the results shown in FIG. 2A. As a result, KM3566 showed HB-EGF-dependent cell growth inhibition activity for the cell line 32D/EGFR, similar to the level of MAB259. Accordingly, it was found that the two antibodies have similar level of HB-EGF neutralization activity. On the other hand, since KM3579 did not inhibit growth of the cell line 32D/EGFR, it was found that it has no HB-EGF neutralization activity.

Figure 2B:
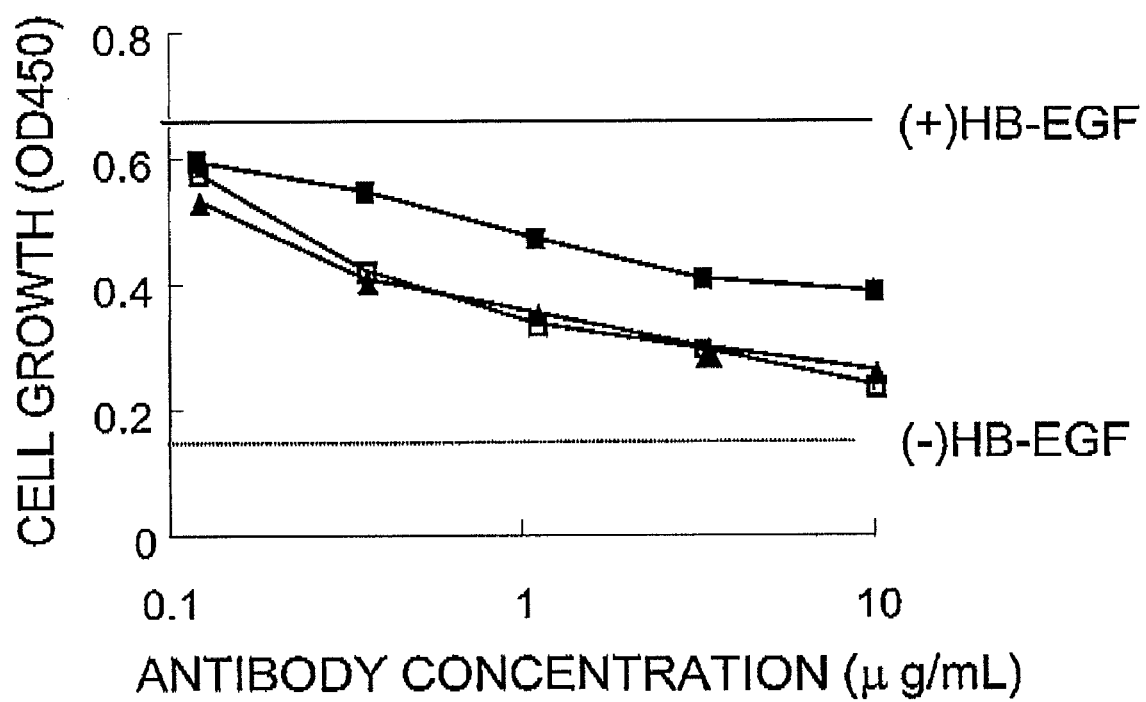
FIG. 2B shows the HB-EGF neutralization activity of various anti-HB-EGF monoclonal antibodies. The abscissa shows the concentration of each antibody, and the ordinate shows the cell growth. HB-EGF(+) shows the cell growth at the time when HB-EGF was added and when the antibody was not added, and FIB-EGF(−) shows the cell growth at the time when HB-EGF was not added and the antibody was not added. □ shows monoclonal antibody MAB259, ■ shows monoclonal antibody KM3567 and ▲ shows monoclonal antibody KM3566.

In addition, results of the examination of the neutralization activity of KM3567 carried out in the same manner are shown in FIG. 2B. As a result, although its activity was weak in comparison with KM3566, KM3567 had the activity to inhibit HB-EGF-dependent cell growth.

Example 4

Examination of Reactivity of Anti-HB-EGF Monoclonal Antibodies for Membrane Type HB-EGF Each of the anti-HB-EGF monoclonal antibodies KM3566, KM3567, KM3579, MAB259 and the negative control antibody KM511 was diluted with 0.1% BSA-PBS to respective concentrations and added to 1 to $5 \times 10^5$ cells of a human gastric cancer cell line MKN-28 (HSRRB JCRB 0253), a human ovarian cancer cell line ES-2 (ATCC CRL-1978) or a human breast cancer cell line MDA-MB-231 (ATCC HTB-26), and after mixing, the total volume was adjusted to 50 μl. Each of these cell suspensions was allowed to react on ice for 40 minutes and then washed three times with 0.1% BSA-PBS. To the cells, 50 μl of an FITC-labeled goat anti-mouse IgG+IgM (H+L) polyclonal antibody (manufactured by Kirkegaard & Perry Laboratories) prepared by diluting with 0.1% BSA-PBS was added and the mixture was allowed to react on ice for 40 minutes, The cells were washed with 0.1% BSA-PBS and then suspended in 0.1% BSA-PBS, and the fluorescence intensity was measured using a flow cytometer (manufactured by Coulter).

Figure 3:
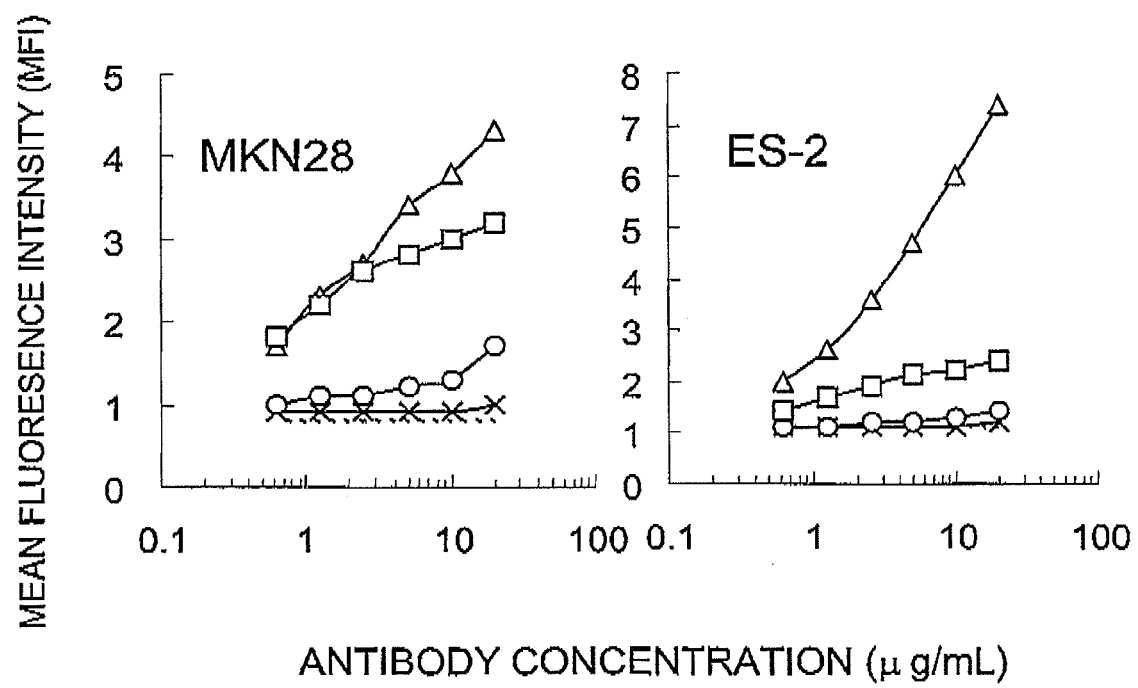
FIG. 3 shows the reactivity of various anti-HB-EGF monoclonal antibodies by FCM analysis. The abscissa shows the concentration of each antibody, and the ordinate shows the mean fluorescence intensity. X shows monoclonal antibody KM511, Δ shows monoclonal antibody KM3566, □ shows monoclonal antibody KM3579, and ○ shows monoclonal antibody MAB259.
Figure 4:
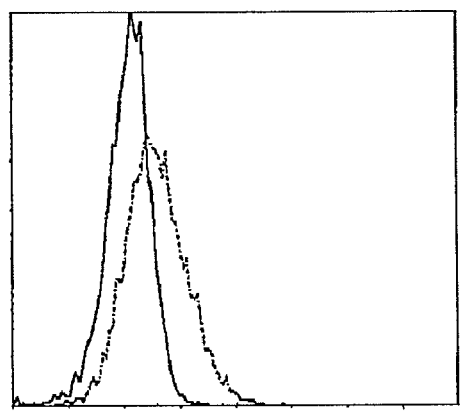
FIG. 4 shows the reactivity of various anti-HB-EGF monoclonal antibodies for MDA-MB-231 cell by FCM analysis. In each histogram, the solid line shows negative control antibody KM511, and the dotted line shows each anti-HB-EGF antibody. (a), (b), (c) and (d) show MAB529, KM3566, KM3567 and KM3579, respectively.
Figure 4:
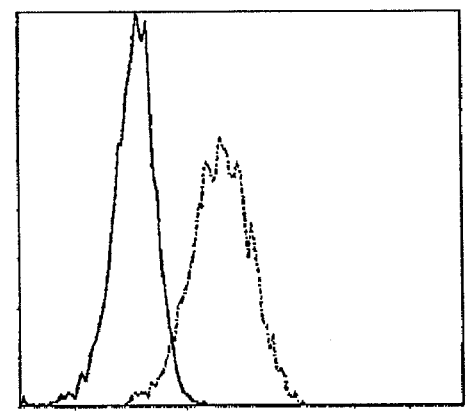
Figure 4:
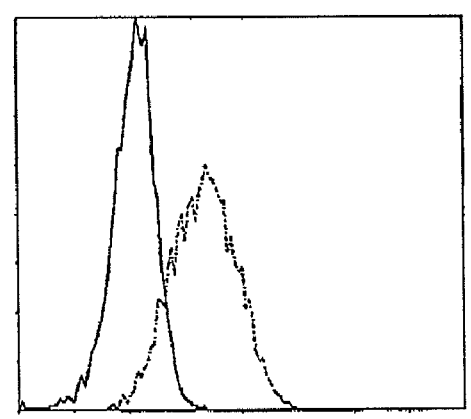
Figure 4:
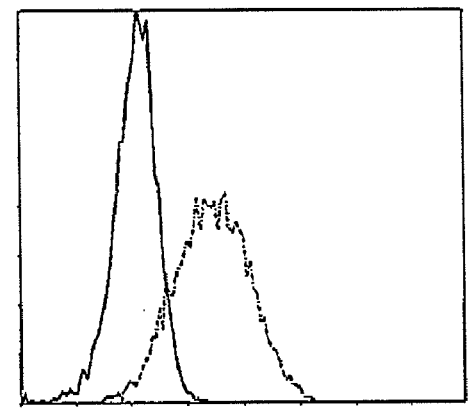

FIG. 3 shows the mean fluorescence intensity (MFI value), when each of the above-mentioned monoclonal antibodies was diluted 2-fold from 20 μg/ml and allowed to react with MKN-28 and ES-2, FIG. 4 shows a histogram of each antibody reactivity, when 20 μg/ml of each of the above-mentioned monoclonal antibodies was allowed to react with the human breast cancer cell line MDA-MB-231. As a result, regarding MKN-28, binding activity of KM3566 and KM3579 was found. Also, in the case of ES-2, the binding activity was found in order of KM3566>KM3579. Furthermore, in the case of MDA-MB-231, the binding activity was found in order of KM3566>KM3567 KM3579. In addition, in all of cells, the MFI value of MAB259 was similar to the negative control antibody KM511 and antibody-not-added negative control, and MAB259 hardly bound to cells. From the above result, it was found that the monoclonal antibodies KM3566, KM3567 and KM3579 bind to the membrane type and cell membrane-bound HB-EGF of cancer cell lines.

Example 5

Isolation and Analysis of cDNA Encoding Variable Region of Anti-HB-EGF Monoclonal Antibody (1) Preparation of mRNA from Anti-HB-EGF Monoclonal Antibody-Producing Hybridoma Cell About 4.8 µg of mRNA was prepared from $5 \times 10^7$ of hybridoma cells of the hybridoma KM3566 described in Example 1, using RNAeasy Maxi kit (manufactured by QIAGEN) and Oligotex™-dt30 <Super> mRNA Purification Kit (manufactured by Takara) and in accordance with the instructions attached thereto.

(2) DNA Cloning of H Chain and L Chain Variable Regions of Anti-HB-EGF Monoclonal Antibody KM3566

Using BD SMART™ RACE cDNA Amplification Kit (manufactured by BD Biosciences) in accordance with the instructions attached thereto, a cDNA having the BD SMART II™ A Oligonucleotide sequence attached to the kit, on the 5' terminal, was obtained from 1 µg of the mRNA of the anti-HB-EGF monoclonal antibody KM3566 obtained in Example 5(1). Using this cDNA as the template, and using the universal primer Amix attached to the kit and a mouse Ig(γ)-specific primer having the nucleotide sequence represented by SEQ ID NO:6, PCR was carried out to amplify a cDNA fragment of VH. Also, a cDNA fragment of VL was amplified by carrying out PCR using a mouse Ig(κ)-specific primer having the nucleotide sequence represented by SEQ ID NO:7 instead of the Ig(γ)-specific primer. After heating at 94° C. for 5 minutes, the PCR was carried out by 5 cycles consisting of reactions at 94° C. for 30 seconds and at 72° C. for 3 minutes, 5 cycles consisting of reactions at 94° C. for 30 seconds, at 70° C. for 30 seconds and at 72° C. for 3 minutes, and 30 cycles consisting of reactions at 94° C. for 30 seconds, at 68° C. for 30 seconds and at 72° C. for 3 minutes, followed by reaction at 72° C. for 10 seconds. The PCR was carried out using PTC-200 DNA Engine (manufactured by Bio-Rad).

In order to clone the thus obtained PCR products and determine their nucleotide sequences, they were separated by agarose gel electrophoresis, and the PCR products of H chain and L chain, each having about 600 bp, were extracted using Gel Extraction Kit (manufactured by QIAGEN). Each of the thus obtained extraction fragments was ligated to a SmaI-digested pBluescript II SK(-) vector using Ligation High (manufactured by TOYOBO), and then an *Escherichia coli* strain DH5α was transformed by the method of Cohen et al. [*Proc. Natl. Acad. Sci. USA*, 69, 2110 (1972)]. Plasmids were extracted from the obtained transformants using an automatic plasmid extraction device (manufactured by KURABO) and were allowed to react using BigDye Terminator Cycle Sequencing FS Ready Reaction Kit (manufactured by PE Biosystems) in accordance with the instructions attached thereto, and then nucleotide sequences of the cloned PCR products were analyzed by a sequencer ABI PRISM 3700 of the same company. As a result, a plasmid KM3566VH10G2 containing complete length H chain cDNA and a plasmid KM3566VL10K2 containing L chain cDNA, wherein ATG sequence considered to be the initiation codon is present in the cDNA 5' terminal, were obtained.

(3) Analysis of Amino Acid Sequences of Anti-HB-EGF Monoclonal Antibody V Region Complete nucleotide sequence of VH contained in the plasmid KM3566VH10G2 is shown in SEQ ID NO:8, and complete amino acid sequence of VH containing a signal sequence, deduced from the sequence, in SEQ ID NO:9, complete nucleotide sequence of VL contained in the plasmid KM3566VL10K2 in SEQ ID NO:10, and complete amino acid sequence of VL containing a signal sequence, deduced from the sequence, in SEQ ID NO:11. Based on the comparison with known sequence data of mouse antibodies [*SEQUENCES of Proteins of Immunological Interest*, US Dept. Health and Human Services (1991)] and the comparison with the results of analysis of N-terminal amino acid sequences of H chain and L chain of purified anti-HB-EGF monoclonal antibody KM3566 using a protein sequencer (manufactured by Shimadzu Corp.: PPSQ-10), it was found that the isolated respective cDNA is a complete length cDNA encoding the anti-HB-EGF monoclonal antibody KM3566 containing a secretion signal sequence, and the amino acid sequence at positions 1 to 19 in the amino acid sequence represented by SEQ ID NO:9 is the secretion signal sequence regarding the H chain and the amino acid sequence at positions 1 to 20 in the amino acid sequence represented by SEQ ID NO:11 is the secretion signal sequence regarding the L chain.

Next, the novelty of the VH and VL of anti-HB-EGF monoclonal antibody KM3566 was examined. Using GCG Package (version 9.1, manufactured by Genetic Computer Group) as a sequence analyzing system, existing protein amino acid sequence data base was retrieved by the BLASTP method [*Nucleic Acids Res.*, 25, 3389 (1997)]. As a result, completely coinciding amino acid sequences were not found for the VH and VL, thus confirming that the VII and VL of anti-HB-EGF monoclonal antibody KM3566 have novel amino acid sequences.

In addition, CDRs of the VII and VL of anti-HB-EGF monoclonal antibody KM3566 were identified by comparing with amino acid sequences of known antibodies. Amino acid sequences of CDR1, CDR2 and CDR3 of the VH of anti-HB-EGF monoclonal antibody KM3566 are shown in SEQ ID NOs:12, 13 and 14, respectively, and amino acid sequences of CDR1, CDR2 and CDR3 of the VL are shown in SEQ ID NOs:15, 16 and 17, respectively.

Example 6

Preparation of Anti-HB-EGF Chimeric Antibody (1) Construction of Anti-HB-EGF Chimeric Antibody Expression Vector pKANTEX3566

Using the humanized antibody expression vector pKANTEX93 described in WO 97/10354 and the plasmids KM3566VH10G2 and KM3566VL10K2 obtained in Example 5(2), an anti-HB-EGF chimeric antibody expression vector pKANTEX3566 was constructed in the following manner.

Figure 5:
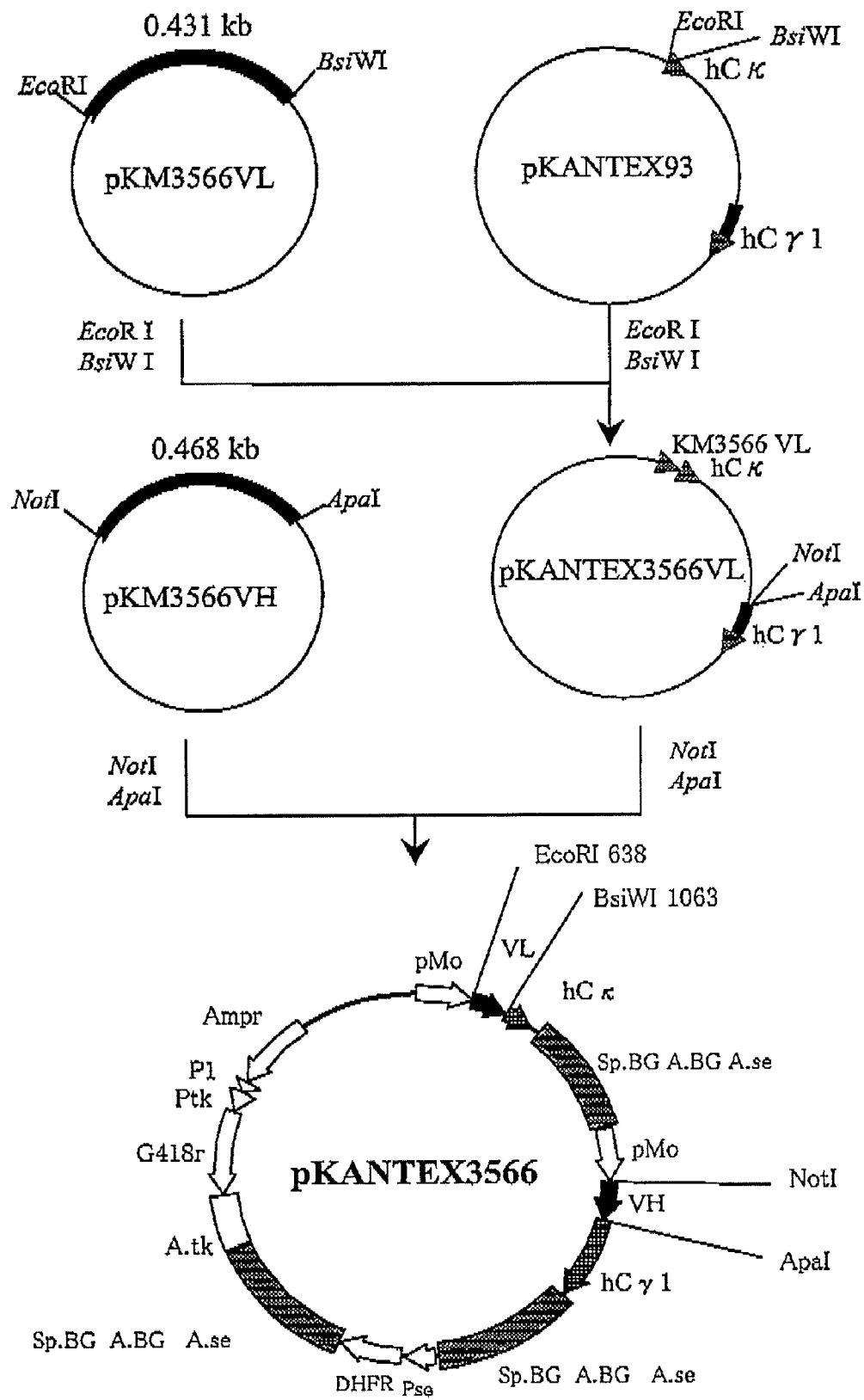
FIG. 5 shows construction steps of an anti-HB-EGF chimeric antibody expression vector pKANTEX3566.

Using 100 ng of the plasmid KM3566VH10G2 as the template, 100 µl in total volume of a solution consisting of 10 µl of 10×KOD buffer, 10 µl of 2 mmol/l dNTP, 2 µl of 25 mmol/l magnesium chloride, 1 µl of each of 10 µmol/l of primers having the nucleotide sequences described in SEQ ID NOs:18 and 19 and 1 µl of KOD polymerase (manufactured by TOYOBO) was heated at 96° C. for 3 minutes, followed by 25 cycles consisting of reactions at 94° C. for 1 minute, at 55° C. for 1 minute and at 72° C. for 1 minute, further followed by reaction at 72° C. for 8 minutes. By this reaction, a cDNA encoding the VH of KM3566 comprising a restriction enzyme recognizing sequence for inserting into pKANTEX93 was synthesized. In the same manner, 100 µl in total volume of a solution consisting of 100 ng of the plasmid KM3566VL10K2 as the template, 10 µl of 10×KOD buffer, 10 µl of 2 mmol/l dNTP, 2 µl of 25 mmol/l magnesium chloride, 1 µl of each of 10 µmol/l of primers having the nucleotide sequences represented by SEQ ID NOs:20 and 21 and 1 µl of KOD polymerase (manufactured by TOYOBO) was heated at 96° C. for 3 minutes, followed by 25 cycles consisting of reactions at 94° C. for 1 minute, at 55° C. for 1 minute and at 72° C. for 1 minute, further followed by reaction at 72° C. for 8 minutes. By this reaction, a cDNA encoding the VL of KM3566 comprising a restriction enzyme recognizing sequence for inserting into pKANTEX93 was synthesized. By purifying and concentrating each of the PCR products by ethanol precipitation and cloning it into the SmaI-digested pBluescript II SK(−), a plasmid pKM3566VH containing a nucleotide sequence encoding the VH of KM3566 and a plasmid pKM3566VL containing a nucleotide sequence encoding the VL of KM3566 were obtained. Next, a restriction enzyme BsiWI (manufactured by New England Biolabs) was added to each of the vector pKANTEX93 and the pKM3566VL obtained in the above, followed by reaction at 55° C. for 1 hour, and then a restriction enzyme EcoRI (manufactured by Takara) was added thereto, followed by reaction at 37° C. for 1 hour. This reaction solution was subjected to agarose gel electrophoresis, and then each of a pKANTEX93 EcoRI-BsiWI fragment of about 12.8 kb and a VL EcoRI-BsiWI fragment of about 0.43 kb was recovered using QIAquick Gel Extraction Kit (manufactured by QIAGEN). The thus obtained two fragments were ligated using Ligation High (manufactured by TOYOBO) in accordance with the instructions attached thereto, and *E. coli* DH5α (manufactured by TOYOBO) was transformed using the thus obtained recombinant plasmid DNA solution. By preparing each plasmid DNA from clones of transformant and confirming it by restriction enzyme treatment, a plasmid pKANTEX3566VL comprising the intended EcoRI-BsiWI fragment of about 0.43 kb was obtained. Next, a restriction enzyme ApaI (manufactured by Takara) was added to each of the pKANTEX3566VL and pKM3566VH obtained in the above, followed by reaction at 37° C. for 1 hour, and then a restriction enzyme NotI (manufactured by New England Biolabs) was further added thereto, followed by reaction at 37° C. for 1 hour. This reaction solution was fractionated by agarose gel electrophoresis to recover ApaI-NotI fragments, a pKANTEX3566VL of about 13.2 kb and a VH of about 0.47 kb, were respectively recovered. The thus obtained two fragments were ligated using Ligation High (manufactured by TOYOBO) in accordance with the instructions attached thereto, and *E. coli* DH5α (manufactured by TOYOBO) was transformed using the thus obtained recombinant plasmid DNA solution. By preparing each plasmid DNA from clones of transformant and confirming it by restriction enzyme treatment, a plasmid pKANTEX3566 comprising the intended ApaI-NotI fragment of about 0.47 kb was obtained. Regarding the plasmid, after the reaction using BigDye Terminator Cycle Sequencing FS Ready Reaction Kit (manufactured by PE Biosystems) in accordance with the instructions attached thereto, the nucleotide sequence was analyzed by a sequencer ABI PRISM 3700 of the same company. As a result, an anti-HB-EGF chimeric antibody expression vector pKANTEX3566 cloned with the intended cDNA encoding the VH of KM3566 and cDNA encoding its VL was obtained. Schematic illustration of the vector structure is shown in FIG. 5.

(2) Expression of Anti-HB-EGF Chimeric Antibody in Animal Cell

Using the anti-HB-EGF chimeric antibody expression vector pKANTEX3566 obtained in the above-mentioned (1), the anti-HB-EGF chimeric antibody was expressed in an animal cell by a usual method [*Antibody Engineering, A Practical Guide*, W.H. Freeman and Company (1992)] to obtain an anti-HB-EGF chimeric antibody-producing transformant KM3966.

(3) Preparation of Purified Chimeric Antibody

After culturing the transformant KM3966 obtained in the above-mentioned (2) by a general culturing method, the cell suspension was recovered and centrifuged at 3,000 rpm and 4° C. for 10 minutes, and then the thus recovered supernatant was sterilized by filtration through Millex GV filter of 0.22 µm in pore size (manufactured by Millipore). The anti-HB-EGF chimeric antibody KM3966 was purified from the thus obtained culture supernatant using a Protein A High-capacity resin (manufactured by Millipore) column in accordance with the instructions attached thereto. The purity and molecular weight were confirmed by SDS-PAGE using a gradient gel (manufactured by ATTO, E-T520L) in accordance with the instructions attached thereto.

Figure 6:
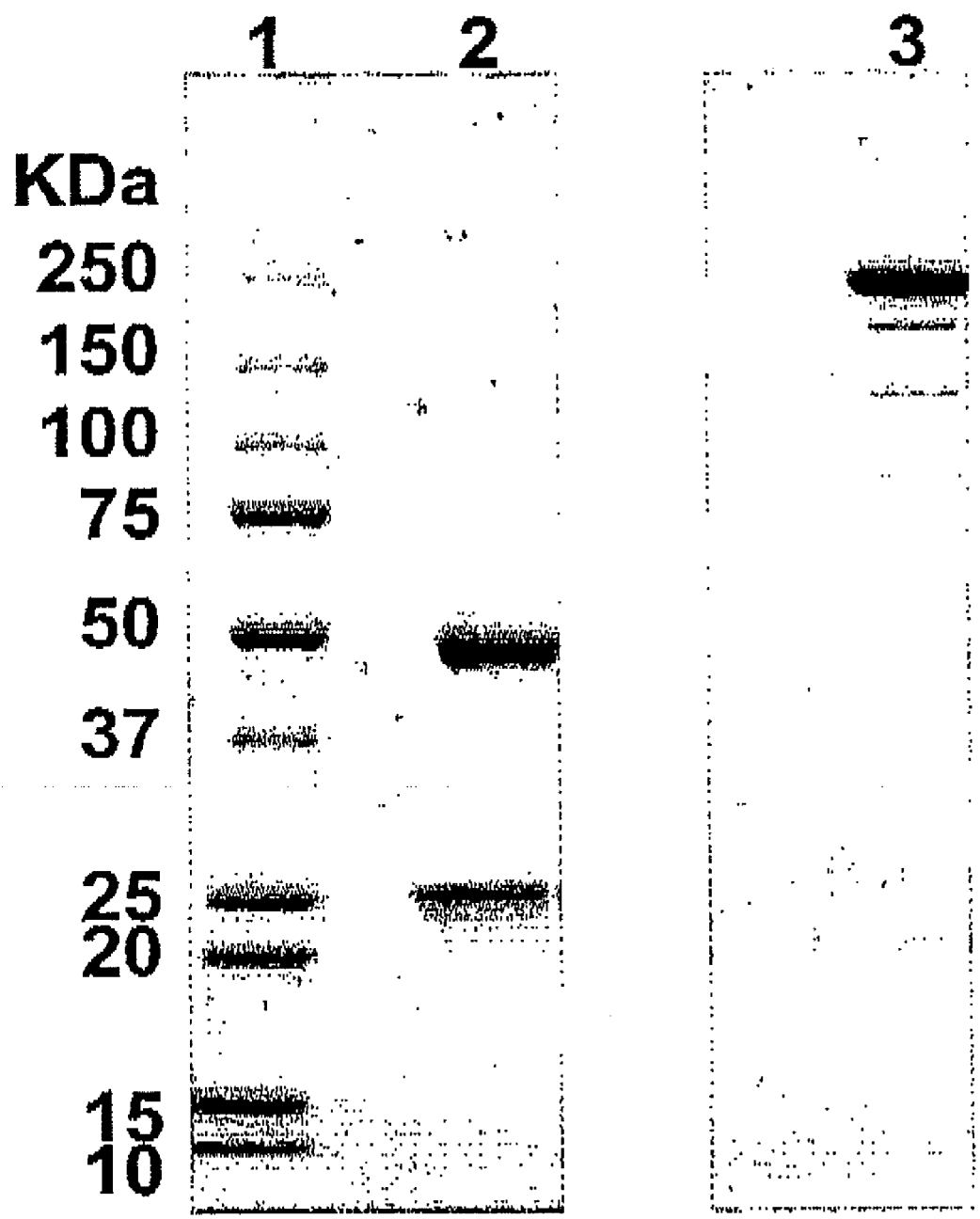
FIG. 6 shows the SDS-PAGE (using 5 to 20% gradient gel) electrophoresis pattern of purified anti-HB-EGF chimeric antibody KM3966. Lane 1 shows a molecular weight marker, lane 2 and lane 3 show the anti-HB-EGF chimeric antibody KM3966 under reducing conditions and under non-reducing conditions, respectively.

The results are shown in FIG. 6. Regarding molecular weight of the purified anti-HB-EGF chimeric antibody KM3966, a single band at around 150 to 200 kDa was found under non-reducing conditions, and two bands of about 50 kDa and about 25 kDa under reducing conditions. These molecular weights coincide with the report stating that an IgG class antibody has a molecular weight of about 150 kDa under non-reducing conditions but is degraded into H chain having a molecular weight of about 50 kDa and L chain having a molecular weight of about 25 kDa due to cutting of the intramolecular S—S bond [*Antibodies-A Laboratory Manual*, Cold Spring Harbor Laboratory, Chapter 14 (1988), *Monoclonal Antibodies-Principals and Practice*, Academic Press Limited (1996)]. Thus, it was confirmed that the anti-HB-EGF chimeric antibody KM3966 is expressed as an antibody molecule having correct structure.

Example 7

Activity Evaluation of Anti-HB-EGF Chimeric Antibody (1) Binding Activity for Human Solid Cancer Cell Line In order to evaluate binding activity of the anti-HB-EGF chimeric antibody KM3966 obtained in Example 6, it was examined by fluorescent antibody technique in the following manner.

Each cell line of human ovarian cancer cell lines MCAS (JCRB 0240), RMG-I (JCRB IF 050315) and ES-2 (CRL 1978), human beast cancer cell lines MDA-MB-231 (ATCC HTB-26), T47D (HTB-133), SK-BR-3 (ATCC HTB-30) and ZR-75-1 (ATCC CRL-1500) and a human gastric cancer cell line MKN-28 (HSRRB JCRB 0253) was peeled off with 0.02%-EDTA Solution (manufactured by Nacalai Tesque) and washed with PBS and then dispensed into a 96 well U-bottom plate (manufactured by FALCON) at 1 to $2\times10^5$ cells/50 µl/well. An anti-HB-EGF chimeric antibody KM3966 solution prepared to 20 µg/ml with 1% BSA-PBS was dispensed at 50 μl/well, followed by stirred using a plate mixer, and the plate was allowed to stand on ice for 30 minutes. After washing twice with PBS, a 100 times-diluted secondary antibody FITC-conjugated AffinityPure F(ab')$_2$ Fragment Rabbit Anti-Human IgG (H+L) (manufactured by Jackson Laboratories) was added thereto at 50 μl/well, followed by stirring using a plate mixer, and the plate was allowed to stand on ice for 30 minutes under shade. After washing twice with PBS, the fluorescence intensity was measured using a flow cytometer EPICS XL System II v. 3.0 (manufactured by BECKMAN COULTER). As the negative control antibody, anti-FGF-8 chimeric antibody KM3034 (US 2004-0253234) was used.

Figure 7:
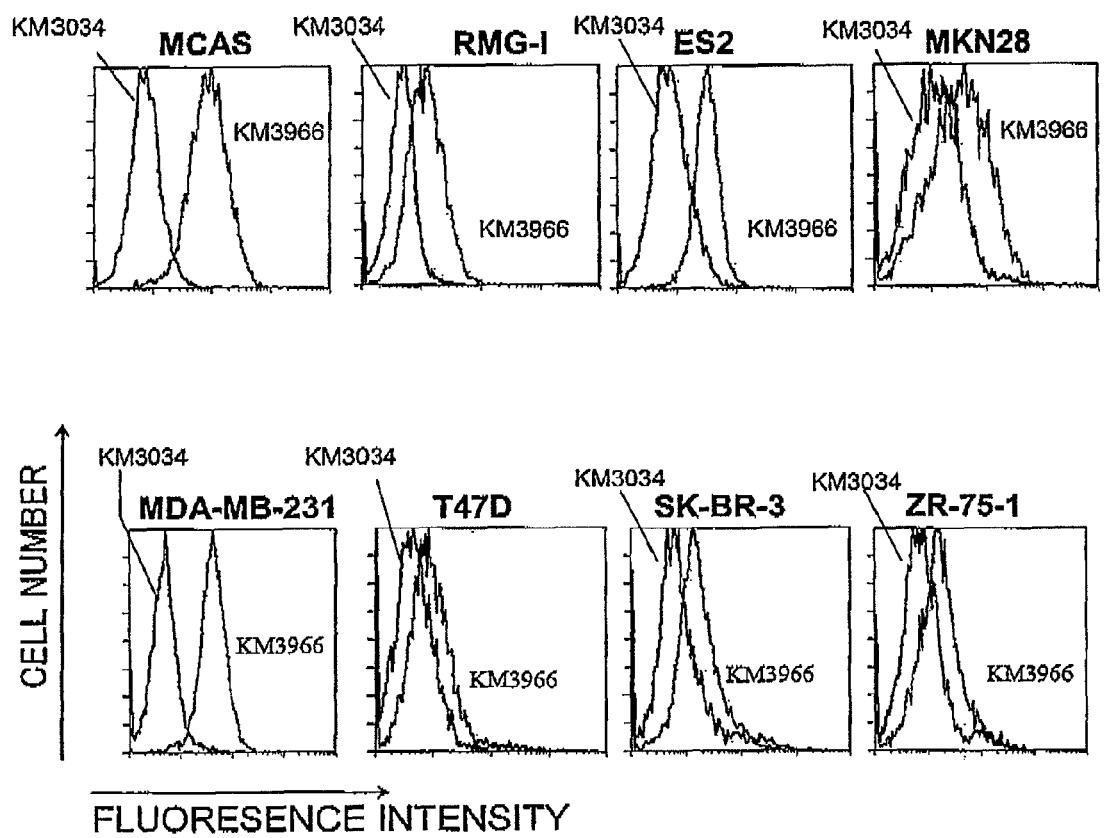
FIG. 7 shows the reactivity of anti-HB-EGF chimeric antibody KM3966 for a human solid carcinoma cell line by flow cytometry. In the drawing, the ordinate shows the number of cells, and the abscissa shows the fluorescence intensity.

The results are shown in FIG. 7. The anti-HB-EGF chimeric antibody KM3966 bound to the membrane type and cell membrane-bound HB-EGF of all of the human solid cancer cell lines.

(2) Measurement of Binding Activity of Anti-HB-EGF Chimeric Antibody KM3966 for Human HB-EGF In order to analyze binding activities of a mouse antibody KM3566 and the chimeric antibody KM3966 for human HB-EGF in reaction kinetics, the binding activity measurement was carried out using Biacore. All of the following operations were carried out using Biacore T-100 (manufactured by Biacore). Human HB-EGF (manufactured by R & D) prepared into 5 μg/ml using FIBS-EP Buffer (manufactured by Biacore) was immobilized onto a CM 5 sensor chip (manufactured by Biacore) to a level of 80 RU (resonance unit) by an amine coupling method. Thereafter, each antibody diluted 5-fold from 9 nmol/l was let flow on the chip at a rate of 10 μl/min, and by analyzing the sensor-gram at each concentration, the association rate constant and dissociation rate constant of each antibody for human HB-EGF were calculated.

As a result, it was found that dissociation reaction is hardly found after antibody binding with human HB-EGF within the antibody concentration range in the case of both antibodies, so that the dissociation rate constant could not be calculated. On the other hand, the association rate constant could be calculated, with the results shown in Table 1. It was confirmed based on the results that both antibodies almost the same binding activity for human HB-EGF.

TABLE 1

| Antibody | Ka (1/Ms) |
|---|---|
| KM3566 | $2.7 \times 10^5$ |
| KM3966 | $2.4 \times 10^5$ |

(3) Reactivity of Anti-HB-EGF Monoclonal Antibody for Cell Membrane-Bound HB-EGF Each cell line was peeled off with 0.02%-EDTA Solution (manufactured by Nacalai Tesque) and washed with PBS, followed by mixing with RPMI 1640 medium (manufactured by GIBCO-BRL) and centrifugation at 300 G for 5 minutes, and the supernatant was discarded. To the cells, 1 μg/ml of recombinant human HB-EGF (manufactured by R & D) diluted with 0.1% BSA-PBS was added and was allowed to react at 37° C. for 10 minutes. When the recombinant human HB-EGF was not added, 0.1% BSA-PBS alone was added and was allowed to react at 37° C. for 10 minutes in the same manner. After washing twice with 1% BSA-PBS, an anti-HB-EGF chimeric antibody KM3966 solution prepared into 10 μg/ml using 1% BSA-PBS was dispensed at 50 μl/well, followed by stirring using a plate mixer, and the plate was allowed to stand on ice for 30 minutes. After washing twice with PBS, a secondary antibody FITC-conjugated AffinityPure F(ab')$_2$ Fragment Rabbit Anti-Human IgG (H+L) (manufactured by Jackson Laboratories) diluted 100-fold was added thereto at 50 μl/well, followed by stirring using a plate mixer, and the plate was allowed to stand on ice for 30 minutes under shade. After washing twice with PBS, the fluorescence intensity was measured using a flow cytometer EPICS XL System II v. 3.0 (manufactured by BECKMAN COULTER). As the negative control antibody, an anti-FGF 8 chimeric antibody (US 2004-0253234) was used.

Figure 8:
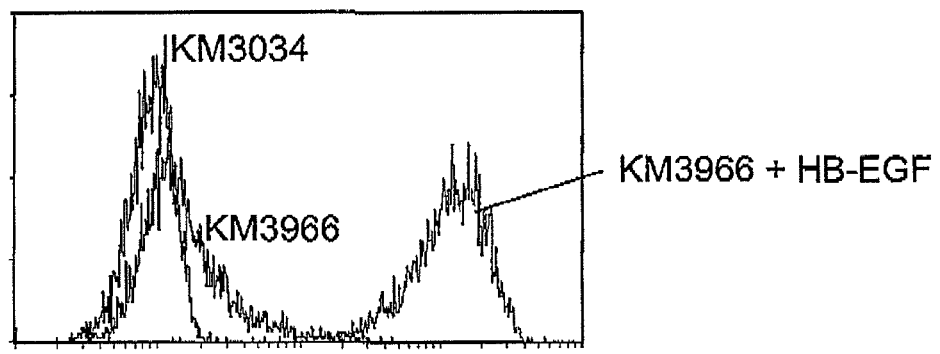
FIG. 8 shows the reactivity of anti-HB-EGF chimeric antibody KM3966 for a recombinant HB-EGF-treated human solid carcinoma cell line by flow cytometry. In the drawing, the ordinate shows the number of cells, and the abscissa shows the fluorescence intensity.
Figure 8:
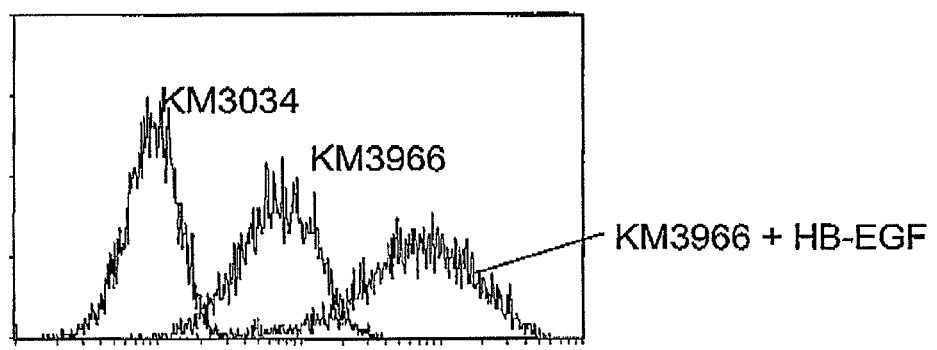
Figure 8:
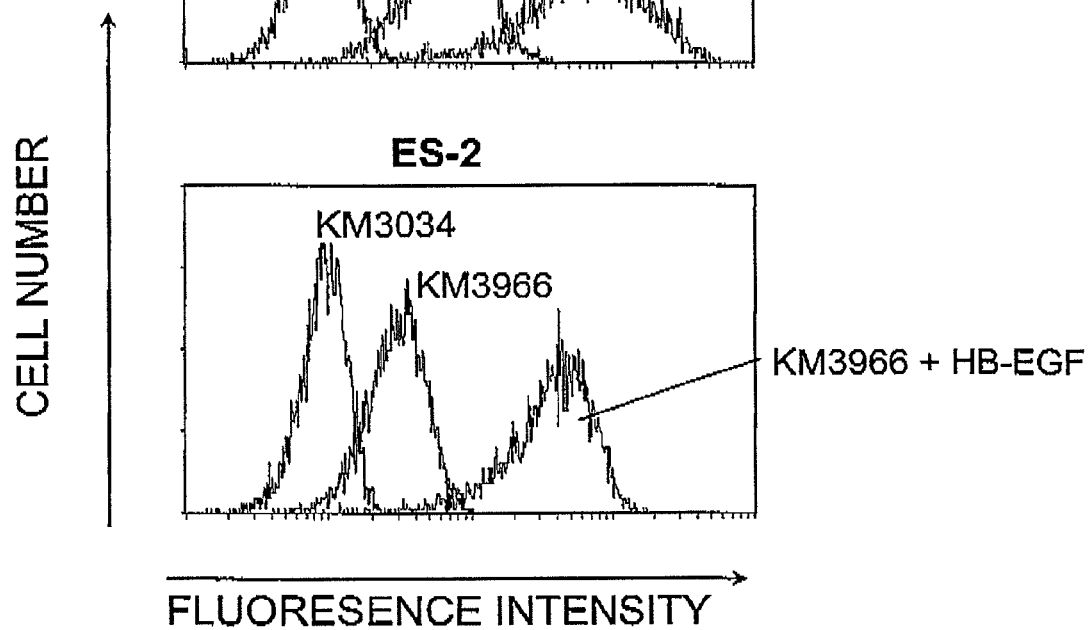

As a result, in all of the cell lines, reactivity of the anti-HB-EGF chimeric antibody KM3966 was increased in the cells treated with recombinant HB-EGF in comparison with the untreated cells (FIG. 8). Accordingly, it was found that the anti-HB-EGF chimeric antibody KM3966 of the invention binds to both of the membrane type and cell membrane-bound HB-EGF.

(4) Neutralization Activity for Human Solid Cancer Cell Lines

In order to evaluate HB-EGF neutralization activity of the anti-HB-EGF chimeric antibody KM3966 obtained in Example 6, HB-EGF-dependent cell growth inhibition activity was measured. As the HB-EGF-dependent cells, an HB-EGF-positive human ovarian cancer cell line RMG-I (JCRB IF 050315) and a human gastric cancer cell line MKN-28 (HSRRB JCRB) were used.

Each cell line was peeled off with 0.02%-EDTA Solution (manufactured by Nacalai Tesque) and washed with PBS, followed by mixing with RPMI 1640 medium (manufactured by GIBCO-BRL) (serum-free) and centrifugation at 300 G for 5 minutes, and the supernatant was discarded. After suspending the cells in the same medium, RMG-I and MKN-28 were seeded into a 96 well plate at $2.5 \times 10^3$ cells/50 μl/well and at $1 \times 10^4$ cells/50 μl/well, respectively. The recombinant human HB-EGF (manufactured by R & D) diluted with 0.1% BSA-PBS was added at 50 μl/well having a concentration of 3 ng/ml in the case of RMG-I, or at 50 μl/well portions having a concentration of 30 ng/ml in the case of MKN-28, and then anti-HB-EGF chimeric antibody KM3966 was diluted 10-fold by 4 serial steps starting from 30 μg/ml, and was added at 50 μl/well portions, followed by mixing. As the negative control antibody, a human IgG (manufactured by Mitsubishi Pharma Corp.) was used. After culturing at 37° C. for 72 hours, a viable cell measuring reagent WST-1 (manufactured by Nacalai Tesque) was added at 15 μl/well, and 2 hours thereafter, the absorbance at OD 450 nm was measured using a plate reader (Emax; manufactured by Molecular Devices).

Figure 9:
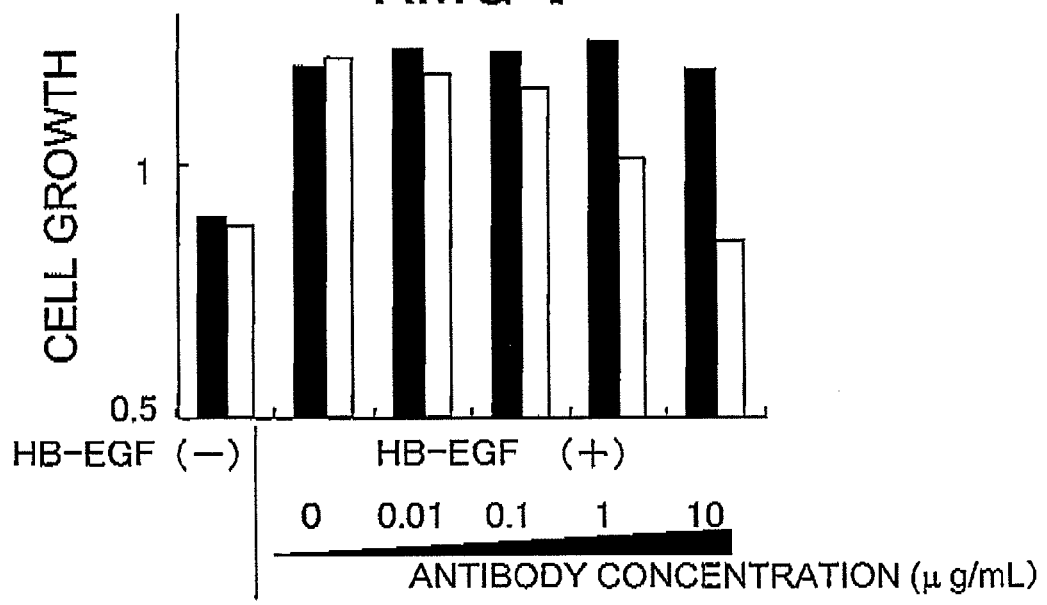
FIG. 9 shows the neutralization activity of anti-HB-EGF chimeric antibody KM3966 for human HB-EGF. In the drawing, the ordinate shows the absorbance value at OD 450 nm which represents the number of viable cells, and the abscissa antibody shows the concentration. ■ shows the negative control antibody human IgG, and □ shows KM3966. HB-EGF (−) shows no addition of HB-EGF, and HB-EGF (+) shows addition of HB-EGF.
Figure 9:
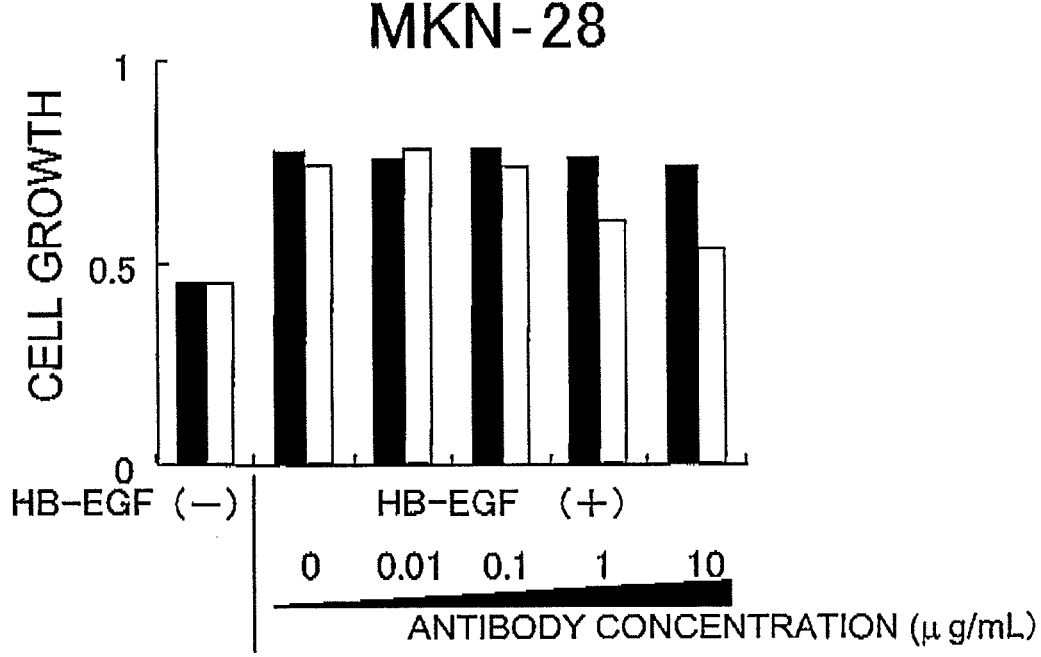

The results are shown in FIG. 9. Both of the RMG-I and MKN-28 showed cell growth caused by the addition of HB-EGF and showed HB-EGF-dependent cell growth. The anti-HB-EGF chimeric antibody KM3966 suppressed the HB-EGF-dependent cell growth in antibody concentration-dependent manner, thus showing neutralization activity.

(5) Antibody-Dependent Cellular Cytotoxicity (ADCC Activity)

ADCC activity of the anti-HB-EGF chimeric antibody KM3966 obtained in Example 6 was measured in accordance with the method shown below.

(5)-1 Preparation of Target Cell Solution

Each of the human ovarian cancer cell lines MCAS, RMG-I and ES-2, human breast cancer cell lines MDA-MB-231, T47D, SK-BR-3 an ZR-75-1 and a human gastric cancer cell stain MKN-28 was peeled off with 0.02%-EDTA Solution (manufactured by Nacalai Tesque), washed with RPMI 1640 medium (manufactured by Invitrogen) containing 1% FCS (manufactured by IRE) and not containing phenol red (to be referred to as ADCC medium hereinafter) and then adjusted to an optimum concentration using the same medium to be used as a target cell solution.

(5)-2 Preparation of Effector Cell Solution

Peripheral blood mononuclear cell (PBMC) was separated from peripheral blood of a healthy person by the method shown below. From a healthy person, 50 ml of peripheral blood was collected using a syringe containing a small amount of heparin sodium injection N "Shimizu" (manufactured by Shimizu Pharmaceutical). The thus collected peripheral blood was diluted by adding the same volume of physiological saline (the manufacture's name), followed by thoroughly stirring. Polymorphprep (manufactured by NYCOMED) was dispensed into 15 ml capacity tubes (manufactured by Greiner) at about 6.5 ml, and the same volume of the diluted peripheral blood was gently overlaid thereon and centrifuged at 800 G for 30 minutes at room temperature to separate the mononuclear cell layer. After washing twice using the ADCC medium, it was prepared to the optimum concentration with the same medium and used as the effector cell solution.

(5)-3 Measurement of ADCC Activity

An antibody dilution solution was dispensed in 50 μl portions into wells of a 96 well if-bottom plate, 50 μl of the target cell solution prepared in (4)-1 and 50 μl of the effector cell solution prepared in (4)-2 were added thereto (ratio of the effector cell (E) and the target cell (T) was set to 25), the total volume was adjusted to 150 μl, and the reaction was carried out at 37° C. for 4 hours. The value of target cell spontaneous release was obtained by adding 50 μl of the target cell solution and 100 μl of the medium, and the value of target cell and effector cell spontaneous release by adding 50 μl of the target cell solution, 50 μl of the effector cell solution and 50 μl of the medium. The value of target cell total release was obtained by adding 50 μl of the target cell solution and 80 μl of the medium, and by adding 20 μl of 9% Triton X-100 solution 45 minutes before completion of the reaction. After the reaction, the plate was centrifuged, and lactate dehydrogenase (LDH) activity in the supernatant was detected by measuring the absorbance using LDH-Cytotoxic Test (manufactured by Wako) in accordance with the instructions attached thereto. The ADCC activity was calculated by the following formula.

ADCC activity(%)([absorbance of sample]−[absorbance of target cell and effector cell spontaneous release])/([absorbance of target cell total release]−[absorbance of target cell spontaneous release])×100     (Formula)

Figure 10:
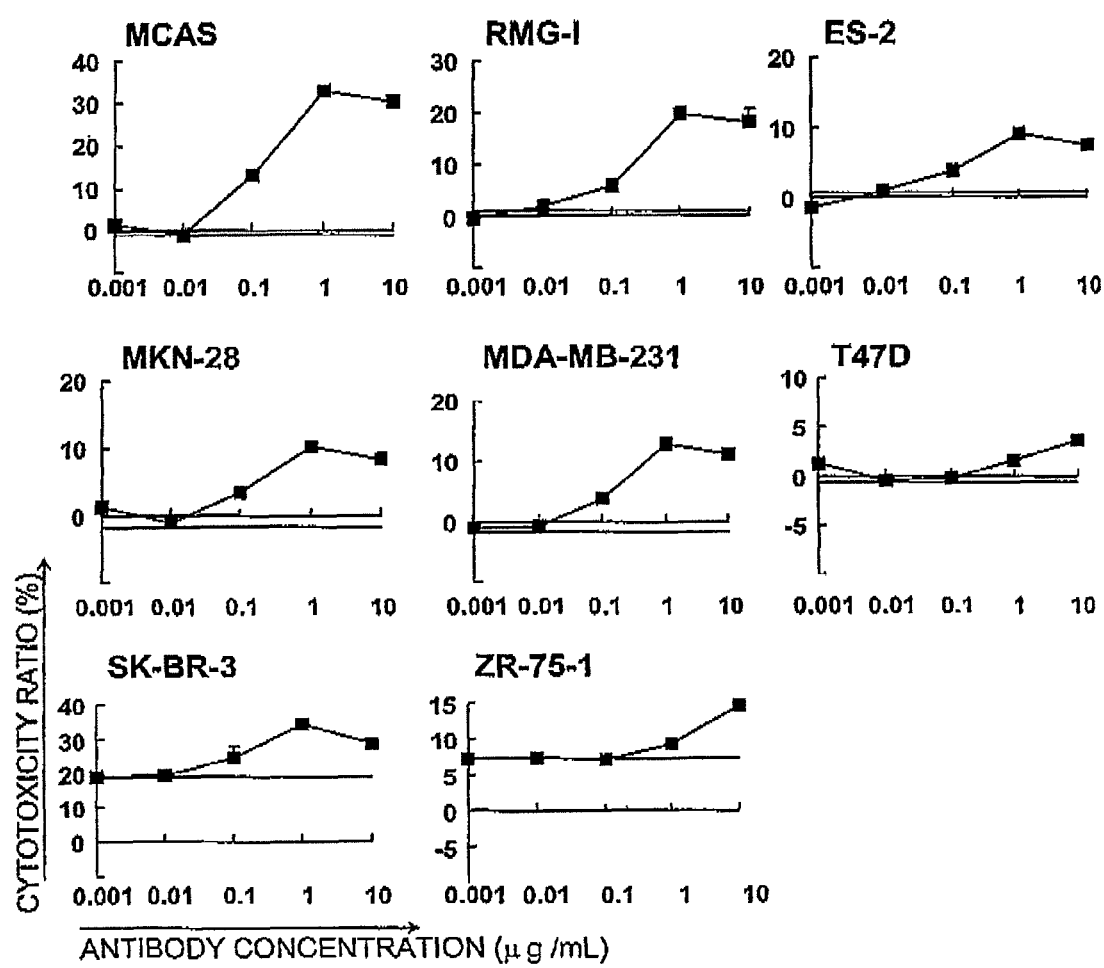
FIG. 10 shows the antibody-dependent cellular cytotoxicity (ADCC activity) of anti-HB-EGF chimeric antibody KM3966 for a human solid carcinoma cell line. In the drawing, the ordinate shows the cytotoxicity ratio (%), and the abscissa shows the antibody concentration of anti-HB-EGF chimeric antibody KM3966. The sidewise straight line shows the cytotoxicity at the time when the antibody was not added.

The results are shown in FIG. 10. The anti-HB-EGF chimeric antibody KM3966 showed antibody-dependent cytotoxicity for the HB-EGF-positive human solid cancer cell lines.

(6) Evaluation of Antitumor Activity Using Mouse Xenograft

In order to evaluate antitumor activity of the anti-HB-EGF chimeric antibody KM3966 obtained in Example 6, evaluation was carried out using mouse xenograft early cancer model and advanced cancer models of human ovarian cancer and human beast cancer.

(6)-1 Evaluation by Early Cancer Model

Each of human ovarian cancer cell lines MCAS and ES-2 was pealed off with 0.02%-EDTA Solution (manufactured by Nacalai Tesque) and was washed with PBS, and RPMI 1640 medium (manufactured by GIBCO-BRL) was added thereto, followed by centrifugation at 300 G for 5 minutes to discard the supernatant. The cells were washed by a centrifugation operation by adding the same medium and then prepared to the optimum density, and 100 μl of the thus prepared cell suspension was subcutaneously transplanted into the right frank of chest of each 8-week-old female SCID mouse (manufactured by CLEA Japan). Starting on the same day, 100 μl of an antibody solution diluted with PBS was administered from the caudal vein in the case of the antibody administration group, or PBS alone in the case of the control group (5 to 7 animals per group). The administration was carried out twice a week, 8 times in total, and the tumor diameter was measured using slide calipers starting at the time when a tumor was found. The tumor volume was calculated by the following formula.

Tumor volume(mm$^3$)=length×breadth$^2$×0.5     (Formula)

Figure 11:
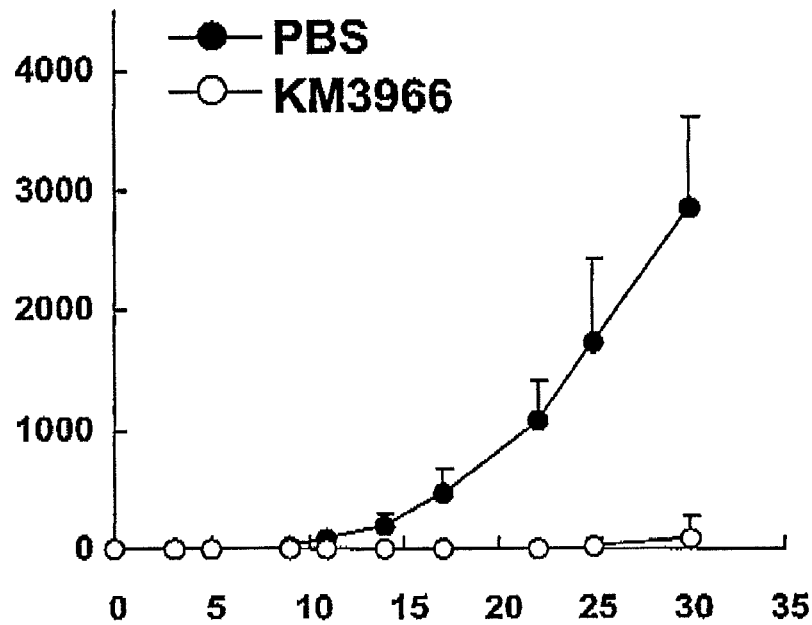
FIG. 11 shows the antitumor activity of anti-HB-EGF chimeric antibody KM3966 in an early cancer model. In the drawing, the ordinate shows the tumor volume, and the abscissa shows the number of days after cancer cell transplantation. ● shows PBS the administration group, and ○ shows the KM3966 10 mg/kg administration group. The bar shows the standard deviation.
Figure 11:
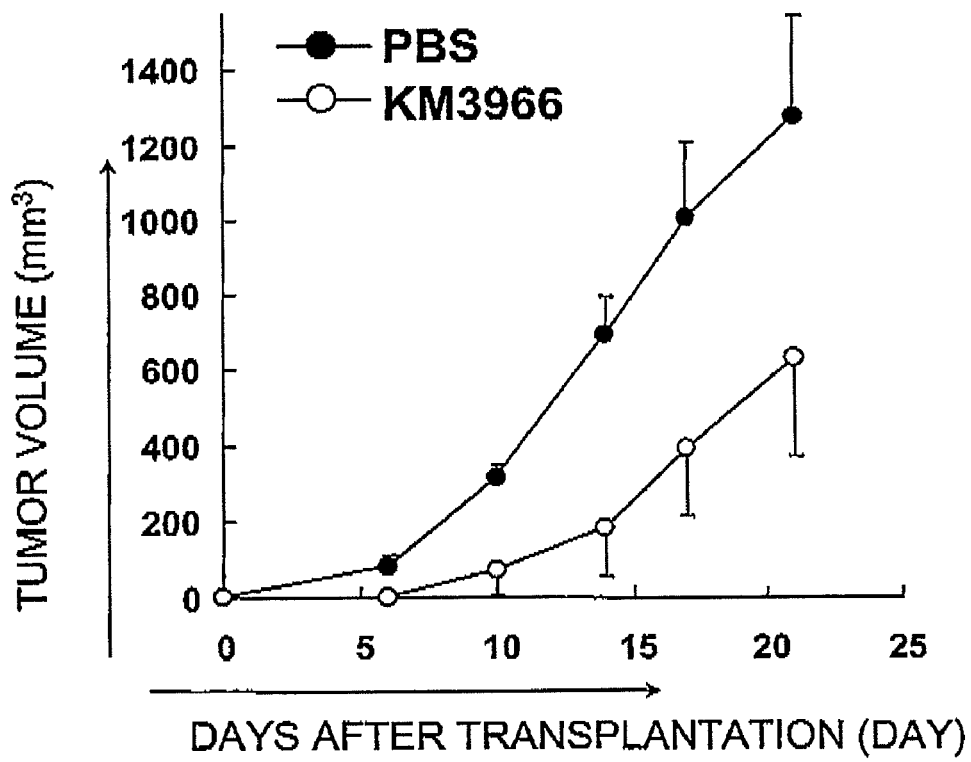

The results are shown in FIG. 11. The anti-HB-EGF chimeric antibody KM3966 significantly inhibited tumor growth of the ovarian cancer cell lines MCAS and ES-2. Accordingly, it was found that the anti-HB-EGF chimeric antibody KM3966 has antitumor effect in the early cancer model.

(6)-2 Evaluation by Advanced Cancer Model

Each of human ovarian cancer cell lines MCAS and ES-2 and a human breast cancer cell line MDA-MB-231 was pealed off with 0.02%-EDTA Solution (manufactured by Nacalai Tesque) and washed with PBS, and then RPMI 1640 medium (manufactured by GIBCO-BRL) was added thereto, followed by centrifugation at 300 G for 5 minutes to discard the supernatant. After the same medium was added, the cells were washed by centrifugation and then were prepared to the optimum density, and 100 μl of the thus prepared cell suspension was subcutaneously transplanted into the right armpit of each 6- to 8-week-old female SCID mouse (manufactured by CLEA Japan). By observing the development, the mice were selected when the tumor volume became about 100 mm$^3$, and their grouping was carried out in such a manner that the average tumor volume in respective groups became similar level. Starting on the same day, 100 μl of an antibody solution diluted with PBS was administered from the caudal vein in the case of the antibody administration group, or PBS alone in the case of the control group (6 or 7 animals per group). The administration was carried out twice a week, 8 times in total, and the tumor diameter was measured using slide calipers starting at the time of the antibody administration. The tumor volume was calculated by the following formula.

Tumor volume(mm$^3$)=length×breadth$^2$×0.5     (Formula)

Figure 12:
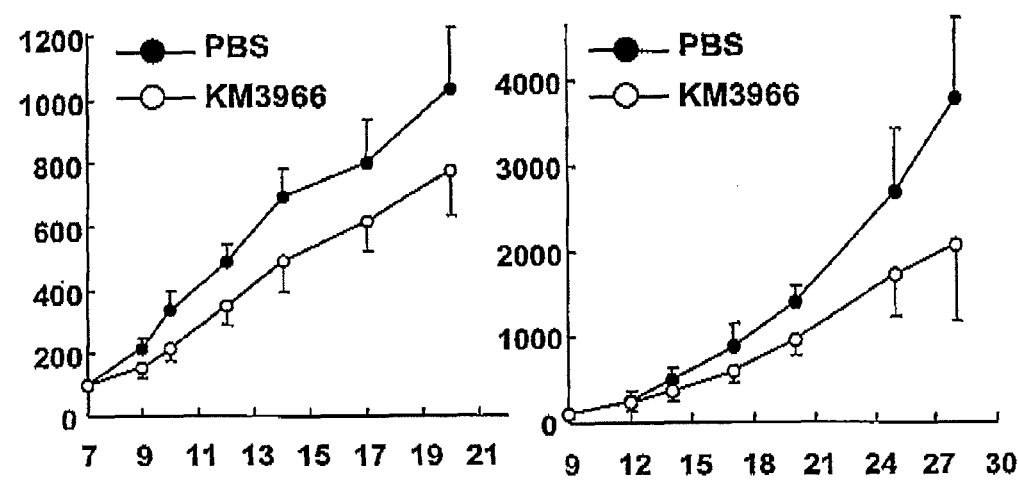
FIG. 12 shows the antitumor activity of anti-HB-EGF chimeric antibody KM3966 in an advanced cancer model. In the drawing, the ordinate shows the tumor volume, and the abscissa shows the number of days after cancer cell transplantation. ● shows the PBS administration group, and ○ shows the KM3966 10 mg/kg administration group. The bar shows the standard deviation.
Figure 12:
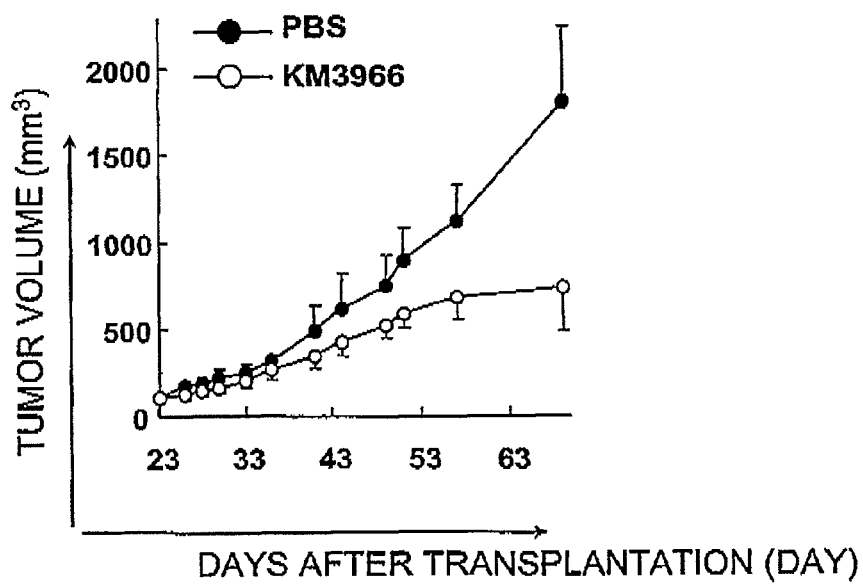

The results are shown in FIG. 12. As a result, the anti-HB-EGF chimeric antibody KM3966 significantly inhibited tumor growth of the ovarian cancer cell lines MCAS and ES-2 and breast cancer cell line MDA-MB 231. Accordingly, it was found that the anti-HB-EGF chimeric antibody KM3966 has the antitumor activity in the advanced cancer model.

Example 8

Evaluation of Reactivity and Antibody-Dependent Cellular Cytotoxicity (ADCC Activity) of Anti-HB-EGF Antibody for Human Blood Cancer Cell Lines (1) HB-EGF Expression Analysis in Human Blood Cancer Cell Lines In order to evaluate FIB-EGF expression in human blood cancer cell lines, it was examined by the fluorescent antibody technique. Each of human acute myelogenous leukemia cell lines ML-1 (DSMZ ACC 464), MOLM-13 (DSMZ ACC 554), MV-4-11 (ATCC CRL 9591), HL-60 (ATCC CRL-240), NB-4 (DSMZ ACC 207) and KG-1a (ATCC CCL-246.1) and human T cell leukemia cell lines Karpas 299 (DSMZ ACC 31) and Jurkat (RCB RCB 0806) was washed with PBS, was prepared to the optimum density and then was dispensed into a 96 well U-bottom plate (manufactured by FALCON) at 50 µl/well (about $2\times10^5$ cells). An anti-HB-EGF mouse antibody KM3566 solution prepared into 20 µg/ml with 1% BSA-PBS was dispensed at 50 µl/well, followed by stirring using a plate mixer, and the plate was allowed to stand on ice for 30 minutes. After washing twice with PBS, a 50-fold diluted secondary antibody Anti-mouse Igs/FITC Goat $F(ab')_2$ (manufactured by DAKO) was added thereto at 50 µl/well, followed by stirring using a plate mixer, and the plate was allowed to stand on ice for 30 minutes under shade. After washing twice with PBS, the fluorescence intensity was measured using a flow cytometer EPICS XL System II v. 3.0 (manufactured by BECKMAN COULTER). As the negative control antibody, mouse IgG1 (manufactured by DAKO) was used.

Figure 13:
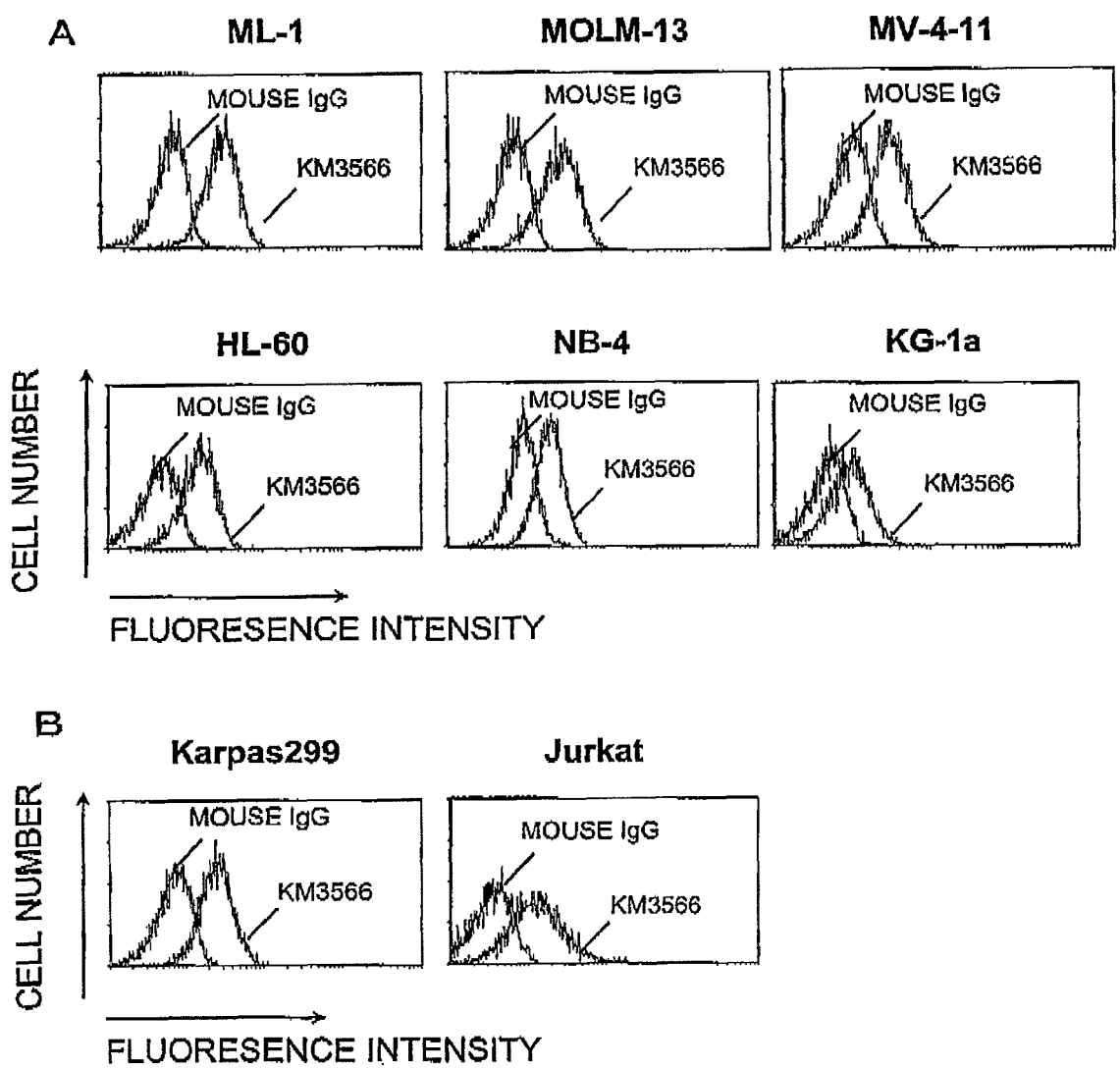
FIG. 13 shows the reactivity of anti-HB-EGF mouse antibody KM3566 for a human blood cancer cell line by flow cytometry. In the drawing, the ordinate shows the number of cells, and the abscissa shows the fluorescence intensity. "A" shows the acute myelogenous leukemia cell line, and "B" shows the T cell leukemia cell line.

The results are shown in FIG. 13. The KM3566 specifically bound to the T cell leukemia and acute myelogenous leukemia cell lines. Accordingly, it was confirmed that HB-EGF is expressing in human blood cancer cell lines.

(2) Antibody-Dependent Cellular Cytotoxicity (ADCC Activity) of Anti-HB-EGF Chimeric Antibody for Human Blood Cancer Cell Lines ADCC activity of the anti-HB-EGF chimeric antibody KM3966 for the acute myelogenous leukemia cell lines in which expression of HB-EGF was confirmed was measured by the method shown below.

(2)-1 Preparation of Target Cell Solution

Each of the human acute myelogenous leukemia cell lines ML-1, MOLM-13, MV-4-11, HL-60, NB-4 and KG-1a was washed with PBS, washed with the ADCC medium and then prepared to the optimum density with the same medium and used as the target cell solution.

(2)-2 Preparation of Effector Cell Solution

Peripheral blood mononuclear cell (PBMC) was separated from peripheral blood of a healthy person by the method shown below. From a healthy person, 50 ml of peripheral blood was collected using a syringe containing a small amount of heparin sodium injection N "Shimizu" (manufactured by Shimizu Pharmaceutical). The thus collected peripheral blood was diluted by adding the same volume of physiological saline (manufactured by Otsuka Pharmaceutical), followed by thoroughly stirring. Polymorphprep (manufactured by NYCOMED) was dispensed into 15 ml capacity tubes (manufactured by Greiner) at about 6.5 ml, and the same volume of the diluted peripheral blood was gently overlaid thereon, followed by centrifugation at 800 G for 30 minutes at room temperature to separate the mononuclear cell layer. After washing twice using the ADCC medium, it was adjusted to the optimum concentration with the same medium and used as the effector cell solution.

(2)-3 Measurement of ADCC Activity

An antibody dilution solution was dispensed into wells of a 96 well U-bottom plate (manufactured by FALCON) at 50 µl, 50 µl of the target cell solution prepared in (2)-1 and 50 µl of the effector cell solution prepared in (2)-2 were added thereto (ratio of the effector cell (E) and the target cell (T) was set to 25), the total volume was adjusted to 150 µl, and the reaction was carried out at 37° C. for 4 hours. The value of target cell spontaneous release was obtained by adding 50 µl of the target cell solution and 100 µl of the medium, and the value of target cell and effector cell spontaneous release by adding 50 µl of the target cell solution, 50 µl of the effector cell solution and 50 µl of the medium. The value of target cell total release was obtained by adding 50 µl of the target cell solution and 80 µl of the medium, and by adding 20 µl of 9% Triton X-100 solution 45 minutes before completion of the reaction. After the reaction, the plate was centrifuged, and lactate dehydrogenase (LDH) activity in the supernatant was detected by measuring the absorbance using LDH-Cytotoxic Test (manufactured by Wako) in accordance with the instructions attached thereto. The ADCC activity was calculated by the following formula.

ADCC Activity(%)([absorbance of sample]−[absorbance of target cell and effector cell spontaneous release])/([absorbance of target cell total release]−[absorbance of target cell spontaneous release])×100    (Formula)

Figure 14:
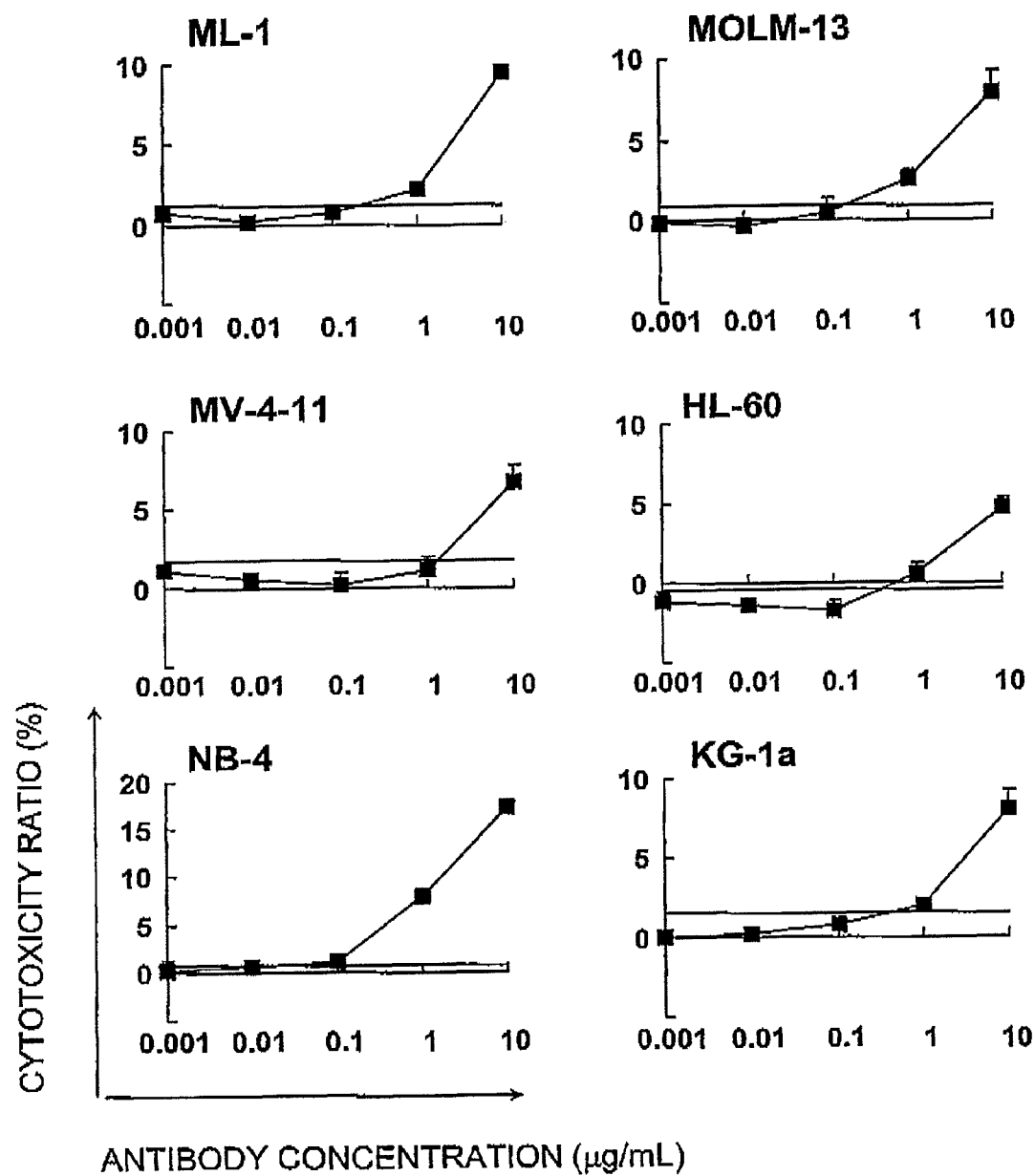
FIG. 14 shows the antibody-dependent cellular cytotoxicity (ADCC activity) of anti-HB-EGF chimeric antibody KM3966 for a human blood cancer cell line. In the drawing, the ordinate shows the cytotoxicity ratio (%), and the abscissa shows the antibody concentration of anti-HB-EGF chimeric antibody KM3966. The sidewise straight line shows the cytotoxicity at the time when the antibody was not added.

The results are shown in FIG. 14. The anti-HB-EGF chimeric antibody KM3966 showed antibody-dependent cytotoxicity for the HB-EGF-positive human blood cancer cell lines. Accordingly, it was suggested that there is a possibility that the anti-HB-EGF monoclonal antibody and recombinant antibody of the invention are effective not only for solid cancers such as ovarian cancer expressing HB-EGF but also for blood cancers such as acute myelogenous leukemia and T cell leukemia.

Example 9

Preparation of Anti-HB-EGF Humanized Antibody (1) Designing of Amino Acid Sequences of VH and VL of Anti-HB-EGF Humanized Antibody Firstly, the amino acid sequence of VH of anti-HB-EGF humanized antibody was designed as follows.

In order to graft amino acid sequences of CDRs 1 to 3 of antibody VH represented by SEQ ID NOs:12 to 14, respectively, an FR amino acid sequence of VH of a human antibody was selected. Kabat et al. have classified the VH of various known human antibodies into three subgroups (HSG I to III) based on the homology of the amino acid sequences and further reported consensus sequences among respective subgroups (*SEQUENCES of Proteins of Immunological Interest*, US Dept. Health and Human Services, 1991). Since these consensus sequences have a possibility that the immunogenicity is reduced in human, it was decided to design a VH amino acid sequence of an anti-HB-EGF humanized antibody based on these consensus sequences. In order to prepare an anti-HB-EGF humanized antibody having more higher binding activity in designing it, it was decided to select an FR amino acid sequence having the highest homology with the FR amino acid sequence of VH of anti-HB-EGF mouse antibody KM3566, among FR amino acid sequences of consensus sequences of the three subgroups of VH of human antibodies.

As a result of homology retrieval, homologies of HSG I, HSG II and HSG III were 73.6%, 50.6% and 56.3%, respectively. Thus, the amino acid sequence of FR of VH region of KM3566 had the highest homology with the subgroup I.

Based on the above results, CDRs amino acid sequences of VH of the anti-HB-EGF mouse antibody KM3566 were grafted to an appropriate position of the FR amino acid sequence of the consensus sequence of subgroup I of VH of the human antibody. However, although Lys at position 74 in the VH amino acid sequence of KM3566 described in SEQ ID NO:9 is not the amino acid residue having the highest usage frequency cited by Kabat et al., in a corresponding region of the human antibody FR amino acid sequence, but is an amino acid residue which is used at a relatively high frequency, so that it was decided to use the above-mentioned amino acid residue which is found in the amino acid sequence of KM3566. Thus, the amino acid sequence HV0 of VH of anti-HB-EGF humanized antibody, represented by SEQ ID NO:22, was designed.

Next, the amino acid sequence of VL of the anti-HB-EGF humanized antibody was designed as follows.

In order to graft amino acid sequences of CDRs 1 to 3 of antibody VL represented by SEQ ID NOs:15 to 17, respectively, an FR amino acid sequence of VL of a human antibody was selected. Kabat et al. have classified the VL of various known human antibodies into four subgroups (HSG I to IV) based on the homology of the amino acid sequences and then reported consensus sequences among respective subgroups [*Sequences of Proteins of Immunological Interest*, US Dept. Health and Human Services, (1991)]. Accordingly, similar to the case of VH, an FR amino acid sequence having the highest homology with the FR amino acid sequence of VL of anti-HB-EGF mouse antibody KM3566 was selected from FR amino acid sequences of consensus sequences of the four subgroups of VL of human antibodies.

As a result of homology search, homologies of HSG I, HSG II, HSG III and HSG IV were 75.0%, 75.9%, 71.3% and 81.3%, respectively. Thus, the amino acid sequence of FR of VL region of KM3566 had the highest homology with the subgroup IV.

Based on the above results, CDRs amino acid sequence of VL of the anti-HB-EGF mouse antibody KM3566 were grafted to an appropriate position of the amino acid sequence of FR of the consensus sequence of subgroup IV of VL of the human antibody. However, although Leu at position 110 in the VL amino acid sequence of KM3566 described in SEQ ID NO:11 is not the amino acid residue having the highest usage frequency cited by Kabat et al., in a corresponding region of the human antibody FR amino acid sequence, but is an amino acid residue which is used at a relatively high frequency, so that it was decided to use the above-mentioned amino acid residue which is found in the amino acid sequence of KM3566. Thus, the amino acid sequence LV0 of VL of anti-HB-EGF humanized antibody, represented by SEQ ID NO:23, was designed.

The thus designed amino acid sequence HV0 of VH and amino acid sequence LV0 of VL of the anti-HB-EGF humanized antibody are sequences in which only the CDRs amino acid sequences of the anti-HB-EGF mouse antibody KM 13566 were grafted to the FR amino acid sequence of the selected human antibody. However in general, when a humanized antibody is prepared, the binding activity is decreased in many cases by grafting of a mouse antibody CDR amino acid sequence alone. Thus, in order to avoid this reduction of binding activity, among FR amino acid residues different between a human antibody and a mouse antibody, modification of amino acid residues considered to have influences on the binding activity is carried out together with grafted together with grafting of a CDR amino acid sequence. Accordingly, in this Example, the FR amino acid residues considered to have influences on the binding activity was also identified as follows.

Firstly, a three-dimensional structure of an antibody V region (HV0LV0) consisting of the amino acid sequence HV0 of VH and amino acid sequence LV0 of VL of anti-HB-EGF humanized antibody designed in the above, was constructed by computer modeling technique. This construction was carried out using a software AbM (manufactured by Oxford Molecular) for the preparation of three-dimensional structure coordinates and a software Pro-Explore (manufactured by Oxford Molecular) or ViewerLite (manufactured by Accelrys) for the display of three-dimensional structure, in accordance with respective instructions attached thereto. Also, a computer model of the three-dimensional structure of the V region of anti-HB-EGF mouse monoclonal antibody KM3566 was also constructed in the same manner. In addition, a three-dimensional structure model was constructed in the same manner by preparing an amino acid sequence in which amino acid residues different from anti-HB-EGF mouse antibody KM3566 in the FR amino acid sequences of VH and VL of HV0LV0 were selected and modified into the amino acid residues of anti-HB-EGF mouse antibody KM3566. By comparing three-dimensional structures of V regions of these prepared anti-HB-EGF mouse antibody KM3566, HV0LV0 and modified product, the amino acid residues considered to have influences on the binding activity of antibody were identified.

As a result, as amino acid residues among the FR amino acid residues of HV0LV0, considered to have influences on the antibody activity by changing three-dimensional structure of the antigen-binding region, Ala at position 9, Val at position 20, Thr at position 30, Arg at position 38, Pro at position 41, Met at position 48, Arg at position 67, Val at position 68, Ile at position 70, Tyr at position 95 and Val at position 118, were selected regarding HV0, and Leu at position 15, Ala at position 19, Ile at position 21, Pro at position 49 and Leu at position 84 regarding LV0, respectively. By modifying at least one or more of these selected amino acid residues to the amino acid residues presenting in the same region of mouse antibody KM3566, the VH and VL of humanized antibody having various modifications were designed. Specifically, regarding the antibody VH, at least one modification was introduced among the amino acid modifications in which, in the amino acid sequence represented by SEQ ID NO:22, Ala at position 9 was substituted with Thr, Val at position 20 was substituted with Leu, Thr at position 30 was substituted with Arg, Arg at position 38 was substituted with Lys, Pro at position 41 was substituted with Thr, Met at position 48 was substituted with Ile, Arg at position 67 was substituted with Lys, Val at position 68 was substituted with Ala, Ile at position 70 was substituted with Leu, Tyr at position 95 was substituted with Phe and Val at position 118 was substituted with Leu. Also, regarding the VL, at least one modification was introduced among the amino acid modifications in which, in the amino acid sequence represented by SEQ ID NO:23, Leu at position 15 was substituted with Val, Ala at position 19 was substituted with Val, Ile at position 21 was substituted with Met, Pro at position 49 was substituted with Ser and Leu at position 84 was substituted with Val.

(2) Construction of cDNA Encoding VH of Anti-HB-EGF Humanized Antibody

A cDNA encoding the anti-HB-EGF humanized antibody VH amino acid sequence HV0 designed in this Example (1) was constructed using PCR in the following manner.

Firstly, the designed amino acid sequence was made into complete antibody amino acid sequence by ligating with the secretion signal sequence of H chain of anti-HB-EGF mouse antibody KM3566 described in positions 1 to 19 of SEQ ID NO:9. Next, the amino acid sequence was converted into genetic codons. When two or more genetic codons were present for one amino acid residue, corresponding genetic codon was determined by taking the codon usage found in nucleotide sequences of antibody genes into consideration

[SEQUENCES of Proteins of Immunological Interest, US Dept. Health and Human Services, 1991)]. The nucleotide sequence of a cDNA encoding the complete antibody V region amino acid sequence was designed by ligating the thus determined genetic codons, and binding nucleotide sequences of primers for PCR amplification (including restriction enzyme recognition sequences for cloning into a humanized antibody expression vector) were added to the 5'-terminal and 3'-terminal. The thus designed nucleotide sequence was divided into a total of 4 nucleotide sequences, each having about 100 nucleotides, from the 5'-'terminal side (adjoining nucleotide sequences are designed such that the termini have an overlapping sequence of about 20 nucleotides), and synthetic DNA fragments (SEQ ID NOs:24 to 27) were synthesized by arranging them in alternating order of sense chain and antisense chain.

Each of the synthetic DNA fragments (SEQ ID NOs:24 to 27) was added to 50 μl of a reaction solution to a final concentration of 0.1 μmol/l, and PCR was carried out using 0.5 μmol/l of T3 primer (manufactured by Takara Shuzo), 0.5 μmol/l of T7 primer (manufactured by Takara Shuzo) and 1 unit of KOD polymerase (manufactured by TOYOBO), in accordance with the instructions attached to the KOD polymerase. As the reaction conditions in this case, the PCR was carried out in accordance with the conditions described in the instructions (30 cycles consisting of reactions at 94° C. for 30 seconds, at 50° C. for 30 seconds and at 74° C. for 60 seconds). The reaction solution was subjected to ethanol precipitation, and the precipitate was dissolved in sterile water, subjected to appropriate restriction enzyme treatment and then ligated with a plasmid pBluescript II SK(−). *E. coli* DH5α was transformed using the thus obtained recombinant plasmid DNA solution, each plasmid DNA was prepared from each of the transformants, and then its nucleotide sequence was analyzed using Big Dye Terminator Cycle Sequencing Kit (manufactured by Applied Biosystems). As a result, a plasmid having the nucleotide sequence of interest was obtained.

Next, the FR amino acid residues designed in this Example (1) was modified by preparing a synthetic DNA having mutation and carrying out the above-mentioned PCR, or by carrying out PCR using a plasmid DNA containing a cDNA encoding the HV0 prepared in the above, as the template, and synthetic DNA fragments as primers, and isolating an amplified gene fragment. Gene codons of the amino acid residues after modification were prepared in such a manner that they became the gene codons found in the anti-HB-EGF mouse antibody KM3566. In addition, unless otherwise indicated below, the reaction was carried out by 35 cycles of the PCR, each cycle consisting of reactions at 94° C. for 30 seconds, at 55° C. for 30 seconds and at 72° C. for 60 seconds. The PCR was carried out using KOD-plus polymerase (manufactured by TOYOBO). Also, the synthetic DNA used herein is a product of FASMAC Co., Ltd.

(3) Construction of cDNA Encoding VL of Anti-HB-EGF Humanized Antibody

A cDNA encoding the anti-HB-EGF humanized antibody VL amino acid sequence designed in this Example (1) was constructed using PCR described below.

Firstly, the designed amino acid sequence was made into complete antibody amino acid sequence by ligating with the secretion signal sequence of L chain of anti-HB-EGF mouse antibody KM3566, represented by positions 1 to 20 of SEQ ID NO:11. Next, the amino acid sequence was converted into genetic codons. When two or more genetic codons were present for one amino acid residue, corresponding genetic codon was determined by taking the codon usage found in nucleotide sequences of antibody genes into consideration [SEQUENCES of Proteins of Immunological Interest, US Dept. Health and Human Services, 1991)]. The nucleotide sequence of a cDNA encoding the complete antibody V region amino acid sequence was designed by ligating the thus determined genetic codons, and binding nucleotide sequences of primers for use in the PCR amplification (including restriction enzyme recognition sequences for cloning into a humanized antibody expression vector) were added to the 5'-terminal and 3'-terminal. The thus designed nucleotide sequence was divided into a total of 4 nucleotide sequences, each having about 100 nucleotides, from the 5'-terminal side (adjoining nucleotide sequences are designed such that the termini have an overlapping sequence of about 20 nucleotides), and synthetic DNA fragments (SEQ ID NOs:28 to 31) were synthesized by arranging them in alternating order of sense chain and antisense chain.

Each of the synthetic DNA fragments (SEQ ID NOs:28 to 31) was added to 50 μl of a reaction solution to a final concentration of 0.1 μmol/l, and PCR was carried out in the same manner as in the above-mentioned (2) using 0.5 μmol/l of T3 primer (manufactured by Takara Shuzo), 0.5 μmol/l of T7 primer (manufactured by Takara Shuzo) and 1 unit of KOD polymerase (manufactured by TOYOBO), in accordance with the instructions attached to the KOD polymerase. The reaction solution was subjected to ethanol precipitation, and the precipitate was dissolved in sterile water, subjected to an appropriate restriction enzyme treatment and then connected to a plasmid pBluescript U SK(−). *E. coli* DH5α was transformed using the thus obtained recombinant plasmid DNA solution, each plasmid DNA was prepared from each of the transformants, and then its nucleotide sequence was analyzed using Big Dye Terminator Cycle Sequencing Kit (manufactured by Applied Biosystems). As a result, a plasmid pBS/LV0 having the nucleotide sequence of interest was obtained.

Next, the FR amino acid residues designed in this Example (1) was modified by preparing a synthetic DNA having mutation and carrying out the above-mentioned PCR, or by carrying out PCR using a plasmid DNA containing a cDNA encoding the LV0 prepared in the above, as the template, and synthetic DNA fragments as primers, and isolating an amplified gene fragment. Gene codons of the amino acid residues after modification were prepared in such a manner that they became the gene codons found in the anti-HB-EGF mouse antibody KM3566.

In the following, unless otherwise noted, the PCR was carried out by 35 cycles, each cycle consisting of reactions at 94° C. for 30 seconds, at 55° C. for 30 seconds and at 72° C. for 60 seconds, using KOD-plus polymerase (manufactured by TOYOBO). Also, the synthetic DNA used herein is a product of FASMAC Co., Ltd.

(4) Construction of Anti-HB-EGF Humanized Antibody Expression Vector

Various anti-HB-EGF humanized antibody expression vectors were constructed by inserting a cDNA encoding the HV0 or LV0 obtained in this Example (2) or (3), or a cDNA encoding a modified product thereof, into an appropriate position of the vector pKANTEX93 for humanized antibody expression described in WO 97/10354.

(5) Stable Expression of Anti-HB-EGF Humanized Antibody and Preparation of Purified Antibody Using an Animal Cell Stable expression of anti-HB-EGF humanized antibody and purification of the antibody from a culture supernatant, using an animal cell, were carried out in the same manner as the methods described in Example 6(2) and (3).

Example 10

Analysis on Binding Epitopes of Anti-HB-EGF Antibodies

The following analysis was carried out on the binding epitopes of anti-HB-EGF antibodies KM3566, KM3579 and KM3966 for human HB-EGF.

(1) Construction of Mutation Type Human HB-EGF Complete Length Gene-Transferred Cell All of the anti-HB-EGF antibodies KM3566, KM3579, and KM3966 react with human HB-EGF, and do not show cross reaction with mouse HB-EGF. Thus, gene-transferred cells which express 10 kinds of mutation type human HB-EGF complete length proteins (to be referred to as mutant HB-EGF hereinafter) in which each of 10 amino acids in the amino acid sequence of EGF-like domain of human HB-EGF, which are different from mouse HB-EGF, was substituted with a mouse-derived amino acid were constructed, and binding epitopes were analyzed by measuring binding activity of anti-HB-EGF antibodies for these. The prepared 10 kinds of mutant HB-EGF are shown below.

(1) A mutant HB-EGF in which phenylalanine at position 115 from the N-terminal was substituted with tyrosine (hereinafter referred to as "F115Y")

(2) A mutant HB-EGF in which lysine at position 122 from the N-terminal was substituted with arginine (hereinafter referred to as "K122R")

(3) A mutant HB-EGF in which valine at position 124 from the N-terminal was substituted with leucine (hereinafter referred to as "V124L")

(4) A mutant FIB-EGF in which lysine at position 125 from the N-terminal was substituted with glutamine (hereinafter referred to as "K125Q")

(5) A mutant FIB-EGF in which leucine at position 127 from the N-terminal was substituted with phenylalanine (hereinafter referred to as "L127F")

(6) A mutant HB-EGF in which alanine at position 129 from the N-terminal was substituted with threonine (hereinafter referred to as "A129T")

(7) A mutant HB-EGF in which isoleucine at position 133 from the N-terminal was substituted with lysine (hereinafter referred to as "I133K")

(8) A mutant HB-EGF in which histidine at position 135 from the N-terminal was substituted with leucine (hereinafter referred to as "H135L")

(9) A mutant HB-EGF in which glutamic acid at position 141 from the N-terminal was substituted with histidine (hereinafter referred to as "E141H")

(10) A mutant HB-EGF in which serine at position 147 from the N-terminal was substituted with threonine (hereinafter referred to as "S147T").

In addition, the following human/mouse chimeric HB-EGF complete length gene-transferred cell was constructed as the positive control.

(11) A human/mouse chimeric HB-EGF in which a sequence of positions 1 to 49 from N-terminal consists of a mouse HB-EGF-derived sequence and a sequence of positions 50 to 208 from N-terminal consists of a human FIB-EGF-derived sequence was prepared. Since all of the EGF-like domains are human HB-EGF-derived sequences, this HB-EGF was used as the positive control.

The plasmids for transient expression of the above-mentioned mutant HB-EGF and human/mouse chimeric HB-EGF were prepared using the method of Mekada et al. (*J. Bio. Chem.*, 272, 27084-27090 (1997)). Mouse LMTK cell (ATCC CCL-1.3) was cultured using Dulbecco's modified Eagle's medium supplemented with 100 unit/ml of penicillin G, 100 µg/ml of streptomycin and 10% bovine serum albumin. Each of the above-mentioned expression plasmids was transferred into the mouse LMTK cell by the calcium phosphate method, and then the cells were cultured for 48 hours and used in the following test.

Cell prepared by transferring the vector alone into the mouse LMTK cell (hereinafter referred to as "mock") was used as the negative control.

(2) Binding Activity Analysis of Anti-HB-EGF Antibody Using Mutant HB-EGF Gene-Transferred Cell Firstly, biotin-labeled anti-HB-EGF antibody (KM3566, KM3579 or KM3966) diluted to 2 µg/ml with a binding buffer (prepared by adding nonessential amino acids, 20 mM HEPES-NaOH (pH 7.2) and 10% fetal bovine serum to Ham's F12) was allowed to react at 4° C. for 2 hours with $1 \times 10^5$ cells of the mutant HB-EGF gene-transferred cell, human/mouse chimeric HB-EGF gene-transferred cell or mock. After the reaction, the cells were washed twice with an ice-cooled washing buffer (prepared by adding 0.5 mM $CaCl_2$, 0.5 mM $MgCl_2$ and 0.1% fetal bovine serum to PBS) and then once with PBS(+) (prepared by adding 0.5 mM $CaCl_2$ and 0.5 mM $MgCl_2$ to PBS). A formaldehyde solution diluted to 1.8% with PBS(+) was added to the washed cells, and the cells were fixed at 4° C. for 20 minutes. Next, the cells were washed once with PBS(+) and then treated with a glycine solution (0.2 M glycine, 100 mM Tris, pH 8.1) at 4° C. for 20 minutes and subsequently incubated in the washing buffer at 4° C. for 20 minutes, Next, the cells were allowed to react with HRP-conjugated streptoavidin diluted to 0.1 µg/ml with the binding buffer at 4° C. for 20 minutes and washed twice with the washing buffer and twice with PBS(+). By carrying out development of color using a peroxidase detection kit (ELISA POD Substrate OPD Kit, manufactured by Nacalai Tesque), the absorbance at 492 nm was measured and the activity of cell-bonded HRP was measured.

A value obtained by subtracting the absorbance for mock from the absorbance for each of the various mutant HB-EGF gene-transferred cells or human/mouse chimeric HB-EGF gene-transferred cells of the anti-HB-EGF antibody was used as the value A.

Next, in order to analyze expression of the mutant HB-EGF protein expressed on the cell membrane of mouse LMTK cell, the absorbance of an anti-HB-EGF rabbit polyclonal antibody which evenly binds to all of the mutant HB-EGF (antibody name; H-6, an antibody prepared by immunizing a rabbit with a synthetic peptide of positions 54 to 73 from the N-terminal of human HB-EGF, which was crosslinked to Sepharose CL-6B) for the mutant HB-EGF gene-transferred cell, human/mouse chimeric HB-EGF gene-transferred cell and mock was measured by the same method described in the above. However, the biotin-labeled H-6 antibody was used at an antibody concentration of 10 µg/ml. A value obtained by subtracting the absorbance for mock from the absorbance for each of the each mutant HB-EGF gene-transferred cell or human/mouse chimeric HB-EGF gene-transferred cell of the H-6 antibody was used as the value B.

In order to correct difference in the expressed amount between the gene-transferred cells, an A/B value was calculated by dividing value A by value B. The ratio of A/B value for each mutant HB-EGF when A/B value of anti-HB-EGF antibody for the positive control pRTHGC-6 was regarded as 100% was calculated, and this ratio was used as the relative binding activity for each mutant HB-EGF.

Figure 15:
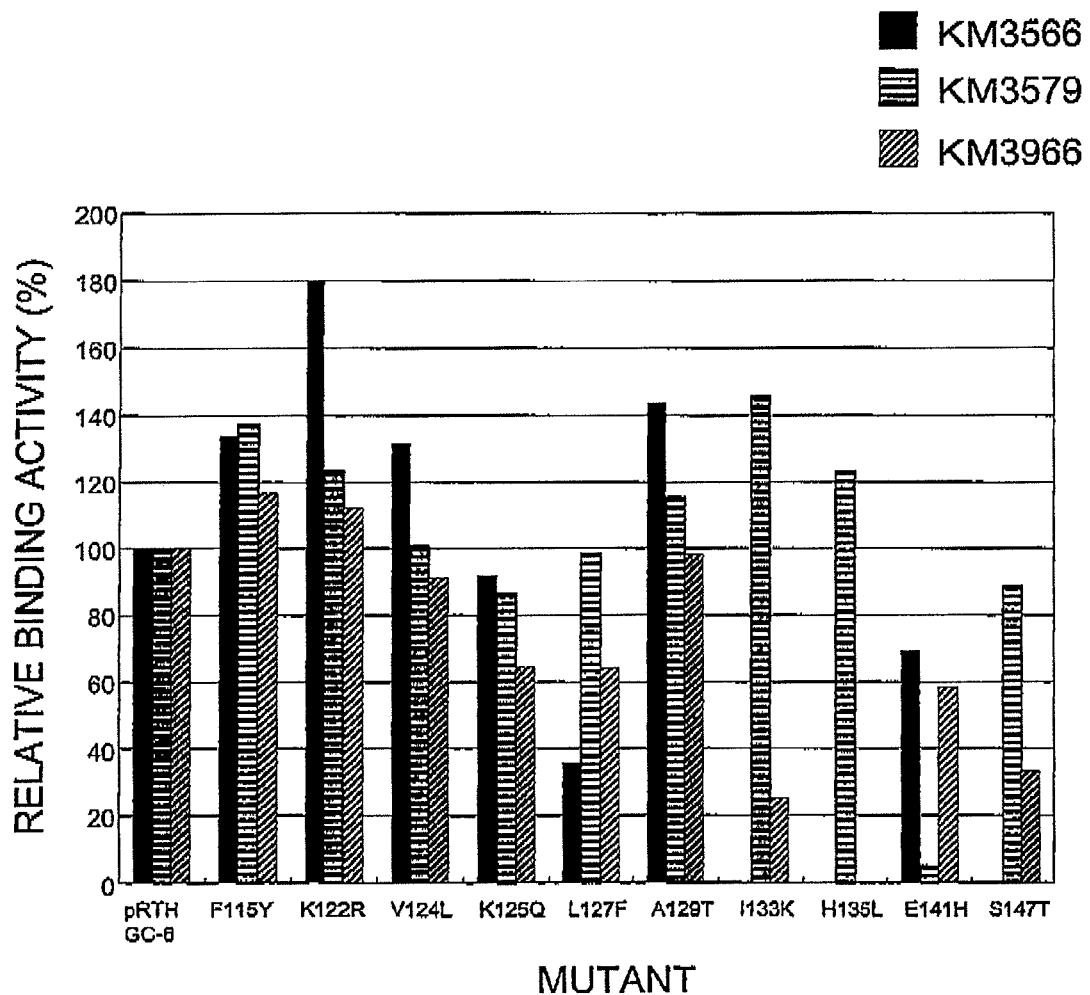
FIG. 15 shows the reactivity of anti-HB-EGF monoclonal antibodies KM3566 and KM3579 and chimeric antibody KM3966 for mutant HB-EGF expression cells. In the drawing, the ordinate shows the reactivity (%) of each antibody, and the abscissa shows kinds of mutant HB-EGF.

The results are shown in FIG. 15. In comparison with the pRTHGC-6, the anti-HB-EGF monoclonal antibody KM3566 hardly bound to I133K, H135L and S147T. Accordingly, it was found that the anti-FIB-EGF monoclonal antibody KM3566 recognizes an epitope comprising amino acids of I at position 133, H at position 135 and S at position 147. In addition, similar to the case of anti-HB-EGF monoclonal antibody KM3566, the anti-HB-EGF monoclonal antibody KM3966 having the same antibody variable region also hardly bound to I133K and H135L in comparison with the pRTHGC-6, and the binding activity for S147T was decreased to about ⅓. Thus, it was found that the anti-HB-EGF monoclonal antibody KM3966 recognizes an epitope comprising amino acids of I at position 133, H at position 135 and S at position 147, similar to the case of anti-HB-EGF monoclonal antibody KM3566.

In comparison with the pRTHGC-6, the anti-HB-EGF monoclonal antibody KM3579 did not bind only to E141H, and showed a binding activity of equivalent to pRTHGC-6 for all of the other mutant HB-EGF. Accordingly, it was found that the anti-HB-EGF monoclonal antibody KM3579 recognizes an epitope comprising the amino acid of E at position 141.

Based on the above results, it was found that the anti-HB-EGF monoclonal antibody KM3566 and anti-HB-EGF monoclonal antibody KM3966, and the anti-FIB-EGF monoclonal antibody KM3579 recognize different epitopes of HB-EGF.

INDUSTRIAL APPLICABILITY

The present invention provides a monoclonal antibody or an antibody fragment thereof which binds to a cell membrane-bound HB-EGF, a membrane type FIB-EGF and a secretory HB-EGF.

Free Text of Sequence Listing

SEQ ID NO:18—Description of artificial sequence: Synthetic DNA

SEQ ID NO:19—Description of artificial sequence: Synthetic DNA

SEQ ID NO:20—Description of artificial sequence: Synthetic DNA

SEQ ID NO:21—Description of artificial sequence: Synthetic DNA

SEQ ID NO:22—Description of artificial sequence: Amino acid sequence of humanized antibody SEQ ID NO:23—Description of artificial sequence: Amino acid sequence of humanized antibody SEQ ID NO:24—Description of artificial sequence: Synthetic DNA SEQ ID NO:25—Description of artificial sequence: Synthetic DNA SEQ ID NO:26—Description of artificial sequence: Synthetic DNA SEQ ID NO:27—Description of artificial sequence: Synthetic DNA SEQ ID NO:28—Description of artificial sequence: Synthetic DNA SEQ ID NO:29—Description of artificial sequence: Synthetic DNA SEQ ID NO:30—Description of artificial sequence: Synthetic DNA SEQ ID NO:31—Description of artificial sequence: Synthetic DNA

The invention claimed is:

1. An isolated monoclonal antibody or fragment thereof which binds to a cell membrane-bound heparin binding epidermal growth factor-like growth factor (HB-EGF), a membrane type HB-EGF or a secretory HB-EGF, wherein said antibody or said fragment comprises at least one heavy chain variable region and at least one light chain variable region, wherein said heavy chain variable region comprises three complementarity-determining regions comprising the amino acid sequences of SEQ ID NOS:12, 13 and 14; and wherein said light chain variable region comprises three complementarity-determining regions comprising the amino acid sequences of SEQ ID NOS:15, 16 and 17.

2. The monoclonal antibody or fragment thereof according to claim 1, wherein said antibody or said fragment binds to epidermal growth factor-like domain (EGF-like domain) of the cell membrane-bound HB-EGF, the membrane type HB-EGF or the secretory HB-EGF.

3. The monoclonal antibody or fragment thereof according to claim 1, wherein said antibody or said fragment inhibits binding of the secretory HB-EGF and an HB-EGF receptor.

4. The monoclonal antibody or fragment thereof according to claim 1, wherein said antibody or said fragment neutralizes the secretory HB-EGF.

5. The monoclonal antibody or fragment thereof according to claim 1, wherein said antibody or said fragment binds to a binding region of the secretory HB-EGF and an HB-EGF receptor.

6. The monoclonal antibody or fragment thereof according to claim 1, wherein said antibody or said fragment binds to an epitope comprising at least one amino acid at position 133, 135 or 147 in the amino acid sequence of SEQ ID NO:2.

7. The monoclonal antibody or fragment thereof according to claim 6, wherein said antibody or said fragment binds to an epitope comprising amino acids at positions 133, 135 and 147 in the amino acid sequence of SEQ ID NO:2.

8. The monoclonal antibody or fragment according to claim 1, wherein said antibody or said fragment binds to an epitope to which a monoclonal antibody produced by hybridoma KM3566 (PERM BP-10490) binds.

9. The monoclonal antibody or fragment thereof according to claim 1, wherein the monoclonal antibody is a recombinant antibody.

10. The monoclonal antibody or the antibody fragment thereof according to claim 9, wherein the recombinant antibody is selected from the group consisting of a human chimeric antibody and a humanized antibody.

11. The monoclonal antibody or the antibody fragment thereof according to claim 10,
wherein the recombinant antibody is a human chimeric antibody, and
said antibody or said fragment comprises at least one heavy chain variable region and at least one light chain variable region, wherein said heavy chain variable region comprises the amino acid sequence of SEQ ID NO:9, and wherein said light chain variable region comprises the amino acid sequence of SEQ ID NO:11.

12. The monoclonal antibody or the antibody fragment thereof according to claim 10,
wherein the recombinant antibody is a humanized antibody, and
wherein the heavy chain variable region of the antibody comprises the amino acid sequence of SEQ ID NO:22 or an amino acid sequence in which at least one modification is made, wherein said modification is a substitution selected from the substitutions of Ala at position 9 with Thr, Val at position 20 with Leu, Thr at position 30 with Arg, Arg at position 38 with Lys, Pro at position 41 with Thr, Met at position 48 with Ile, Arg at position 67 with Lys, Val at position 68 with Ala, Ile at position 70 with Leu, Tyr at position 95 with Phe, and Val at position 118 with Leu in the amino acid sequence of SEQ ID NO:22; and
wherein said light chain variable region comprises the amino acid sequence of SEQ ID NO:23 or an amino acid sequence in which at least one modification is made, wherein said modification is a substitution selected from the substitutions of Leu at position 15 with Val, Ala at position 19 with Val, Ile at position 21 with Met, Pro at position 49 with Ser, and Leu at position 84 with Val.

13. The monoclonal antibody or fragment according to claim 1, wherein the antibody fragment is selected from the group consisting of Fab, Fab', F(ab')2, a single chain antibody (scFv), a diabody, and a disulfide stabilized Fv (dsFv).

* * * * *